United States Patent [19]

Egbertson et al.

[11] Patent Number: 5,648,368

[45] Date of Patent: Jul. 15, 1997

[54] FIBRINOGEN RECEPTOR ANTAGONISTS

[75] Inventors: Melissa S. Egbertson, Ambler; Laura M. Vassallo, Havertown; George D. Hartman; Wasyl Halczenko, both of Lansdale; David B. Whitman, Phoenixville; James J. Perkins, Philadelphia; Amy E. Krause, Blue Bell; Nathan Ihle, Perkasie; David Alan Claremon, Maple Glen; William Hoffman, Lansdale; Mark E. Duggan, Schwenksville, all of Pa.

[73] Assignee: Merck & Co., Inc., Rahway, N.J.

[21] Appl. No.: 448,347

[22] PCT Filed: Nov. 29, 1993

[86] PCT No.: PCT/US93/11623

§ 371 Date: Jun. 1, 1995

§ 102(e) Date: Jun. 1, 1995

[87] PCT Pub. No.: WO94/12181

PCT Pub. Date: Jun. 9, 1994

[51] Int. Cl.⁶ .................. A61K 31/445; C07D 211/20; C07D 211/26; C07D 211/98
[52] U.S. Cl. ............. 514/331; 514/327; 514/329; 514/330; 546/233; 546/234
[58] Field of Search ................. 546/233, 234; 514/331, 330, 327, 329

[56] References Cited

U.S. PATENT DOCUMENTS

| | | | |
|---|---|---|---|
| 4,064,255 | 12/1977 | Champseix et al. | 544/168 |
| 4,098,789 | 7/1978 | Krapcho | 544/299 |
| 4,122,255 | 10/1978 | Krapcho | 544/168 |
| 4,243,807 | 1/1981 | Friebe et al. | 546/232 |
| 4,622,331 | 11/1986 | Jozic | 514/331 |
| 5,030,654 | 7/1991 | Barnish et al. | 514/510 |
| 5,064,814 | 11/1991 | Klein et al. | 514/18 |
| 5,252,586 | 10/1993 | Cain et al. | 514/317 |
| 5,272,158 | 12/1993 | Hartman et al. | 514/323 |
| 5,321,034 | 6/1994 | Duggan et al. | 514/323 |
| 5,358,956 | 10/1994 | Hartman et al. | 514/331 |

FOREIGN PATENT DOCUMENTS

| | | |
|---|---|---|
| 0 352 249 | 1/1990 | European Pat. Off. . |
| 0 372 486 | 6/1990 | European Pat. Off. . |
| 0 381 033 | 8/1990 | European Pat. Off. . |
| 0 384 362 | 8/1990 | European Pat. Off. . |
| 0 405 537 | 1/1991 | European Pat. Off. . |
| 0 478 328 | 4/1992 | European Pat. Off. . |
| 0 478 362 | 4/1992 | European Pat. Off. . |
| 0 478 363 | 4/1992 | European Pat. Off. . |
| 0 479 481 | 4/1992 | European Pat. Off. . |
| 92/19595 | 11/1992 | WIPO . |
| 94/08577 | 4/1994 | WIPO . |

OTHER PUBLICATIONS

Umibe, et al., Chemical Abstracts, vol. 117, Ab. No. 242462 "Alkylaminobenzonitrile or alkylaminophenylacetic acid", 1992.

Primary Examiner—C. Warren Ivy
Assistant Examiner—D. Margaret M. Mach
Attorney, Agent, or Firm—Richard S. Parr; Mel Winokur

[57] ABSTRACT

Novel fibrinogen receptor antagonists of the formula:

X—Y—Z—Aryl—A—B are provided in which the claimed compounds exhibit fibrinogen receptor antagonist activity, inhibit platelet aggregation and are therefore useful in modulating thrombus formation.

13 Claims, No Drawings

FIBRINOGEN RECEPTOR ANTAGONISTS

This application is a 371 of PCT/US93/11623, filed 29 Nov. 1993.

BACKGROUND OF THE INVENTION

The invention relates generally to modulating cRe:
Patenthe binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are anucleated cells, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. These proteins contain the tripeptide sequence arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigentically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Hayerstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., J. Biol. Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. USA, 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$—A—$(W)_a$—X—$(CH_2)_b$—$(Y)_c$—B—Z—

COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

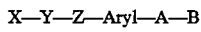

X—Y—Z—Aryl—A—B and the pharmaceutically acceptable salts thereof wherein:

Aryl is a 6-membered monocyclic aromatic ring system containing 0, 1, 2, 3, or 4N atoms and either unsubstituted or substituted with $R^5$;

X is

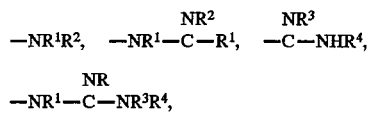

$-NR^1R^2$, $-NR^1-C(NR^2)-R^1$, $-C(NR^3)-NHR^4$, $-NR^1-C(NR)-NR^3R^4$, or a 4- to 10-membered mono- or polycyclic aromatic or nonaromatic ring system and containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, $C_{3-8}$ cycloalkyl, aryl $C_{0-8}$ alkyl, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, or hydroxy $C_{0-6}$ alkyl;

Y is $C_{0-8}$ alkyl, $C_{4-10}$ cycloalkyl, $C_{0-8}$ alkyl—$NR^3$—CO—$C_{0-8}$ alkyl, $C_{0-8}$ alkyl—$CONR^3$—$C_{0-8}$ alkyl, $C_{0-8}$ alkyl—O—$C_{0-8}$ alkyl, $C_{0-8}$ alkyl—$S(O_n)$—$C_{0-8}$ alkyl, $(CH_2)_{0-8}$aryl$(CH_2)_{0-8}$, $(CH_2)_{0-6}$aryl—$SO_n$—$(CH_2)_{0-8}$aryl—CO—$(CH_2)_{0-8}$, $(CH_2)_{0-6}$aryl—$SO_2$—$(CH_2)_{0-6}$, $(CH_2)_{0-6}$—$NR^3$—$(CH_2)_{0-6}$, $(CH_2)_{0-6}$—aryl—CH(OH)—$(CH_2)_{0-6}$, $(CH_2)_{0-8}$aryl—CONH—$(CH_2)_{0-8}$, $C_{0-8}$ alkyl—$SO_2$—$NR^3$—$C_{0-8}$ alkyl—, $C_{0-8}$ alkyl—CO—$C_{0-8}$ alkyl, or $C_{0-8}$ alkyl—CH(OH)—$C_{0-8}$—alkyl where n is an integer from 0–2;

Z and A are independently chosen from $(CH_2)_m$, $(CH_2)_mO(CH_2)_n$, $(CH_2)_mCNR^3(CH_2)_n$, $(CH_2)_mNR^3C(CH_2)_n$, $(CH_2)_mC(CH_2)_n$, $(CH_2)_mC(CH_2)_n$, $(CH_2)_mSO_2(CH_2)_n$, $(CH_2)_mS(CH_2)_n$, $(CH_2)_mSO(CH_2)_n$,
$(CH_2)_mSO_2NR^3(CH_2)_n$, $(CH_2)_mNR^3SO_2(CH_2)_n$, -continued $(CH_2)_mCR^3=CR^4(CH_2)_n$, $(CH_2)_mC=C(CH_2)_n$, and $(CH_2)_mCH(OH)(CH_2)_n$, where m and n are integers independently chosen from 0–6; provided that when A is $(CH_2)_m$, the Aryl ring, bonded by Z and A, must contain at least one heteroatom;

$R^5$ is hydrogen $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, aryl $C_{0-6}$ alkyl, or halogen;

B is

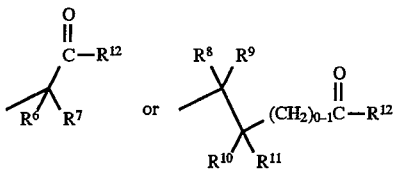

wherein $R^6$, $R^7$, $R^8$, $R^9$, $R^{10}$, and $R^{11}$ are independently chosen from:

hydrogen, fluorine, hydroxy $C_{1-6}$ alkyl, carboxy $C_{0-6}$ alkyl, $C_{1-8}$ alkyl, hydroxyl, $C_{1-6}$ alkyloxy, aryl $C_{0-6}$alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-8}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{0-8}$ alkylaminocarbonyl $C_{0-8}$ alkyl, aryl $C_{0-8}$ alkylaminocarbonyl $C_{0-8}$ alkyl, $C_{0-8}$ alkylaminosulfonyl $C_{0-8}$ alkyl, and aryl $C_{0-8}$ alkylaminosulfonyl $C_{0-8}$ alkyl, wherein groups may be unsubstituted or substituted with one or more substituents selected form $R^1$ and $R^2$; and $R^{12}$ is chosen from hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, and an L- or D-amino acid joined by an amide linkage and wherein the carboxylic acid moiety of said amino acid is as the free acid or is esterified by $C_{1-6}$ alkyl.

When substituent $R^1$, $R^2$, $R^3$, $R^4$, $R^5$, $R^6$, $R^7$, $R^8$, $R^9$, $R^{10}$, $R^{11}$, $R^{12}$, X or Y includes the definition $C_0$, (e.g. aryl $C_0$ alkyl), the group modified by $C_0$ is not present in the substituent.

A prefered embodiment of the present invention is

X—Y—Z—Aryl—A—B and the pharmaceutically acceptable salts thereof wherein:

Aryl is a 6-membered aromatic ring system containing 0, 1, 2, or 3N atoms;

X is $-NR^1R^2$, $-NR^1-C(NR^2)-R^1$, $-C(NR^3)-NHR^4$,

-continued

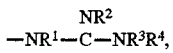

or a 4- to 10-membered mono- or polycyclic aromatic or nonaromatic ring system containing 0, 1, 2, 3 or 4 heteroatoms selected from N, O and S and either unsubstituted or substituted with $R^1$, $R^2$, $R^3$, or $R^4$, wherein $R^1$, $R^2$, $R^3$ and $R^4$ are independently selected from the group consisting of hydrogen, $C_{1-10}$ alkyl, $C_{3-8}$ cycloalkyl, aryl $C_{0-8}$ alkyl, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

Y is $C_{0-8}$ alkyl, $C_{0-8}$ alkyl—$NR^3$—CO—$C_{0-8}$ alkyl, $C_{0-8}$ alkyl—$CONR^3$—$C_{0-8}$ alkyl, $C_{0-8}$ alkyl—O—$C_{0-8}$ alkyl, $C_{0-8}$ alkyl aryl $C_{0-8}$ alkyl, $C_{0-8}$ alkyl—$S(O_n)$—$C_{0-8}$ alkyl, $C_{0-8}$ alkyl—$SO_2$—$NR^3$—$C_{0-8}$ alkyl—, or $C_{0-8}$ alkyl—CO—$C_{0-8}$ alkyl—, where n is an integer from 0–2;

Z and A are independently chosen from:

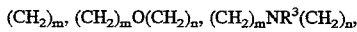

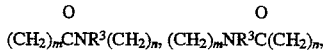

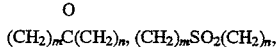

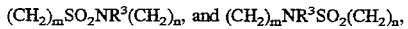

where m and n are integers independently chosen from 0–6; provided that when A is $(CH_2)_m$, the Aryl ring bonded by Z and A, must contain at least one heteroatom;

B is

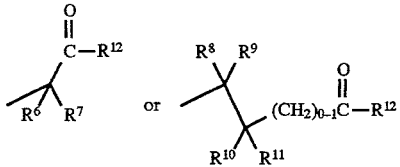

wherein $R^6$, $R^7$, $R^8$, $R^9$, $R^{10}$ and $R^{11}$ are independently chosen from:

hydrogen, flourine $C_{1-8}$ alkyl, $C_{3-8}$ cycloalkyl, aryl $C_{0-6}$ alkyl, $C_{0-6}$ alkylamino $C_{0-6}$ alkyl, aryl $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, and aryl $C_{0-6}$ alkylcarbonyl $C_{0-6}$ alkyl; and $R^{12}$ is chosen from: hydroxy, $C_{1-8}$ alkyloxy, aryl $C_{0-6}$ alkyloxy, $C_{1-8}$ alkylcarbonyloxy $C_{1-4}$ alkyloxy, and aryl $C_{1-8}$ alkylcarbonyloxy $C_{1-4}$ alkyloxy.

A more prefered embodiment of the present invention is:

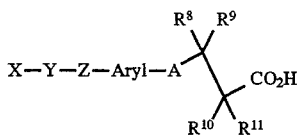

and the pharmaceutically acceptable salts thereof wherein:

Aryl is a 6-membered monocyclic aromatic ring system containing 0, 1 or 2N atoms;

X is

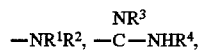

or a 4- to 8-membered nonaromatic ring system containing 0, 1, 2 or 3 heteroatoms selected from N and O wherein $R^1$, $R^2$, $R^3$ and $R^4$ are independently selected from the group consisting of hydrogen, $C_{1-10}$ alkyl, aryl $C_{0-8}$ alkyl, carboxy $C_{0-6}$ alkyl, hydroxy $C_{0-6}$ alkyl, amino $C_{0-8}$ alkyl, or $C_{1-6}$ alkylamino $C_{0-8}$ alkyl;

Y is $C_{0-8}$ alkyl, $C_{0-8}$ alkyl—$NR^3$—CO—$C_{0-8}$ alkyl, $C_{0-8}$ alkyl—$CONR^3$—$C_{0-8}$ alkyl, $C_{0-8}$ alkyl—O—$C_{0-8}$ alkyl, $C_{0-8}$ alkyl—$S(O_n)$—$C_{0-8}$ alkyl, or $C_{0-8}$ alkyl aryl $C_{0-8}$ alkyl;

Z and A are independently chosen from

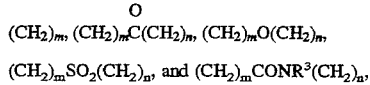

wherein m and n are integers independently chosen from 0–6 and provided that when A is $(CH_2)_m$, the Aryl ring bounded by Z and A, must contain at least one heteroatom; and $R^8$, $R^9$, $R^{10}$ and $R^{11}$ are independently chosen from hydrogen, fluorine $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, and aryl $C_{0-6}$ alkylcarbonyl $C_{0-6}$ alkyl

DETAILED DESCRIPTION OF THE INVENTION

The term "pharmaceutically acceptable salts" shall mean non-toxic salts of the compounds of this invention which are generally prepared by reacting the parent compound with a suitable organic or inorganic acid or base. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" means that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" shall include aspirin and dipyridamole.

The term "alkyl" means straight or branched alkane, alkene or alkyne. The term "alkoxy" includes an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

Under standard nomenclature used throughout this disclosure, the terminal portion of the designated side chain is described first followed by the adjacent functionallity toward the point of attachment. For example, a $C_{1-6}$ alkyl substituted with $C_{1-6}$ alkylcarbonylamino is equivalent to

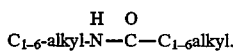

The term "Aryl" is different from the term "aryl", wherein "Aryl" is defined in its broadest scope as a 6-membered monocyclic aromatic ring system containing 1, 2, 3 or 4N atoms, and either unsubstituted or substituted. The term "aryl" is now defined to be a mono- or polycyclic ring system containing 0, 1, 2, 3, 4 or 5 heteroatoms chosen from N, O and S, comprised of 5- or 6-membered rings, either unsubstitued or substituted with substituents chosen from $R^1$ and $R^2$.

In the schemes and examples below, various reagent symbols have the following meanings:

BOC(Boc): t-Butyloxycarbonyl.
Pd/C: Palladium on activated carbon catalyst.
DEAD: Diethylazodicarboxylate.
DIAD: Diisopropylazodicarboxylate.
DMF: Dimethylformamide.
DMSO: Dimethylsulfoxide.
CBZ: Benzyloxycarbonyl.
$CH_2Cl_2$: Methylene chloride.
$CHCl_3$: chloroform.
EtOH: ethanol.
MeOH: methanol.
EtOAc: ethyl acetate.
HOAc: acetic acid.
BOP: Benzotriazol-1-yloxytris(dimethylamino) phosphonium, hexafluorophosphate.
EDC: 1-(3-Dimethylaminopropyl)-3-ethylcarbodiimide.
Oxone: potassium peroxymonosulfate.
LDA: Lithium diisopropylamide.
CDI: Carbonyldiimidazole.
NMM: N-Methylmorpholine.
DIPEA: Diisopropylethylamine.

TMSI: Trimethylsilyliodide.
TFA: Trifluoroacetic acid.
py: Pyridine.

The compounds of the present invention can be administered in such oral froms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compounds of the invention may be administered to prevent adhesion.

Other applications of these compounds include prevention of thrombosis, thromboembolism and reocclusion during and after thrombolytic therapy and prevention of thrombosis, thromboembolism and reocclusion after angioplasty or coronary artery bypass procedures. They may also be used to prevent or modulate myocardial infarction.

The dosage regimen utilizing the compounds of the present invention is selected in accordance with a variety of factors including type, species, age, weight, sex and medical condition of the patient; the severity of the condition to be treated; the route of adminstration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylkcellulose, polyethylene glycol, waxes and the like. Lubricants used in these dosage forms include sodium oleate, sodium sterate, magnesium sterate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug cariers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-coagulation agents or thrombolytic agents such as plasminogen activators or streptokinase to acheive synergistic effects in the treatment of various vascular pathologies. They may also be combined with heparin, aspirin, or warfarin.

Preferred compounds of the invention are selected from the group consisting of:

N-[2-(4-Piperidinylethyl)-N'-(2-carboxyethyl)]-1,3-benzenedicarboxamide;
N-2-(4-Piperidinylethyl)-N'-[3-(2-fluoro)propanoic-acid]-1,3-benzenedicarboxamide;
{N-2-(4-Piperidinylethyl)-N'-3-[3(R)-phenethylpropanoic acid]}-1,3-benzenedicarboxamide;
{N-[2-(4-Piperidinylethyl)]-N'-3-[3(R)-indolylethylpropanoic acid]}-1,3-benzenedicarboxamide;
N-(4-Piperidinylmethyl)-N'-3-[2(S)-n-butylsulfonylaminopropionic acid]-1,3-benzenedicarboxamide;
N-(4-Piperidinylmethyl)-N'-(2-carboxyethyl)-1,3-benzenedicarboxamide;
N-2-(4-Piperidinyl)ethyl-N'-(2-carboxyethyl)-2-methyl-1,3-benzenedicarboxamide;
3-[(4-Piperidinyl)methyloxy]-N-(2-carboxyethyl) phenylacetamide;
4-(Piperidin-4-yl)phenyl-3-propionyl-[2(S)-n-butylsulfonylamino]-β-alanine;
4-(1,2,5,6-Tetrahydropyridin-4-yl)phenyl-3-propionyl-[2(S)-n-butylsulfonylamino]-β-alanine;
3-[3-(Piperidin-4-ylmethyl)phenyl]propionyl-β-alanine;
3-[4-(1,2,5,6-Tetrahydropyridin-4-yl)]butyryl-β-alanine;
{N-2-(4-Piperidinylethyl)-N'-3-[2(S)-n-butylsulfonylaminopropanoic acid]}-1,3-benzenedicarboxamide;
N-2-(4-Piperidinyl)ethyl-N'-3-[2(S)-n-butylsulfonylaminopropionic acid]-2-methyl-1,3-benzenedicarboxamide;
{N-[2-(4-Piperidinyl)ethyl]-N-(phenethyl)}-N'-(2-carboxyethyl)-1,3-benzenedicarboxamide;
N-[2-(4-Piperidinyl)ethyl-N-propyl]-N'-(2-carboxyethyl)-1,3-benzenedicarboxamide;
N-2-(4-Piperidinyl)ethyl-N'-[3-(2(S)-hexanoylaminopropionic acid)]-1,3-benzenedicarboxamide;
[N-2-(4-Piperidinyl)ethyl]-N'-[3-2(S)-thien-2-yl-sulfonylaminopropionic acid]-1,3-benzenedicarboxamide;
4-methyl-N-[2-(4-piperidinyl)ethyl]-N'-2-(carboxyethyl)-1,3-benzenedicarboxamide;
3-[(2-Carboxyethyl)aminosulfonyl]-N-[2-(4-piperidinylethyl)]-benzamide;
3-[2-(4-Piperidinyl)ethylaminosulfonyl]-N-[(2-carboxyethyl)]-benzamide;
3-[(4-Piperidinyl)methylaminosulfonyl]-N-[(2-carboxyethyl)]-benzamide;
N-[(2-(N-BOC-4-Piperidinyl)ethyl)]-N'-[2-carboxyethyl]-3,5-pyridinedicarboxamide;
N-[2-(4-Piperidinyl)ethyl]-N'-[(2-carboxy)ethyl]-2,6-pyridinedicarboxamide;
3-(3-Carboxypropyloxy)-N-(4-piperidinylmethyl) carboxamide;
N-2-(4-Piperidinylethyl)-N'-3-(2-benzylpropionic acid)-1,3-benzenedicarboxamide;
3-(5-Carboxypentanoyl)-N-(4-piperidinylmethyl) benzenecarboxamide;
3-(6-Carboxyhexanoyl)-N-(4-piperidinylmethyl) benzenecarboxamide;
4-(Piperidin-4-yl)phenyl-3-propionyl-β-alanine;
4-(1,2,5,6-Tetrahydropyridin-4-yl)phenyl-3-propionyl-β-alanine;
6-[2-(Piperidin-4-yl)ethyloxy]nicotinamide-N-[3-(2(S)-phenylsulfonylamino]propionic acid;
3-Chloro-4-[2-(Piperidin-4-yl)ethyloxy]phenylcarbonyl-2(S)-phenylsulfonylamino-β-alanine;
4-[3-(Piperidin-3-yl)propyloxy]-N-[3-(2(S)-butylsulfonylamino)propionic acid]benzamide;
4-[2-(Piperidin-4-yl)ethyloxy]phenylcarboxyl-2-(S)-hydroxy-β-alanine.
N-[3-(2(S)-Phenylsulfonylamino)propionate]-4'-aminomethyl-4-biphenylcarboxamide;
N-[3-(2(S)-Phenylsulfonylamino)propionate]-4'-amidino-4-biphenylcarboxamide;
4-[3-(Pyridin-4-yl)propyloxy]benzoyl-2(S)-phenylsulfonylamino-β-alanine;
4-[3-(Pyridin-4-yl)propyl]benzoyl-2(S)-phenylsulfonylamino-β-alanine;
4-[2-(Piperidin-4-yl)oxyethyloxy]benzoyl-2(S)-phenylsulfonylamino-β-alanine;
4-N-(Piperazinyl)benzoyl-2(S)-phenylsulfonylamino-β-alanine;
4-[2-(N,N-Diethylamino)ethyloxy]benzoyl-2(S)-phenylsulfonylamino-β-alanine;
4-[4-(N-Morpholino)butyloxy]benzoyl-2(S)-phenylsulfonylamino-β-alanine;
4-[2-(N-Benzylimidazol-4-yl)ethyloxy]benzoyl-2(S)-phenylsulfonylamino-β-alanine;
4-[2-(Imidazol-4-yl)ethyloxy]benzoyl-2(S)-phenylsulfonylamino-β-alanine;
4-[3-(1-Methylimidazol-4-yl)propyloxy]benzoyl-2(S)-phenylsulfonylamino-β-alanine methyl ester;
4-[3-(1-Methylimidazol-4-yl)propyloxy]benzoyl-2(S)-phenylsulfonylamino-β-alanine;

4-[3-(1-Imidazolyl)propyloxy]benzoyl-2(S)-phenylsulfonylamino-β-alanine t-butyl ester;

4-[3-(1-Imidazolyl)propyloxy]benzoyl-2(S)-phenylsulfonylamino-β-alanine;

4-[2-(Pyrrolidinyl)ethyloxy]benzoyl-2(S)-phenylsulfonylamino-β-alanine;

2(S)-Phenylsulfonylamino-4-(4-piperazinylphenoxy)butanoic acid;

t-Butyl 2(S)-t-Butyloxycarbonylamino-4-[4-(N-methylpiperazinyl)phenoxy]butanoate;

2(S)-Amino-3-[4-(N-methylpiperazinyl)phenoxy]butanoic acid;

2(S)-3-Pyridylsulfonylamino-4-[4-(N-methylpiperazinyl)phenoxy]-butanoic acid;

4-[(4-Pyrrolidinylbut-2-enyl)oxy]benzoyl-2(S)-phenylsulfonylamino-β-alanine t-butyl ester;

4-[(4-Pyrrolidinylbut-2-enyl)oxy]benzoyl-2(S)-phenylsulfonylamino-β-alanine;

3-[(N-Boc-Piperidin-4-ylmethyl)aminocarbonyl]benzoyl-2(S)-3-pyridylsulfonylamino-β-alanyl-glycine benzyl ester;

3-[(Piperidin-4-ylmethyl)aminocarbonyl]benzoyl-2(S)-3-pyridylsulfonylamino-β-alanyl-glycine;

4-[(2-Aminoethyl)aminocarbonyl]benzoyl-2-(S)-phenylsulfonylamino-β-alanine;

4-[(2-Guanidinoethyl)aminocarbonyl]benzoyl-2(S)-phenylsulfonylamino-β-alanine;

4-[(4-N-Methylaminobutyl)aminocarbonyl]benzoyl-2(S)-3-pyridylsulfonylamino-β-alanine;

{N-2-(4-Piperidinylethyl)-N'-3-[ethyl 2(S)-n-butylsulfonylaminopropanoate]}-1,3-benzenedicarboxamide;

4-[2-(4-Piperidinyl)ethyloxy]-N-[3-(2(S)-n-butylsulfonylamino)propionate]benzamide;

4-[2-(4-Piperidinyl)ethyloxy]-N-[3-(2(S)-n-phenylsulfonylamino)propionate]benzamide;

3-[3-(Piperidin-4-ylmethyl)phenyl]propionyl-β-alanine; and

3-[(4-Piperidinyl)methyloxy]-N-[3-(2-indol-3-yl)ethyl-propionic acid]phenyl acetamide.

Platelet aggregation is measured at 37° C. in a Chronolog aggregometer. The reaction mixture contains gel-filtered human platelets (2×10⁸ per ml), fibrinogen (100 micrograms per ml (ug/ml)), $Ca^{2+}$ (1 mM), and the compound to be tested. The aggregation is initiated by adding 10 μM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Activities of some of the preferred compounds, characterized by $IC_{50}$ for inhibition of ADP-mediated platelet aggregation, are listed below:

| | $IC_{50}$ |
|---|---|
| 3-[4-(1,2,5,6-Tetrahydropyridine)-phenyl]butyryl-β-alanine | 1.3 μM |
| 3-[3-Piperidin-4-ylmethyl]phenyl]-propionyl-β-alanine; | 170 μM |
| 3-[4-Piperidinyl)methoxy]-N-[3-(2-indol-3-yl)ethylpropionic acid]phenyl-acetamide; | 5.2 μM |
| 3-[(4-Piperidinyl)methloxy]-N-(2-carboxyethyl)-phenyl acetamide; | 56 μM |
| 4-(4-Piperidin-4-yl)-N-3[2(S)-n-butylsulfonylaminopropionic acid]-phenylbutyramide; | 0.095 μM |
| 4-[2-(Piperidin-4-yl)ethoxy]benzoyl-2(S)-phenylsulfonylamino-β-alanine; | 0.014 μM |
| 4-(Piperidin-4-yl)phenyl-3-propionyl-[2(S)-n-butyl-sulfonylamino]-β-alanine; | 0.10 μM |
| 3-[4-(1,2,5,6-Tetrahydropyridin-4-yl)-phenyl]butyryl-β-alanine; | 1.3 μM |
| 4-(1,2,5,6-Tetrahydropyridin-4-yl)-phenyl-3-propionyl-[2(S)-butylsulfonylamino]-β-alanine; | 0.022 μM |
| 4-(Piperidin-4-yl)-phenyl-3-propionyl-β-alanine; | 11 μM |
| 4-(1,2,5,6-Tetrahydropyridin-4-yl)-phenyl-3-propionyl-β-alanine; | 1.7 μM |

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

Compounds of the present invention are prepared from dicarboxylic acids by a sequence of carboxyl activation with CDI or other suitable reagent, followed by amide bond formation. In this manner, representative compounds of Schemes 1, 2, 3 and 7 may be prepared using amines that have been previously protected as esters or carbamates. Subsequent to coupling with, for example, a CBZ-protected amine, the product may be deprotected at a N site and functionalized to a sulfonamide or amide via sulfonylating or acylating reagents, respectively.

Differentially functionalized chlorosulfonyl benzoic acids, as shown in Schemes 3 and 4, may be prepared from the corresponding sulfonic acid and, via treatment with appropriate amines, provide functionalized aryl sulfonamides. Subsequent activation of carboxyl groups followed by amide bond formation may provide further examples of desired compounds.

Ether analogs, such as shown in Schemes 9 and 13 may be prepared by treatment of the appropriate hydroxy carboxylic acid with a base, such as NaH, to form the alkoxide followed by reaction with an alkylating agent. This alkylating agent may encompass suitably protected amine components. Subsequent to alkylation, carboxyl activation and amide formation may provide advanced synthetic intermediates. Deprotection as appropriate may then provide key products of the present invention.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

SCHEME 1

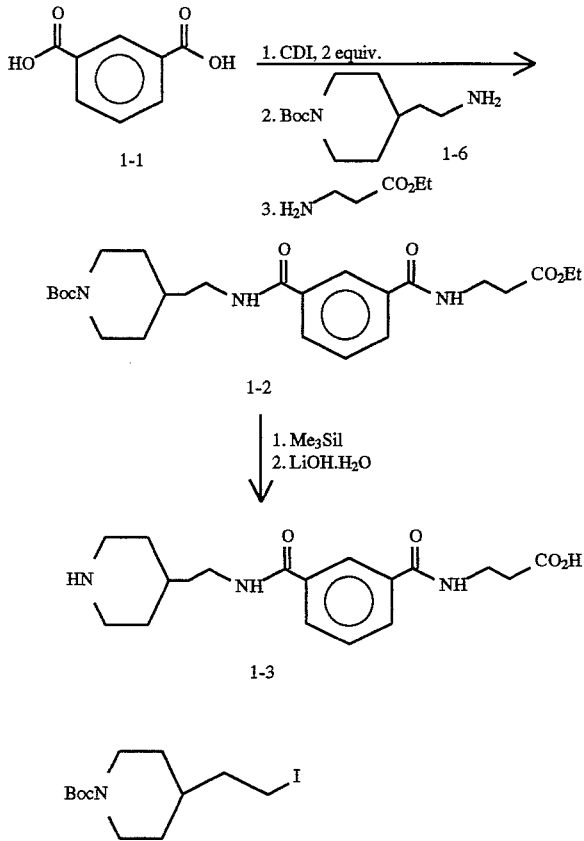

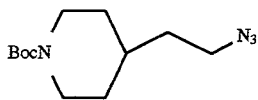

2-(N-Boc-4-Piperidinyl)ethyl Iodide (1-4)

1-4 is prepared according to the procedure described in European Publication 540,334, specifically at pages 17–18 and 21 of that publication, for preparing compound 1-6 of EP 540,334. Boc-4-piperidine-2-ethanol (10.42 g, 0.048 moles) was dissolved in benzene (400 ml), and imidazole (4.66 g, 0.068 moles) and triphenylphosphine (13.24 g, 0.05 moles) were added at room temp, followed by iodine (12.9 g, 0.05 mol). After 6 hours the reaction mixture was filtered and the filtrate was evaporated to give a dark residue. This was purified by flash chromatography on silica gel eluting with 10% EtOAc/hexanes to give 1-4 as a yellow oil. $R_f$ 0.3 (silica, 10% EtOAc/hexanes).

2-(N-Boc-4-Piperidinyl)ethyl Azide (1-5)

To 1-4 (27.9 g, 0.082 moles) dissolved in DMSO (400 ml) was added sodium azide (5.61 g, 0.086 moles) at room temperature and the resulting solution was heated at 65° for 2 hrs. The cooled reaction mixture was diluted with 250 ml EtOAc, extracted with 2×100 ml portions of water, 2×50 ml portions of brine and then dried (MgSO$_4$). Solvent removal provided 1-5 as a pale yellow oil, $R_f$ 0.5 (silica gel, 20% acetone/hexane).

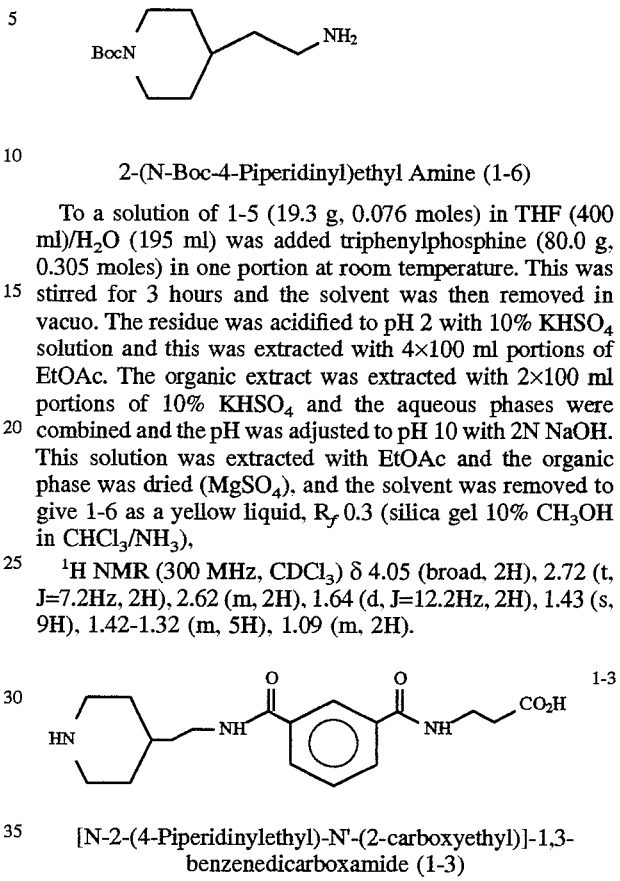

2-(N-Boc-4-Piperidinyl)ethyl Amine (1-6)

To a solution of 1-5 (19.3 g, 0.076 moles) in THF (400 ml)/H$_2$O (195 ml) was added triphenylphosphine (80.0 g, 0.305 moles) in one portion at room temperature. This was stirred for 3 hours and the solvent was then removed in vacuo. The residue was acidified to pH 2 with 10% KHSO$_4$ solution and this was extracted with 4×100 ml portions of EtOAc. The organic extract was extracted with 2×100 ml portions of 10% KHSO$_4$ and the aqueous phases were combined and the pH was adjusted to pH 10 with 2N NaOH. This solution was extracted with EtOAc and the organic phase was dried (MgSO$_4$), and the solvent was removed to give 1-6 as a yellow liquid, $R_f$ 0.3 (silica gel 10% CH$_3$OH in CHCl$_3$/NH$_3$), $^1$H NMR (300 MHz, CDCl$_3$) δ 4.05 (broad, 2H), 2.72 (t, J=7.2Hz, 2H), 2.62 (m, 2H), 1.64 (d, J=12.2Hz, 2H), 1.43 (s, 9H), 1.42-1.32 (m, 5H), 1.09 (m, 2H).

[N-2-(4-Piperidinylethyl)-N'-(2-carboxyethyl)]-1,3-benzenedicarboxamide (1-3)

To 1,3-benzenedicarboxylic acid (Aldrich) (0.36 g, 0.22 mmoles) in 3 ml DMF was added carbonyldiimidazole (CDI) (0.71 g, 0.44 mmoles) in small portions as the reaction mixture vigorously evolved gas. After stirring at room temperature for 0.5 hr 1-6 (0.5 g, 0.22 mmoles) in 2 ml DMF was added and the resulting solution was stirred for 12 hours. Then, N-methyl-morpholine (NMM) (0.72 ml, 0.66 mmoles) was added followed by β-alanine ethyl ester (0.33 g, 0.22 mmoles) and the resulting mixture was stirred at room temperature for 6 hours.

The solvent was removed and the residue was taken up in H$_2$O, acidified with 10% aqueous KHSO$_4$ solution, and this was extracted with EtOAc. The extracts were dried (MgSO$_4$), and the solvent was removed to afford a residue that was purified by flash chromatography on silica gel eluting with 3% methanol/CH$_2$Cl$_2$ to give [N-Boc-2-(4-piperidinylethylamino-N'-(2-carboethoxyethylamino]-1,3-benzenedicarboxamide (1-2% $R_f$ 0.3 (silica gel, 5% MeOH/CH$_2$Cl$_2$).

$^1$H NMR (300 MHz, CDCl$_3$) δ 8.18 (s, 1H), 7.93 (d, J=7.8Hz, 1H), 7.86 (d, J=7.8Hz, 1H), 7.46 (t, J=7.8Hz, 1H), 7.22 (t, J=5.7H3, 1H), 6.77 (t, J=5.4Hz, 1H), 4.15 (q, J=7.1H3, 2H), 4.05 (d, J=13.2Hz, 2H), 3.70 (dd, J=6.1, 12.0Hz, 2H), 3.46 (dd, J=6.7, 13.1Hz, 2H), 2.63 (t, J=6.1Hz, 2H), 2.6 (m, 2H), 1.67 (d, J=11.2Hz, 2H), 1.54 (m, 2H), 1.45 (s, 9H), 1.26 (t, J=7.1Hz, 3H), 1.1 (m, 2H).

Ester 1-2 (0.27 g) was dissolved in CH$_2$Cl$_2$ (10 ml) and at room temperature trimethylsilyliodide (TMSI) (0.071 mmoles) was added and after 10 minutes stirring starting material was consumed. MeOH (2 ml) was added to quench the reaction and the solvent was removed in vacuo. The residue was dissolved in 1:1:1 THF/MeOH/H₂O (10 ml), lithium hydroxide (0.24 g, 5.68 mmoles) was added, and the reaction mixture was stirred at room temperature. After 1.0 hour the solvent was removed and the residue purified by flash chromatography on silica gel eluting with 9:1:1 EtOH/H₂O/NH₄OH to give 1-3 (R$_f$ 0.3, silica gel, 9:1:1 EtOH/H₂O/NH₄OH, ninhydrin stain).

¹H NMR (300 MHz, CD₃OD) δ 8.22 (s, 1H), 7.95 (m, 2H), 7.54 (m, 1H), 3.60 (s, 2H), 3.4 (m, 6H), 2.90 (m, 2H), 2.47 (s, 2H), 2.0 (s, 2H), 1.8-1.6 (m, 3H), 1.5-1.4 (m, 2H). Mass spectrum (FAB)348 (M+1).

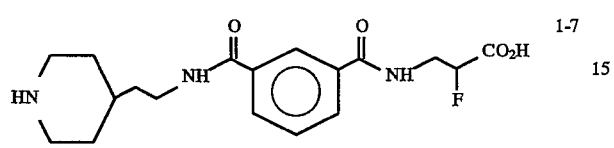

[N-2-(4-Piperidinylethyl)-N'-[3-(2-fluoro)propanoic Acid]-1,3-benzenedicarboxamide (1-7)

This was prepared as described for 1-3, wherein 2-fluoro-β-alanine ethyl ester (American Tokyo Kasai) was used as the C-terminal amino acid component.

¹H NMR (300 MHz, CD₃OD) δ 8.25 (s, 1H), 7.96 (d, J=7.1Hz, 2H), 7.56 (t, J=7.7Hz, 1H), 5.0 (m, 1H), 4.0-3.85 (m, 2H), 3.45 (t, J=6.7Hz, 2H), 3.32 (d, J=11.7Hz, 2H), 2.98 (dt, J=2.8, 12.9Hz, 2H), 2.00 (d, J=14.6Hz, 2H), 1.75 (m, 1H), 1.65 (dd, J=6.8, 13.4Hz, 2H), 1.45 (m, 2H) Mass spectrum (FAB) 366 (M+1).

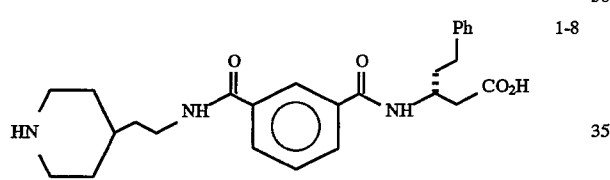

{N-2-(4-Piperidinylethyl)-N'-3-[3(R)-phenethyl-propanoic Acid]}-1,3-benzenedicarboxamide (1-8)

This was prepared as described for 1-3 but using 3-R-phenethyl-β-alanine ethyl ester (the TFA salt of which is prepared according to the procedure of Example 15, page 36, of European Publication 478362) as the C-terminal amino acid component 1-10 had R$_f$ 0.3 (silica gel, 9:1:1 EtOH/H₂O/NH₄OH, ninhydrin stain).

¹H NMR (300 MHz, CD₃OD) δ 8.20 (d, J=1.5Hz, 1H), 7.97 (m, 2H), 7.56 (t, J=7.75Hz, 1H), 7.20 (m, 4H), 7.12 (m, 1H), 4.43 (t, J=6.7Hz, 1H), 3.45 (t, J=6.5Hz, 2H), 3.32 (m, 2H), 2.97 (t, J=12.6Hz, 2H), 2.71 (t, J=8.0Hz, 2H), 2.51 (d, J=5.7Hz, 2H), 1.98 (m, 4H), 1.70 (m, 1H), 1.65 (m, 2H), 1.50 (m, 2H) Mass spectrum (FAB) 452 (M+1)

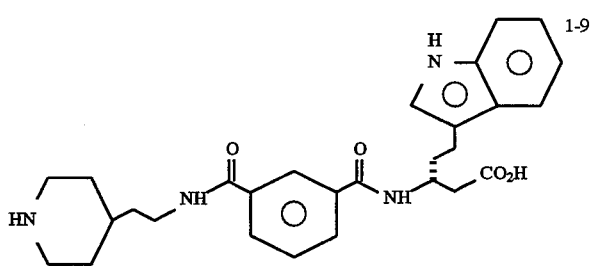

{N-[2-(4-Piperidinylethyl)-N'-3-[3(R)-indolylethyl-propanoic Acid]}-1,3-benzenedicarboxamide (1-9)

This was prepared as described for 1-3 but using 3-R-(indol-3-ylethyl)-β-alanine ethyl ester (the preparation of which is described in European Publication 512,831 at pages 18-19 and 50, identified therein as compound 7a) as the C-terminal amino acid component.

¹H NMR (300 MHz, CD₃OD) δ 8.20 (d, J=1.6Hz, 1H), 7.95 (m, 2H), 7.53 (m, 2H), 7.27 (d, J=8.1Hz, 1H), 7.05-6.90 (m, 3H), 4.50 (t, J=6.2Hz, 1H), 3.43 (t, J=6.7Hz, 2H), 3.30 (m, 2H), 2.90 (m, 4H), 2.54 (d, J=5.9Hz, 2H), 2.10 (dd, J=7.0, 15.5Hz, 2H), 1.91 (d, J=15.0Hz, 2H), 1.6 (m, 3H), 1.4 (m, 2H) Mass spectrum (FAB) 491 (M+1)

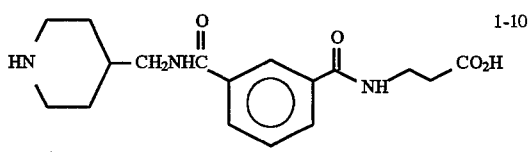

N-(4-Piperidinylmethyl)-N'-(2-carboxyethyl)-1,3-benzenedicarboxamide (1-10)

Treatment of 1-1 with 6-2 and β-alanine ethyl ester as described for 1-2, followed by hydrolysis (LiOH.H₂O) and deprotection (HCl gas) as described for 3-4 provided pure 1-10.

¹H NMR (300 MHz, CD₃OD) δ 0.55 (2H, m), 0.92 (3H, bd), 1.44 (2H, t), 1.92 (2H, t), 2.35 (4H, m), 2.56 (2H, t), 6.50 (1H, t), 6.88 (2H, dt), 7.15 (1H, s).

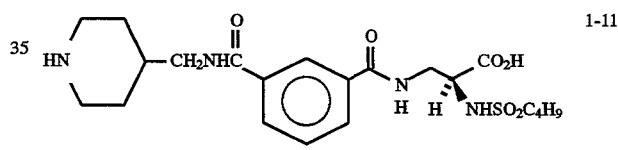

N-(4-Piperidinylmethyl)-N'-[3-(2(S)-n-butylsulfonyl-aminopropionic Acid]-1,3-benzenedicarboxamide (1-11)

Treatment of 1-1 with 6-2 and 9-3 as described for 1-2, followed by hydrolysis (LiOH.H₂O) and deprotection (HCl gas) as described for 3-4 gave pure 1-11, R$_f$ 0.25 (silica, EtOH/NH₄OH/H₂O (10:1:1).

¹H NMR (300 MHz, CD₃OD) δ 0.63 (3H, t), 1.15 (2H, m), 1.36 (2H, m), 1.54 (2H, m), 1.90 (2H, bd), 2.87 (2H, dt), 2.98 (2H, t), 3.25 (2H, d), 3.28-3.45 (3H, m), 3.69 (1H, dd), 3.92 (1H, dd), 7.50 (1H, t), 7.82 (2H, t), 7.98 (1H, s).

SCHEME 2

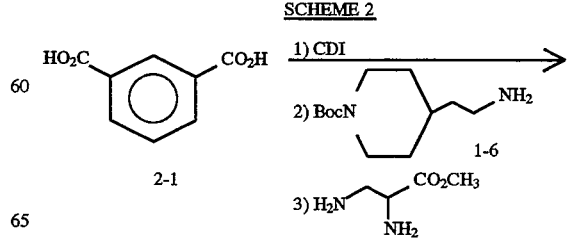

-continued
SCHEME 2

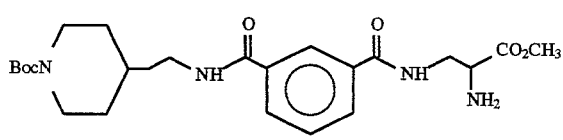

2-2

↓

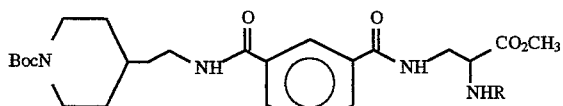

2-3    R = SO₂R¹  or  $\overset{O}{\overset{\|}{C}}R^1$

↓

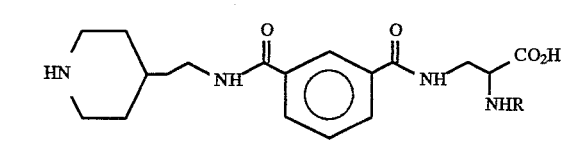

2-4    R = SO₂R¹  or  $\overset{O}{\overset{\|}{C}}R^1$

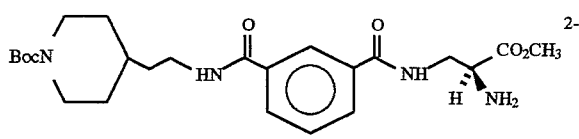

{N-2-(N'-Boc-4-Piperidinylethyl)-N'''-3-[methyl 2(S)
-aminopropanoate]}-1,3-benzenedicarboxamide (2-2)

To a solution of 1,3-benzenedicarboxylic acid (0.27 g, 1.66 mmoles) in 10 ml DMF was added carbonyl diimidazole (CDI) (0.54 g, 3.32 mmoles) at 0° and this was stirred for 1.0 hour. Then, 1-6 (0.38 g, 1.66 mmoles) was added and the resulting solution was stirred for 4.0 hrs. Methyl 2(S), 3-diaminopropionate (9-8) (0.315 g, 1.66 mmoles) and N-methylmorpholine (NMM) (4.98 mmoles) were added and the resulting solution was stirred for 16 hours. The solvent was removed and the residue was dissolved in H₂O, acidified with 10% KHSO₄ solution and extracted with EtOAc. The aqueous phase was adjusted to pH 10 and extracted with EtOAc. Solvent removal provided 2-2 as a gum (0.45 g).

¹H NMR (300 MHz, CDCl₃) δ 8.5 (broad, 2H), 8.28 (s, 1H), 7.92 (m, 2H), 7.54 (m, 1H), 7.44 (t, J=7.7Hz, 1H), 4.0 (m, 2H), 3.8–3.6 (m, 1H), 3.68 (s, 3H), 3.50 (m, 1H), 3.40 (m, 2H), 2.60 (m, 2H), 1.6 (d, J=12.7Hz, 2H), 1.5–1.4 (m, 3H), 1.41 (s, 9H), 1.05 (m, 2H).

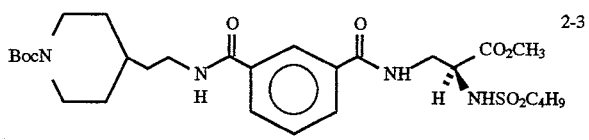

{N-2-(N'-Boc-4-Piperidinylethyl)-N'''-3-[methyl 2(S)
-n-butylsulfonylaminopropanoate]}-1,3-
benzenedicarboxamide (2-3)

To 2-2 (0.45 g, 0.95 mmoles) in CH₂Cl₂ (10 ml) at room temperature was added pyridine (5 mmoles) followed by n-butanesulfonyl chloride (5 mmoles). The reaction mixture was heated at reflux for 8 hours and the solvent was removed. The residue was dissolved in CHCl₃, washed with 10% KHSO₄ solution, brine, dried (Na₂SO₄) and the solvent removed. The resulting residue was purified by flash chromatography on silica gel eluting with 5% MeOH/CHCl₃ to give 2-3.

¹H NMR (300 MHz, CDCl₃) δ 8.10 (s, 1H), 7.86 (t, J=8.1Hz, 2H), 7.66 (t, J=5.9Hz, 1H), 7.38 (t, J=7.7Hz, 1H), 6.84 (t, J=5.5Hz, 1H), 4.42 (d, J=9.0Hz, 1H) 4.37 (m, 1H), 4.02 (d, J=12.5Hz, 2H), 3.95 (m, 1H), 3.76 (s, 3H), 3.70 (m, 1H), 3.25 (m, 2H), 3.00 (t, J=7.9Hz, 2H), 2.66 (t, J=12.1Hz, 2H), 1.70 (m, 2H), 1.60 (d, J=13.6Hz, 2H) 1.43 (s, 9H), 1.40–1.30 (m, 5H), 1.06 (m, 2H), 0.86 (t, J=7.3Hz, 3H).

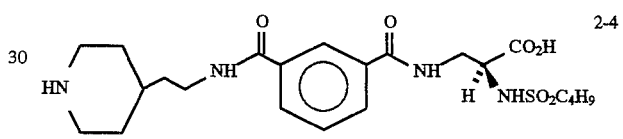

{N-2-(4-Piperidinylethyl)-N'-3-[2(S)-n-
butylsulfonyl-aminopropanoic Acid]}-1,3-
benzenedicarboxamide (2-4)

To 2-3 (0.10 g, 0.167 mmoles) in CH₂Cl₂ (10 ml) at room temperature was added trimethylsilyl iodide (TMSI) (0.35 mmoles). The yellow solution was stirred for 15 min, and then MeOH (5 ml) was added to quench the reaction. The solvent was removed and the residue was dissolved in THF(1)H₂O(1)/MeOH(1) and lithium hydroxide monohydrate (0.070 g, 1.67 mmoles) was added. After stirring for 1 hour the solvent was removed and the residue was purified by flash chromatography on silica gel eluting with EtOH(9)/H₂O(1)/NH₄OH(1) to give pure 2-4.

¹H NMR (300 MHz, D₂O) δ 8.21 (s, 1H), 8.01 (m, 2H), 7.75 (t, J=7.8 Hz, 1H), 3.91 (dd, J=5.1, 8.8Hz, 1H), 3.78 (dd, J=5.1, 12.9Hz, 1H), 3.51 (m, 3H), 3.03 (d, J=11.3Hz, 2H), 2.94 (t, J=8.0Hz, 2H), 2.55 (d, J=12.2Hz, 2H), 1.80-1.55 (m, 7H), 1.40-1.20 (m, 4H), 0.87 (t, J=7.5 Hz, 3H).

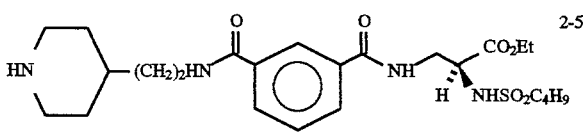

{N-2-(4-Piperidinylethyl)-N'-3-[ethyl 2(S)-n-butyl-
sulfonylaminopropanoate]}-1,3-
benzenedicarboxamide (2-5)

Treatment of 2-3, with HCl gas in EtOAc, as described for 2-4, gave 2-5 as a white solid.

¹H NMR (300 MHz, CD₃OD) δ 0.90 (3H, t), 1.30 (3H, t), 1.4–1.5 (4H, m), 1.6–1.8 (5H, m), 2.05 (2H, d), 3.0 (4H, m), 3.39 (2H, d), 3.45 (2H, m), 3.61 (1H, dd), 3.80 (1H, dd), 4.23 (2H, q), 4.38 (1H, dd), 7.80 (2H, t), 8.0 (2H, d), 8.32 (1H, s).

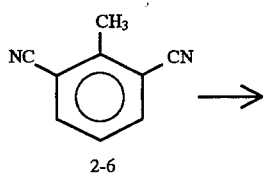

2-6

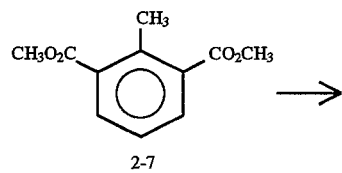

2-7

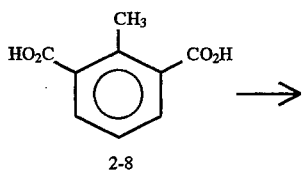

2-8

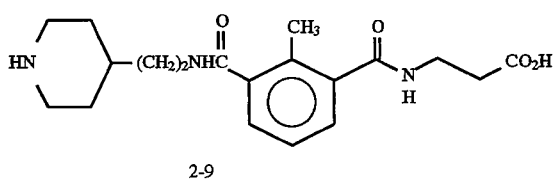

2-9

Dimethyl 2-Methylbenzene-1,3-dicarboxylate (2-7)

A suspension of dicyano compound 2-6 (Aldrich) (10.0 g, 7.04 mmoles) in H$_2$SO$_4$ (75% aqueous, 200 g) was heated at 160° for 4 hours. The cooled reaction mixture was added to H$_2$O and after settling overnight, the solid product was collected. The aqueous phase was extracted with EtOAc and this was concentrated and combined with the solid collected by filtration. This was dissolved in CH$_3$OH, treated with HCl gas at room temperature for 24 hours and concentrated. The residue was taken up in EtOAc, washed with saturated NaHCO$_3$, brine, dried (MgSO$_4$) concentrated and the residue purified by flash chromatography on silica gel eluting with 5% EtOAc/hexanes to give pure 2-7.

$^1$H NMR (300 MHz, CDCl$_3$) δ 2.70 (3H, s), 3.92 (6H, s), 7.29 (1H, m), 7.88 (2H, m).

[N-2-(4-Piperidinyl)ethyl-N'-(2-carboxyethyl)]-2-methyl-1,3-benzenedicarboxamide (2-9)

Diester 2-7 was treated with LiOH.H$_2$O in THF/MeOH/H$_2$O (1:1:1) as described for 3-4 to provide the desired diacid. This was treated with 1-6 and β-alanine ethyl ester as described for 2-2. Hydrolysis and deprotection with HCl gas in EtOAc as described for 3-4 provided 2-9 as a white solid.

$^1$H NMR (300 MHz, CD$_3$OD) δ 1.45 (2H, m), 1.63 (3H, m), 2.03 (2H, bd), 2.36 (3H, s), 2.64 (2H, t), 2.98 (2H, dt), 3.61 (2H, t), 7.35 (3H, m).

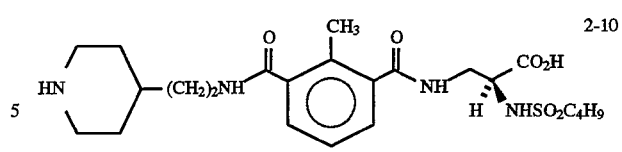

N-2-(4-Piperidinyl)ethyl-N'-3-[2(S)-n-butylsulfonyl-aminopropionic Acid]-2-methyl-1,3-benzenedicarbox-amide (2-10)

This compound was prepared in similar fashion to 2-9 wherein 9-3 was employed to provide 2-10.

$^1$H NMR (300 MHz, CD$_3$OD) δ 0.97 (3H, t), 1.45 (4H, m), 1.44 (2H, m), 1.74 (3H, m), 2.03 (2H, bd), 2.40 (3H, s), 2.99 (2H, dt), 3.10 (2H, t), 3.52 (1H, m), 3.84 (1H, dd), 4.33 (1H, m), 7.30 (1H, t), 7.38 (1H, m), 7.51 (1H, dd).

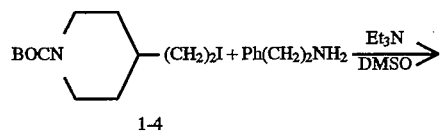

1-4

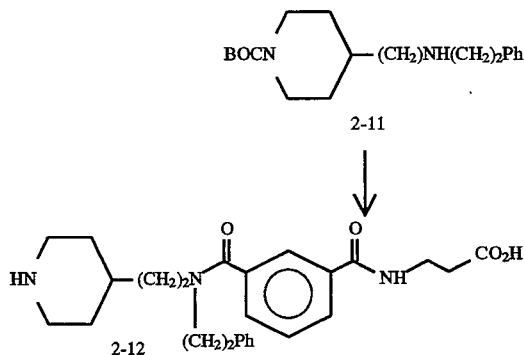

[N-2-(N'-BOC-4-Piperidinyl)ethyl]phenethylamine (2-11)

A solution of phenethylamine (1.07 g, 8.83 moles) and Et$_3$N (1.78 g, 17.6 mmoles) in DMSO (25 ml) was cooled to 0° and treated with 1-4 and this was stirred for 4 hours. The reaction mixture was diluted with EtOAc, washed with saturated NaHCO$_3$, brine, dried (MgSO$_4$) and concentrated. The residue was purified by flash chromatography on silica gel eluting with 2% CH$_3$OH/CHCl$_3$(NH$_3$) to give pure 2-11.

$^1$H NMR (300 MHz, CDCl$_3$) δ 1.10 (2H, m), 1.44 (9H, s), 1.62 (3H, m), 2.67 (4H, m), 2.85 (4H, m), 4.04 (2H, b), 7.22 (2H, m), 7.40 (3H, m).

{N-[2-(4-Piperidinyl)ethyl]-N-(phenethyl)}-N'-(2-carboxyethyl)-1,3-benzenedicarboxamide (2-12)

This compound was prepared in similar fashion to 2-9 wherein 2-11 and β-alanine ethyl ester were used as the amine components. Hydrolysis (LiOH.H$_2$O) and deprotection (HCl gas in EtOAc) as described for 3-4 provided 2-12 as a white solid.

$^1$H NMR (300 MHz, CD$_3$OD) δ 0.80 (2H, m), 1.00 (2H, m), 1.15 (1H, m), 2.13 (2H, m), 2.32 (2H, m), 2.62 (3H, m), 3.24 (2H, m), 3.35 (1H, m), 6.54 (1H, b), 6.82 (1H, b), 6.93 (2H, m), 7.05 (1H, bd), 7.19 (1H, bt), 7.45 (1H, bs), 7.57 (1H, bd).

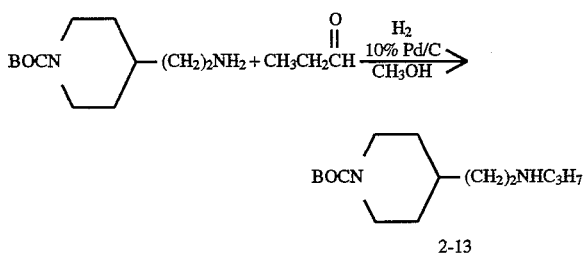

[N-2-(N'-BOC-4-Piperidinyl)ethyl]propylamine (2-13)

A solution of 2-(N-BOC-4-piperidinyl)ethylamine (1-6) (1.0 g, 4.39 mmoles) in $CH_3OH$ (5 ml) was treated with propionaldehyde (4.50 mmoles) and 10% Pd/C (0.25 g) and the resulting suspension was hydrogenated at 1 atmosphere for 20 hours. The catalyst was removed by filtration, the solution concentrated and the residue purified by flash chromatography on silica gel eluting with 2% $CH_3OH$/$CHCl_3(NH_3)$. $R_f$ 0.4 (silica, 10% $CH_3OH$/$CHCl_3(NH_3)$).

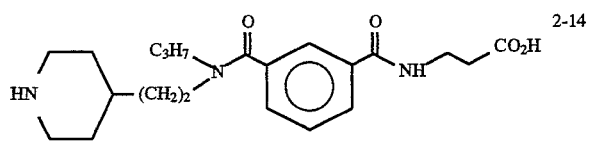

N-[2-(4-Piperidinyl)ethyl-N-propyl]-N'-(2-carboxyethyl)-1,3-benzenedicarboxamide (2-14)

This compound was prepared in similar fashion to 2-9 wherein 2-13 and β-alanine ethyl ester were used as the amine components. Hydrolysis ($LiOH.H_2O$) and deprotection (HCl gas in EtOAc as described for 3-4 gave 2-14.

$^1$H NMR (300 MHz, $CD_3OD$) δ 1.02 (3H, t), 1.28 (2H, m), 1.46 (3H, m), 1.68 (4H, m), 3.20 (4H, m), 3.48 (2H, t), 3.62 (4H, m), 7.52 (1H, d), 7.59 (1H, t), 7.88 (1H, bs), 7.98 (1H, d).

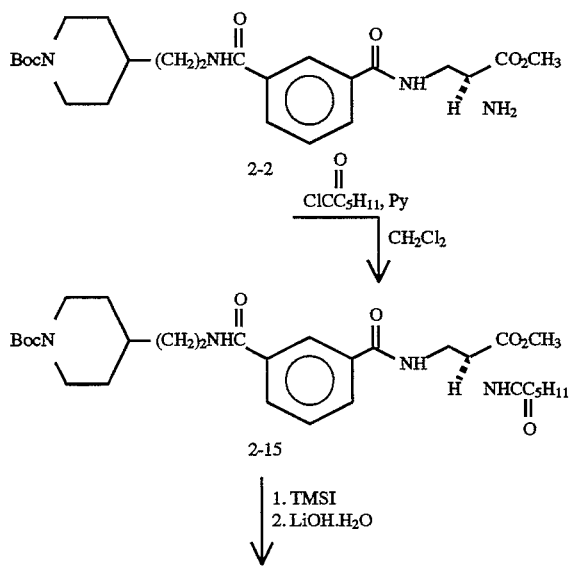

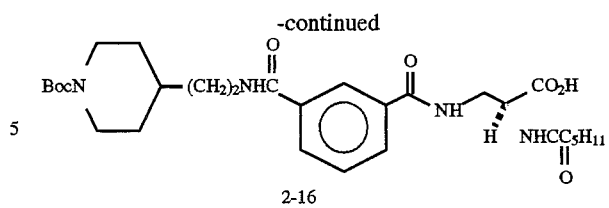

N-[2-(N'-Boc-4-Piperidinyl)ethyl]-N"-[3-(methyl 2 (S)-hexanoylaminopropionate)]-1,3-benzenedicarboxamide (2-15)

A solution of 2-2 (0.6 g, 1.26 mmoles) in $CH_2Cl_2$ (15 ml) was treated with pyridine (3.78 mmoles), cooled to 0°, and then treated with hexanoyl chloride (3.78 mmoles) and the solution was then stirred at ambient temperature for 4 hours. The solvent was removed, and the residue dissolved in 10% $KHSO_4$ solution to pH 2–3, extracted with $CH_2Cl_2$ and this was washed with brine, dried ($MgSO_4$) and concentrated to give 2-15. $R_f$ 0.65 (silica, 10% $MeOH/CHCl_3(NH_3)$).

N-2-(4-Piperidinyl)ethyl-N'-[3-(2(S)-hexanoylamino-propionic Acid)]-1,3-benzenedicarboxamide (2-16)

A solution of 2-15 (0.545 g, 0.95 mmoles) in $CH_2Cl_2$ (50 ml) was treated at room temperature with TMSI (2.9 mmoles) and after stirring for 15 minutes, the reaction was quenched with 20 ml $CH_3OH$. The solvent was removed and the residue was dissolved in $THF/MeOH/H_2O$ (1:1:1) (45 ml) and treated with $LiOH.H_2O$ (0.42 g, 10 mmoles) with stirring for 0.5 hr. Solvent removal gave a residue that was purified by flash chromatography on silica gel eluting with $EtOH/H_2O/NH_4OH$ (9:1:1) to give pure 2-16.

$^1$H NMR (300 MHz, $CD_3OD$) δ 0.5 (3H, t), 0.92 (5H, m), 1.05–1.45 (6H, m), 1.70 (2H, bd), 1.91 (2H, t), 2.65 (2H, t), 2.98 (4H, m), 3.06 (2H, bd), 3.14 (2H, t), 3.42 (2H, m), 7.23 (1H, t), 7.63 (2H, d), 7.90 (s).

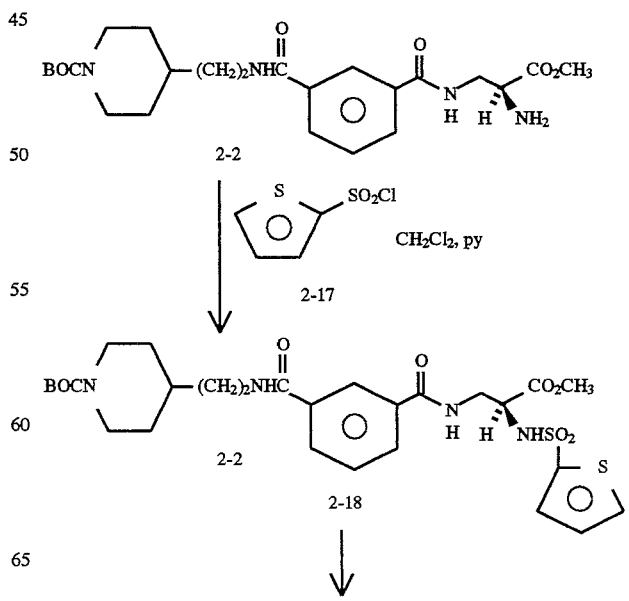

-continued

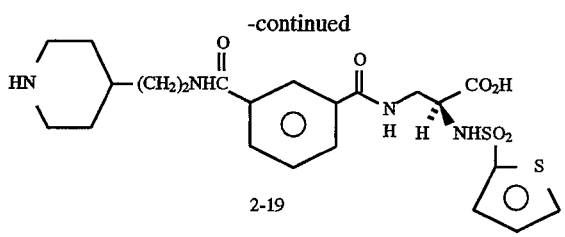

2-19

[N-2-(N'-BOC-4-Piperidinyl)ethyl]-N"-3-[methyl 2(S)-thien-2-ylsulfonylaminopropionate]-1,3-benzenedicarboxamide (2-18)

A solution of 2-2 (0.34 g, 0.71 mmoles) in $CH_2Cl_2$ (5 ml) at room temperature was treated with pyridine (2.12 mmoles) followed by 2-thiophenesulfonylchloride (Aldrich) (0.32 g, 2.12 mmoles). After stirring for 3 hours, the solvent was removed and the residue was taken up in $CH_2Cl_2$ washed with $NaHCO_3$, 10% $KHSO_4$, brine, dried ($MgSO_4$) and concentrated. The residue was purified by flash chromatography on silica gel eluting with 5% $MeOH/CHCl_3$ to provide pure 2-18, $R_f$ 0.45 (silica, 10% $MeOH/CHCl_3(NH_3)$).

[N-2-(4-Piperidinyl)ethyl]-N'-[3-2(S)-thien-2-yl-sulfonylaminopropionic Acid]-1,3-benzenedicarboxamide (2-19)

Treatment of 2-18 with $LiOH.H_2O$ followed by deprotection with HCl gas in EtOAc as described for 3-4 gave 2-19 as a white solid. $R_f$ 0.23 (silica, EtOH, $NH_4OH/H_2O$ (10:1:1)).

$^1$H NMR (300 MHz, $CD_3OD$) δ 1.40 (2H, m), 1.66 (2H, m), 1.77 (1H, m), 2.04 (2H, bd), 3.00 (2H, t), 3.50 (2H, t), 3.65 (2H, m), 3.77 (2H, dd), 3.90 (2H, dd), 7.10 (1H, m), 7.59 (2H, m), 7.72 (1H, d), 7.98 (2H, m), 8.26 (1H, s).

Preparation of Dimethyl 4-Methylbenzene-1,3-dicarboxylate (2-20)

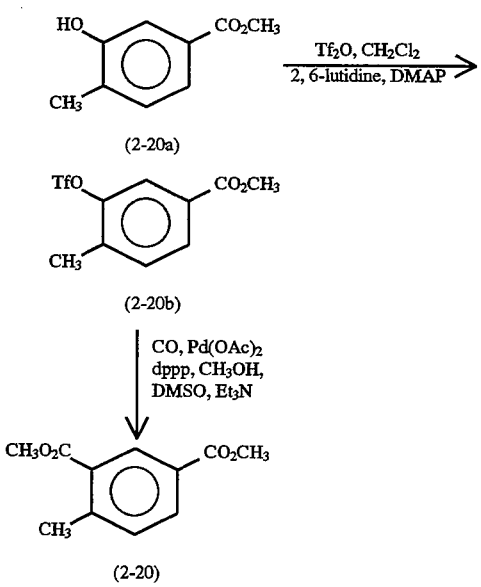

Methyl 4-Methyl-3-trifluoromethanesulfonyloxybenzoate (2-20b)

A solution of methyl 4-methyl-3-hydroxybenzoate (2-20a) (20.0 g, 0.12 moles) [prepared from the corresponding carboxylic acid (Aldrich) by treatment with a methanolic solution of HCl gas] in $CH_2Cl_2$ (900 ml) was cooled to –40° C. and treated successively with 2,6-lutidine (0.18 moles), DMAP (2.9 g, 0.024 moles) and trifluoromethylsulfonyl anhydride (0.18 moles). The cooling bath was then removed and the resulting mixture was stirred at ambient temperature for 2.0 hours. The solvent was then removed and the residue was purified by flask chromatography on silica eluting with hexane(8)/-EtOAc(2) to provide pure 2-20b, $R_f$ 0.35.

$^1$H NMR (300 MHz, $CDCl_3$) δ 2.18 (3H, s), 3.85 (3H, s), 7.30 (1H, d), 7.84 (1H, s), 7.90 (1H, d).

Dimethyl 4-Methylbenzene-1,3-dicarboxylate (2-20)

A solution of 2-20b (30.0 g, 0.121 moles) in methanol/300 ml was treated successively with DMSO (180 ml), triethylamine (0.278 moles), palladium acetate (0.807 g, 3.6 mmoles) and dppp (1.48 g, 3.6 mmoles) as the reaction turned to a clear dark brown solution. Carbon monoxide was then bubbled through the reaction mixture for 3 minutes and the resulting mixture was heated at reflux, while continuing to bubble CO. After refluxing for 4 hours the reaction mixture was concentrated and the resulting brown oil was purified by flask chromatography on silica gel eluting with hexane(90)/EtOAc(10) to provide pure 2-20.

$^1$H NMR (300 MHz, $CDCl_3$) δ 2.69 (3H, s), 3.95 (3H, s), 3.96 (3H, s), 7.37 (1H, d), 8.09 (1H, dd), 8.60 (1H, d).

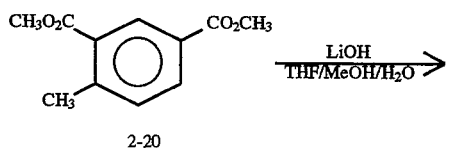

2-20

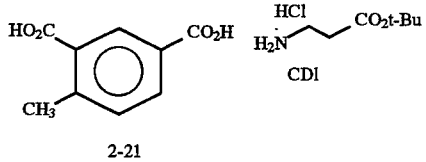

2-21

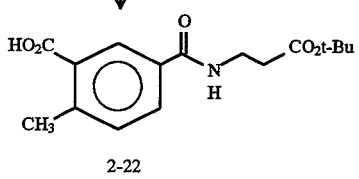

2-22

BOP/$CH_3CN$

BOCN⟨⟩—$(CH_2)_2NH_2$ 1-6

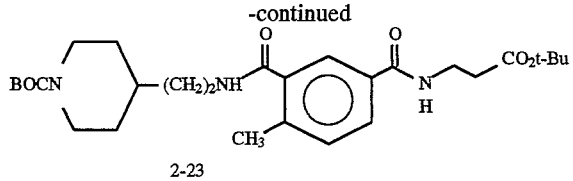

2-23

↓ HCl/EtOAc

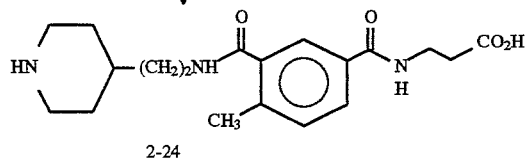

2-24

4-Methyl-1,3-benzenedicarboxylic Acid (2-21)

A solution of 2-20 (1.5 g, 7.2 mmoles) in THF/MeOH/H$_2$O (1:1:1) (36 ml) at room temperature was treated with LiOH.H$_2$O (1.5 g, 36 mmoles). After stirring for 3 hours, the solvent was removed and the residue acidified with 1N HCl. This was extracted with EtOAc, and the extract was dried (MgSO$_4$) and concentrated to give 2-21.

$^1$H NMR (300 MHz, CD$_3$OD) δ 2.65 (3H, s), 7.40 (1H, d), 8.03 (2H, d), 8.56 (1H, s).

4-Methyl-3-carboxy-N-2-(t-butyloxycarbonylethyl)-benzenecarboxamide (2-22)

2-21 (0.4 g, 2.22 mmoles) in DMF (6 ml) was treated at room temperature with CDI (4.44 mmoles). After stirring for 10 minutes, β-alanine t-butylester HCl (Bachem) (0.20 g, 1.11 mmoles) was added and the reaction mixture was stirred for 18 hours. The solvent was removed and the residue acidified to pH 2–3 with 10% KHSO$_4$ solution extracted with EtOAc and this was dried (MgSO$_4$) and concentrated. The residue was purified by flash chromatography on silica gel eluting with CH$_2$Cl$_2$/MeOH/HOAc (9/0.25/0.25).

4-Methyl-3-{N-[2-(N'-Boc-4-piperidinyl)ethyl]-N"-2-(t-butyloxycarbonylethyl)}-1,3-benzenedicarboxamide (2-23)

A solution of 2-22 (0.33 g, 1.07 mmoles) in CH$_3$CN (5 ml) was treated with 1-6 (0.38 g, 1.6 mmoles) at room temperature to give a clear solution. This was treated with NMM (2.7 mmoles) followed by BOP (1.6 mmoles) and the reaction mixture was stirred for 18 hours. This was then diluted with EtOAc, washed with H$_2$O, 10% KHSO$_4$, saturated NaHCO$_3$, brine, dried (MgSO$_4$) and concentrated. The residue was purified by flash chromatography on silica gel eluting with 60% EtOAc/hexanes to give pure 2-23. R$_f$ 0.26 (silica, 60% EtOAc/hexanes.

4-Methyl-[2-(4-piperidinyl)ethyl]-N'-2-(carboxyethyl)-1,3-benzenedicarboxamide (2-24)

A solution of 2-23 (0.23 mmoles) in EtOAc (5 ml) was treated with HCl gas as described for 3-4 to give 2-24 as a white solid.

$^1$H NMR (300 MHz, D$_2$O) δ 1.12 (2H, t), 1.33 (2H, m), 1.52 (2H, m), 1.60 (1H, m), 1.90 (2H, bd), 2.26 (3H, s), 2.58 (2H, t), 2.88 (2H, bt), 3.32 (4H, m), 3.52 (2H, t), 7.29 (1H, d), 7.52 (1H, s), 7.59 (1H, dd).

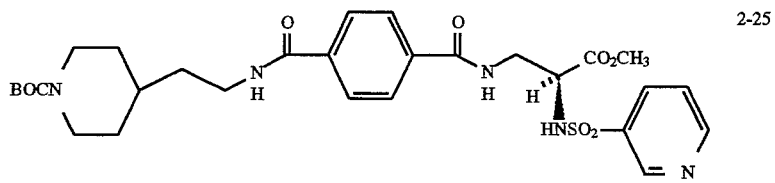

{N-2-(N'-BOC-4-piperidinylethyl)-N"-3-[methyl 2(S)-(3-pyridylsulfonylamino)propionate]}-1,4-benzene Dicarboxamide (2-25)

Compound 2-25 was prepared using the same procedure as for 2-2, utilizing 1-6, terephthalic acid and 9-13. R$_f$ 0.26 (60% Acetone/Hexane.

$^1$H NMR (300 MHz, CDCl$_3$) δ 9.1 (s, 1H), 8.8 (d, J=3Hz, 1H), 8.2 (m, 1H), 7.9 (m, 1H), 7.7 (s, 4H), 7.5 (m, 1H), 7.4 (m, 1H), 4.4 (m, 1H), 4.1 (bd, 2H), 3.9 (s, 2H), 3.7 (s, 3H), 3.6 (m, 2H), 2.8 (m, 2H), 1.9-1.6 (m, 5H), 1.6 (s, 9H), 1.2 (m, 2H).

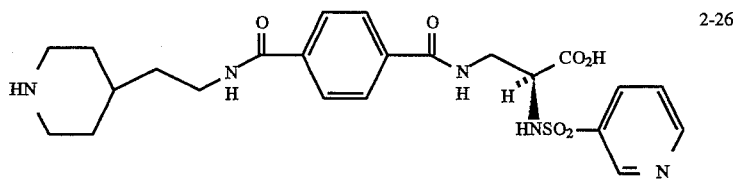

{N-2-(4-Piperidinylethyl)-N'-3-[2(S)-(3-pyridylsulfonylamino)propanoic Acid]-1,4-benzenedicarboxamide (2-26)

Compound 2-25 was treated with 6N HCl at room temperature for 16 hours, then concentrated to yield 2-26 as a white solid. R$_f$ 0.27 (9:1:1 EtOH/H$_2$O/NH$_4$OH).

$^1$NMR (300 MHz, D$_2$O) δ 9.1 (s, 1H), 8.7 (m, 2H), 7.9 (dd, J=6, 8Hz, 1H), 7.8 (d, J=8.5, 2H), 7.7 (d, J=8.5, 2H), 4.5

(dd, J=4, 9Hz, 1H), 3.8 (dd, J=4, 14Hz, 1H), 3.5 (dd, J=9, 14Hz, 1H), 3.4 (m, 4H), 3.0 (m, 2H), 1.95 (bd, 2H), 1.8-1.6 (m, 3H), 1.4 (m, 2H).

4.3 (t, 1H), 3.8 (m, 2H), 3.6 (s, 3H), 3.45 (m, 2H), 3.25 (bs, 2H), 2.8 (s, 3H), 1.6 (bs, 4H), 1.45 (s, 9H).

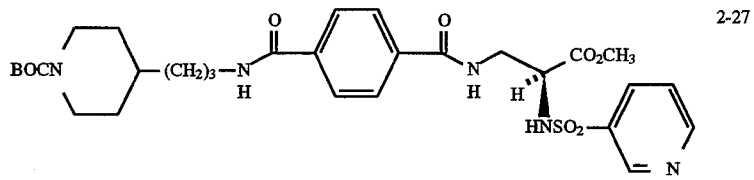

2-27

{N-3-(N'-BOC-4-piperidinylpropyl)-N"-3-[methyl 2 (S)-(3-pyridylsulfonylamino)propionate]}-1,4-benzene Dicarboxamide (2-27)

Compound 2-27 was prepared using the same procedure as for 2-25, utilizing 9-13, terephthalic acid and 3-(4-N-BOC-piperidinyl) propylamine (Compound 10-1, page 50, line 2, and page 51, lines 53–54, of European Publication 540,334). $R_f$ 0.26 (60% Acetone/Hexanes)

$^1$H NMR (300 MHz, CDCl$_3$) δ 9.0 (s, 1H), 8.7 d, (1H), 8.1 (m, 1H), 7.6 (s, 4H), 7.4 (dd, 1H), 7.0 (bt, 1H), 4.3 (m, 1H), 4.0 (bd, 2H), 3.8 (s, 3H), 3.4 (m, 2H), 2.6 (bt, 2H), 1.6 (bd, 4H), 1.4 (s, 9H), 1.3-1.2 (m, 3H), 1.1 (m, 2H).

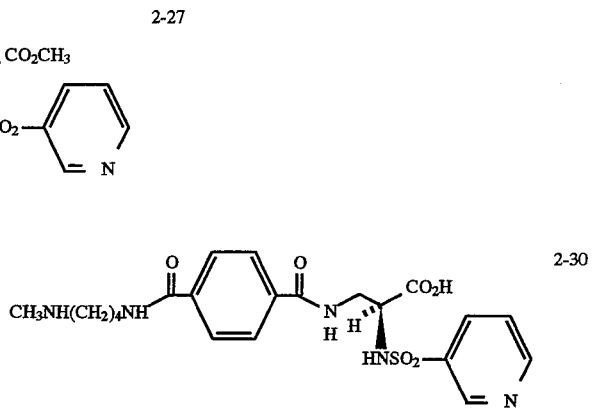

2-30

4-[(4-(N-Methylaminobutyl)aminocarbonyl]benzoyl-2(S)-3-pyridylsulfonylamino-β-alanine (2-30)

Treatment of 2-29 with 6N HCl, followed by concentration and column chromatography (SiO$_2$, 9:1:1 EtOH/H$_2$O/NH$_4$OH) gave 2-30 as a white solid.

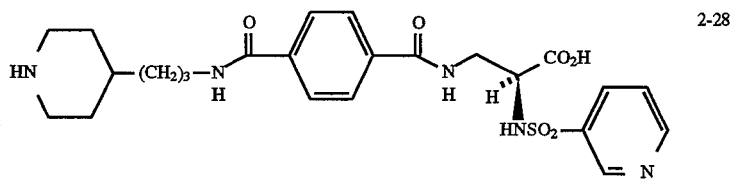

2-28

{N-3-(4-Piperidinylpropyl)-N'-3-[2(S)-3-pyridylsulfonylaminopropanoic Acid]-1,4-benzendicarboxamide (2-28)

Compound 2-28 was prepared using the same procedure as described for 2-26. $R_f$ 0.27 (9:1:1 EtOH/H$_2$O/NH$_4$OH).

$^1$H NMR (300 MHz, D$_2$O) δ 9.2 (s, 1H), 8.7 (m, 2H), 7.9 (m, 1H), 7.7 (d, J=8.5Hz, 1H), 7.65 (d, J=8.5Hz, 1H), 4.45 (dd, J=4, 9Hz, 1H), 3.8 (dd, J=4, 14Hz, 1H), 3.5 (dd, J=9, 14Hz, 1H), 3.4 (m, 4H), 3.0 (m, 2H), 1.9 (bd, 2H), 1.6 (m, 3H), 1.4 (m, 4H).

$^1$H NMR (300 MHz, D$_2$O) δ 8.7 (s, 1H), 8.15 (d, 1H), 8.0 (d, 1H), 7.75 (d, 2H), 7.6 (d, 2H), 7.2 (m, 1H), 3.7 (dd, 1H), 3.6 (dd, 1H), 3.4 (m, 2H), 3.2 (dd, 1H), 2.5 (m, 2H), 2.25 (s, 3H), 1.7-1:4 (m, 4H).

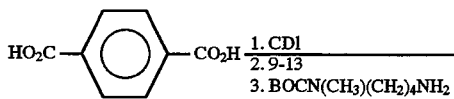

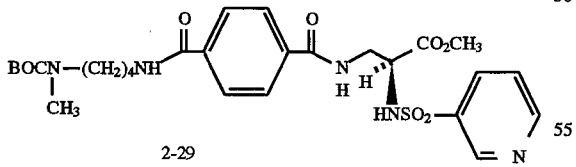

2-29

4-[4-(N-Boc-N-Methylamino)butylaminocarbonyl]benzoyl-2(S)-3-pyridylsulfonylamino-β-alanine Methyl Ester (2-29)

Treatment of 1,4-benzene dicarboxylic acid (Aldrich) with CDI, 9-13 and 4-(N-t-butyloxycarbonyl methyl amino) butylamine (Syn. Comm., 1992, 22, 2357) as described for 1-2 gave 2-29.

$^1$H NMR (300 MHz, CDCl$_3$) δ 9.0 (s, 1H), 8.71 (d, 1H), 8.11 (m, 1H), 7.8-7.6 (m, 4H), 7.58 (m, 1H), 7.35 (dd, 1H),

SCHEME 3

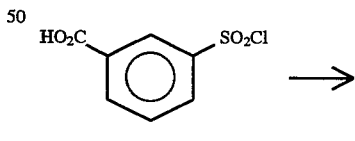

3-1

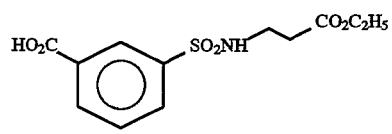

3-2

-continued
SCHEME 3

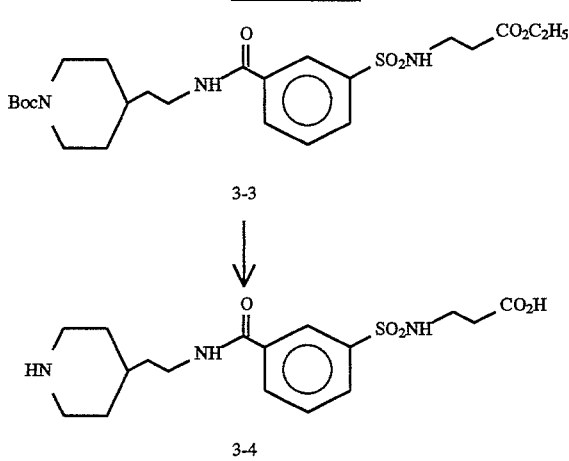

3-[(2-Carboethoxyethyl)aminosulfonyl]benzoic Acid (3-2)

To a solution of 3-chlorosulfonylbenzoic acid (3-1) (Maybridge Chemicals) (1.10 g, 5 mmoles) and β-alanine ethyl ester (0.85 g, 5.5 mmoles) in CHCl₃ (20 ml) at room temperature was added triethylamine (1.52 g, 15 mmoles). After stirring for 3 hrs the solvent was removed, the residue was taken up in EtOAc, washed with H₂O, 10% KHSO₄ solution, H₂O, brine and dried (Na₂SO₄). Solvent removal gave a residue that was purified by flash chromatography on silica gel eluting with CHCl₃(97)/MeOH(3) to give pure 3-2.

¹H NMR (300 MHz, CDCl₃) δ 1.24 (3H, t), 2.55 (2H, t), 3.23 (2H, q), 4.25 (2H, q), 6.66 (1H, t), 7.65 (1H, t), 8.12 (1H, d), 8.30 (1H, d), 8.60 (1H, s).

3-[(2-Carboethoxyethyl)aminosulfonyl]-N-[N'-2-(Boc-4-piperidinylethyl)]benzamide (3-3)

To a solution of 3-2 (0.3 g, 1 mmoles) and 1-6 (0.228 g, 1 mmoles) in acetonitrile (15 ml) was added BOP (0.53 g, 1.2 mmoles) and triethylamine (0.36 g, 3.6 mmoles) at room temperature. After stirring for 48 hours the solvent was removed and the residue was taken up in EtOAc and this was washed with H₂O, 10% KHSO₄ solution, H₂O, saturated NaHCO₃ solution, brine and dried (Na₂SO₄). Solvent removal provided a residue that was triturated with Et₂O to give 3-3 as a viscous, yellow residue.

¹H NMR (300 MHz, CDCl₃) δ 1.0–1.22 (2H, m), 1.22 (3H, t), 1.45 (9H, bs), 1.45–1.80 (5H, m), 2.52 (2H, t), 2.65 (2H, bt) 3.22 (2H, m), 3.49 (2H, m), 3.95–4.20 (4H, m), 5.69 (1H, bt), 6.80 (1H, bt), 7.60 (1H, t) 7.98 (1H, d), 8.06 (1H, d), 8.23 (1H, s).

3-[(2-Carboxyethyl)aminosulfonyl]-N-[2-(4-piperidinyl-ethyl)]-benzamide (3-4)

3-3 (0.44 g, 0.86 mmoles) was dissolved in 15 ml of THF(1)/MeOH(1)/H₂O(1), treated with LiOH.H₂O (3.0 mmoles), and this was stirred at room temperature for 16 hrs. The solvent was then removed and the residue was taken up in 100 ml/H₂O and this acidified to pH 2–3 with 10% KHSO₄ soln. This solution was extracted with EtOAc and the combined extracts were washed with brine and dried (Na₂SO₄). Solvent removal gave a residue that was purified by flash chromatography on silica gel eluting with CHCl₃(95)/MeOH(5) to give the desired acid as an oil.

¹H NMR (300 MHz, CDCl₃) δ 1.0–1.21 (2H, m), 1.46 (9H, bs), 1.46–1.78 (5H, m), 2.53 (2H, t), 2.68 (2H, bt), 3.20 (2H, m), 3.50 (2H, bq), 4.05 (2H, bd), 6.08 (1H, b), 6.89 (1H, bt), 7.60 (1H, t), 8.01 (1H, d), 8.05 (1H, d), 8.27 (1H, s).

This acid was dissolved in EtOAc (30 ml), cooled to –25° C. and treated by bubbling gaseous HCl through the solution for 20 minutes. The reaction mixture was then stoppered and stirred at 0° C. for 1.0 hr. The solvent was removed and the resulting solid was triturated with EtOAc (30 ml) to give crude 3-4 as a white solid. This was purified by flash chromatography on silica gel eluting with H₂O(1)/NH₄OH (1) to give pure 3-4.

¹H NMR (300 MHz, CD₃OD) δ 1.30–1.53 (2H, m), 1.53–1.82 (3H, m), 2.0 (2H, bd), 2.30 (2H, t), 2.95 (2H, dt), 3.10 (2H, t), 3.35 (2H, bd), 3.48 (2H, t), 7.68 (1H, t), 8.01 (1H, d), 8.05 (1H, d), 8.30 (1H, s).

SCHEME 4

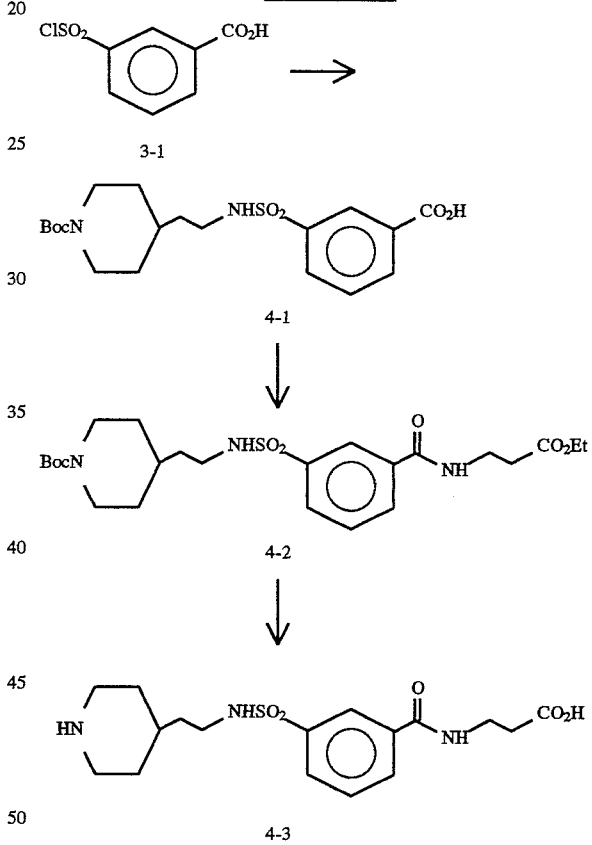

3-[2-(N-Boc-Piperidin-4-yl)ethylaminosulfonyl] benzoic Acid (4-1)

A solution of 2-(N-Boc-4-piperidinyl)ethyl-amine (1-6) (0.45 g, 2.0 mmoles) in CHCl₃ (20 ml) was treated with added triethylamine (0.405 g, 4.0 mmoles) followed by 3-chlorosulfonylbenzoyl chloride (3-1) (0.44 g, 2.0 mmoles) and the resulting solution was stirred at room temperature for 16 hours. The solvent was then removed and the residue was taken up in EtOAc and washed with H₂O, 10% KHSO₄ solution, brine and dried (Na₂SO₄). Solvent removal provided a residue that was purified by flash chromatography on silica gel eluting with CHCl₃(95)/MeOH(5) to give pure 4-1.

¹H NMR (300 MHz, CDCl₃) δ 0.98–1.2 (2H, m), 1.46 (9H, bs), 1.3–1.7 (5H, bd), 2.64 (2H, dt), 3.04 (2H, m), 4.05

(2H, bd), 5.04 (1H, bs), 7.65 (1H, t), 8.12 (1H, d), 8.31 (1H, d), 8.6 (1H, s).

3-[2-(N-Boc-4-Piperidinyl)ethylaminosulfonyl]-N'-[(2-carboethoxy)ethyl]benzamide (4-2)

A solution of 4-1 (0.7 g, 1.7 mmoles), β-alanine ethyl ester hydrochloride (0.26 g, 1.7 mmoles), BOP (0.90 g, 2.04 mmoles) in CH₃CN (15 ml) was treated with 0.62 g (6.12 mmoles) triethylamine and the resulting solution was stirred at room temperature for 16 hours. The solvent was removed and the residue was dissolved in EtOAc. This was washed with H₂O, 10% KHSO₄ solution, H₂O, saturated NaHCO₃ solution, brine and dried (Na₂SO₄). Solvent removal provided a residue that was purified by flash chromatography on silica gel eluting with CHCl₃ (96)/MeOH (4) to give pure 4-2.

¹H NMR (300 MHz, CDCl₃) δ 0.91–1.12 (2H, m), 1.27 (3H, t), 1.27–1.62 (5H, m), 1.45 (9H, bs), 2.49–2.72 (4H, m), 2.9–3.05 (2H, m), 3.72 (2H, q), 4.02 (2H, bd), 4.15 (2H, q), 5.35 (1H, bs), 7.122 (1H, bt), 7.59 (1H, t), 7.99 (2H, d), 8.3 (1H, s).

3-[2-(4-Piperidinyl)ethylaminosulfonyl]-N-[(2-carboxyethyl)]benzamide (4-3)

4-2 (0.17 g, 4.05 mmoles) was dissolved in 15 ml of THF(1)/MeOH(1)/H₂O(1), treated with LiOH.H₂O (12 mmoles), and this was stirred for 16 hours. The solvent was then removed and the residue was diluted with H₂O (100 ml) and extracted with Et₂O. The aqueous phase was adjusted to pH 2–3 with 10% KHSO₄ and extracted with EtOAc. The organic phase was washed with brine, dried (Na₂SO₄) and the solvent removed to give the desired acid. $R_f$ 0.15 (silica gel, CHCl₃(95)/MeOH (5)).

¹H NMR (300 MHz, CDCl₃) δ 0.87–1.1 (2H, m), 1.22–1.55 (5H, m), 1.44 (9H, bs), 2.55 (2H, bt), 2.75 (2H, m), 2.98 (2H, m), 3.72 (2H, m), 4.00 (2H, bd), 5.42 (1H, bs), 7.62 (1H, t), 7.65 (1H, bs), 8.00 (1H, d), 8.17 (1H, d), 8.34 (1H, s).

This acid (0.48 g, 1.0 mmole) was dissolved in EtOAc and treated with HCl gas as described for 3-4. Trituration of crude product with EtOAc gave pure 4-3, $R_f$ 0.35 (silica gel/EtOH(9)/H₂O(1).

¹H NMR (300 MHz, CD₃OD) δ 1.20–1.39 (2H, m), 1.45 (2H, q), 1.72 (1H, m), 1.88 (2H, bd), 2.65 (2H, t), 2.74–3.03 (4H, m), 3.35 (2H, bd), 3.64 (2H, q), 7.68 (1H, t), 8.02 (2H, m), 8.28 (1H, s), 8.80 (1H, bt)

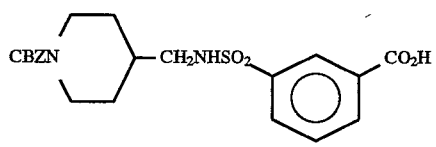

3-[N-CBZ-4-Piperidinyl)methylaminosulfonyl]benzoic Acid (4-4)

4-4 was prepared as described for 4-1 wherein (N-CBZ-piperidin-4-yl)methylamine 8-3 was employed. 4-1 had ¹H NMR (300 MH₃, CD₃OD) δ 0.95–1.13 (2H, m), 1.52–1.75 (3H, m), 2.72 (2H, d), 2.60–2.90 (2H, m), 4.10 (2H, d), 5.09 (2H, s), 7.2–7.4 (5H, m), 7.66 (1H, t) 8.02 (1H, d), 8.22 (1H, d), 8.44 (1H, d)

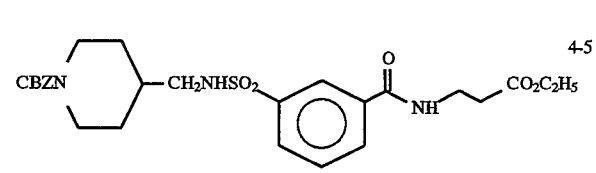

3-[(N-CBZ-4-Piperidinyl)methylaminosulfonyl]-N'-[(2-carboethoxy)ethyl]benzamide (4-5)

4-5 was prepared as described for 4-2.

¹H NMR (300 MHz, CDCl₃) δ 0.96–1.16 (2H, m), 1.26 (2H, t), 1.52–1.73 (3H, bd), 2.65 (2H, t), 2.60–2.70 (2H, m), 2.72 (2H, t), 3.72 (2H, q), 4.13 (4H, bq), 5.09 (2H, s), 5.30 (1H, bt), 7.17 (1H, bt), 7.25–7.45 (5H, m), 7.59 (1H, t), 7.97 (2H, d), 8.28 (1H, s)

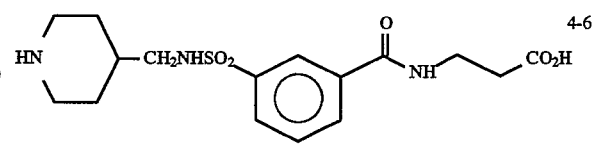

3-[(4-Piperidinyl)methylaminosulfonyl]-N-[(2-carboxyethyl)]benzamide (4-6)

4-6 was prepared from 4-5 as described for 4-3.

¹H NMR (300 MHz, CD₃OD) δ 1.25–1.50 (2H, m), 1.74 (1H, m), 1.88 (2H, bd), 2.49 (2H, t), 2.80–2.96 (4H, m), 3.34 (2H, bd), 3.63 (2H, t), 7.65 (1H, t), 7.98 (1H, d), 8.04 (1H, d), 8.27 (1H, s).

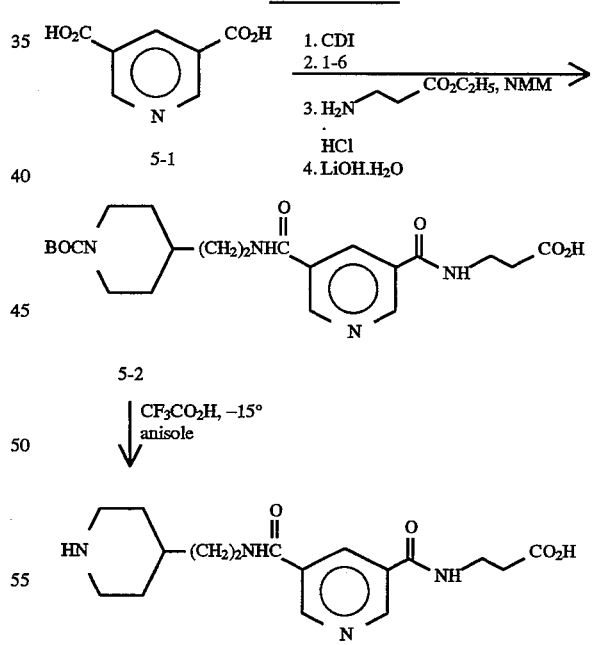

N-[(2-(N-Boc-4-Piperidinyl)ethyl]-N'-[(2-carboxyethyl]-3,5-pyridinedicarboxamide (5-2)

A solution of 3,5-pyridinedicarboxylic acid (Aldrich) (5-1) (0.74 g, 4.4 mmoles) in DMF (40 ml) at room temperature was treated with carbonyldiimidazole (CDI) (1.4 g, 8.8 mmoles) and after 1 hr, 1-6 (4.4 mmoles) was added. Then, β-alanine ethyl ester hydrochloride (0.67 g, 4.4 mmoles) was added followed by N-methylmorpholine (NMM) (13.2 mmoles) and the resulting solution was stirred at room temperature for 16 hrs. The reaction was diluted with EtOAc and washed with H$_2$O, 10% KHSO$_4$ solution, brine and dried (Na$_2$SO$_4$). Solvent removal provided the desired dicarboxamide as an oil, which was submitted without further purification to the next reaction.

This oil was dissolved in THF(1)/MeOH(1)/H$_2$O(1) (15 ml) and LiOH (21 mmoles) was added. After stirring at room temperature for 1 hr the reaction mxt was diluted with EtOAc/H$_2$O. The aqueous phase was separated and adjusted to pH 5 with 10% KHSO$_4$ soln and extracted with EtOAc. The organic phase was washed with H$_2$O, brine and dried (Na$_2$SO$_4$). Solvent removal gave the desired acid (5-2) as a white solid.

$^1$H NMR (300 MHz, CD$_3$OD) δ 8.99 (s, 2H), 8.52 (s, 1H), 4.95 (d, 2H), 3.58 (t, 2H), 3.40 (m, 2H), 2.75-2.60 (m, 2H), 2.58 (t, 2H), 1.7 (d, 2H), 1.5 (m, 3H), 1.37 (s, 9H), 1.05 (m, 2H).

N-[2-Piperidin-4-yl)ethyl]-N'-[(2-carboxy)ethyl]-3,5-pyridinedicarboxamide (5-3)

5-2 (0.30 g, 0.67 mmoles) was dissolved in CH$_2$Cl$_2$ and treated at −15° with anisole (1.5 mmoles) and trifluoroacetic acid (3 ml). After stirring for 0.5 hour, the solvent was removed and the residue was purified by flash chromatography on silica gel eluting with MeOH(10)/NH$_4$OH(1)H$_2$O (1) to provide 5-3.

$^1$H NMR (330 MHz, D$_2$O) δ 9.02 (m, 2H), 8.48 (s, 1H), 3.63 (t, 2H), 3.51 (t, 2H), 3.45 (d, 2H), 3.01 (dt, 2H), 2.5 (t, 2H), 2.03 (d, 2H), 1.75 (m, 1H), 1.68 (q, 2H), 1.45 (m, 2H).

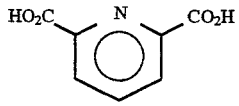

5-4

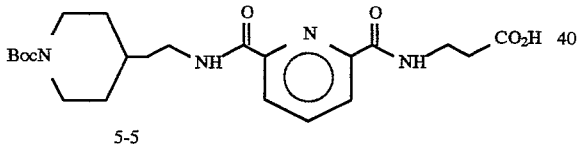

5-5

N-[2-(N'-Boc-4-Piperidinyl)ethyl]-N"-[(2-carboxy)ethyl]-2,6-pyridinedicarboxamide (5-5)

5-5 was prepared from 2,6-pyridinedicarboxylic acid (Aldrich) as described for 5-2. 5-5 had $^1$H NMR (300 MHz, CDCl$_3$) δ 8.54 (t, 1H), 8.40 (d, 2H), 8.05 (t, 1H), 7.75 (m, 1H), 4.2 (m, 2H), 3.8 (m, 2H), 3.6 (m, 2H), 2.7 (m, 4H), 1.8-1.6 (m, 5H), 1.48 (s, 9H), 1.3 (m, 2H).

5-5 ⟶

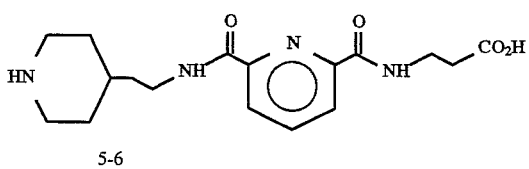

5-6

N-[2-(4-Piperidinyl)ethyl]-N'-[(2-carboxy)ethyl]-2,6-pyridinedicarboxamide (5-6)

5-6 was prepared as described for 5-3.

$^1$H NMR (300 MHz, CD$_3$OD+DTFA) δ 8.06 (d, 2H), 7.94 (t, 1H), 3.50 (t, 2H), 3.33 (t, 2H), 3.18 (m, 2H), 2.78 (m, 2H), 2.48 (t, 2H), 1.88 (d, 2H), 1.5 (m, 3H), 1.22 (m, 2H).

SCHEME 6

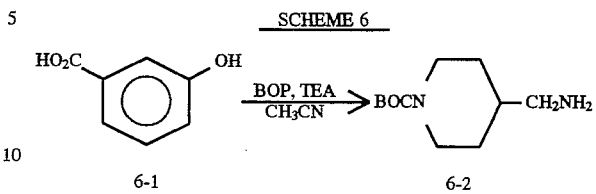

6-1   6-2

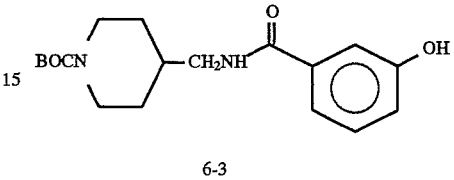

6-3

1. NaH
2. Br(CH$_2$)$_3$CO$_2$Et

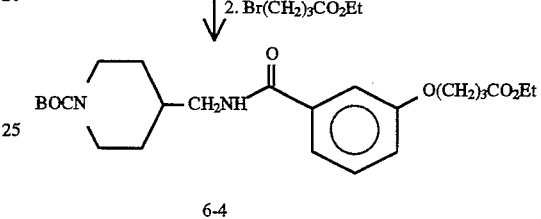

6-4

1. LiOH.H$_2$O
2. HCl (gas), EtOAc

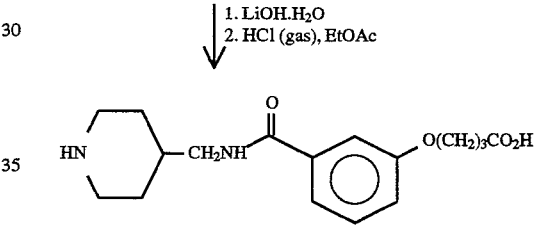

6-5

6-3

4-(N-t-Butyloxycarbonylpiperidinyl)methylamine (6-2)

A solution of 4-(piperidinyl)methylamine (Aldrich) (2-1) (22.8 g, 0.2 mmoles) in toluene (250 ml) was treated with benzaldehyde (21.2 g, 0.2 mmoles) at room temperature and the resulting mixture was heated at reflux for 3 hours with the aid of a Dean-Stark trap for water removal. The cooled reaction mixture containing the desired Schiff's base was treated portionwise with di-t-butyl dicarbonate (47.96 g, 0.22 moles) and the resulting solution was stirred at room temperature for 16 hours. The solvent was then removed and the residue was cooled to 0°–5° C. and treated with 1N KHSO$_4$ (220 ml) with stirring for 3 hours. The resulting reaction mixture was extracted with ether (3×200 ml) and then made basic with 1N KOH solution and extracted with CHCl$_3$ (4×75 ml). The combined organic extract was washed with brine, dried (Na$_2$SO$_4$) filtered through celite, and the solvent removed to provide pure 6-2 as a clear oil.

$^1$H NMR (300 MHz, CDCl$_3$) δ 1.13 (2H, m), 1.45 (9H, s), 1.60 (1H, m), 1.74 (2H, d), 2.68 (4H, m), 4.15 (2H, bd).

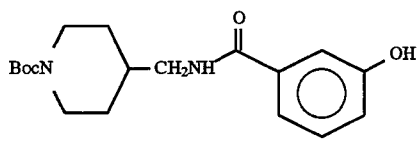

3-Hydroxy-N-[N'-Boc-4-(piperidinylmethyl)]
carboxamide (6-3)

A suspension of 3-hydroxybenzoic acid (1.0 g, 7.24 mmoles) in CH$_3$CN (15 ml) at room temperature was treated with 6-2 (7.24 mmoles) and BOP (4.8 g, 10.8 mmoles) to give a homogenous reaction mixture. TEA (21.7 mmoles) was added and this was stirred for 16 hours. The solvent was removed and the residue was taken up in EtOAc and washed with 10% KHSO$_4$ solution, brine and dried (MgSO$_4$). Solvent removal gave a residue that was purified by flash chromatography on silica gel eluting with 5% MeOH/CHCl$_3$ to give pure 6-3. R$_f$ 0.8 (silica, 10% MeOH/CHCl$_3$ (NH$_3$).

$^1$H NMR (300 MHz, CDCl$_3$) δ 1.14 (2H, m), 1.45 (9H, s), 1.70 (3H, m), 2.63 (2H, s), 3.31 (2H, b), 4.08 (2H, b), 6.58 (1H, t), 7.00 (1H, m), 7.22 (2H, m), 7.40 (1H, m).

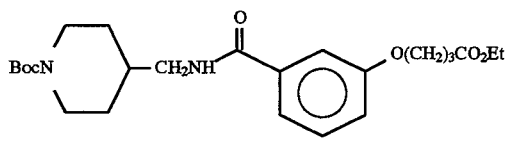

3-(3-Carboethoxypropyloxy)-N-[N'-Boc-4
(piperidinylmethyl)]-benzamide (6-4)

A solution of 6-3 (1.0 g, 2.99 mmoles) in DMF (15 ml) was treated with NaH (0.12 g, 2.99 moles) and, after 10 minutes stirring, the clear brown solution was treated with ethyl 4-bromobutyrate (3.3 mmoles). After 2 hours stirring at room temperature the solvent was removed and the residue was taken up in EtOAc, washed with H$_2$O, 10% KHSO$_4$ solution and brine. This was dried (MgSO$_4$), the solvent removed and the resulting residue purified by flash chromatography on silica gel eluting with 2% MeOH/CHCl$_3$ to give pure 6-4. R$_f$ 0.6 (silica, 5% MeOH/CHCl$_3$).

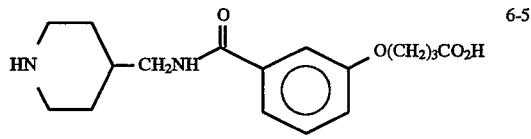

3-(3-Carboxypropyloxy)-N-(4-piperidinylmethyl)
carboxamide (6-5)

A solution of 6-4 (0.49 g, 1.09 mmoles) in 15 ml of THF/MeOH/H$_2$O (1:1:1) was treated with LiOH.H$_2$O (0.23 g, 5.45 mmoles) as described for 1-3 to give the desired acid. R$_f$ 0.7 (silica, 97:3:1 CHCl$_3$/MeOH/HOAc).

This acid was treated with HCl gas in EtOAc as described for 3-4 to give pure 6-5, R$_f$ 0.34, silica (CHCl$_3$, CH$_3$OH, HOAc, 97/3/1).

$^1$H NMR (300 MHz, CD$_3$OD) δ 1.50 (2H, m), 1.99 (2H, bd), 2.08 (2H, m), 2.50 (2H, t), 2.98 (2H, bt), 3.31 (2H, m), 3.41 (2H, bd), 4.06 (2H, t), 7.10 (1H, m), 7.58 (3H, m).

SCHEME 7

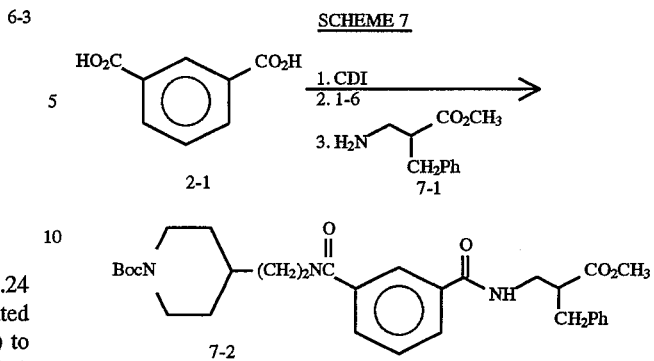

N-[2-(N'-Boc-4-piperidinylethyl)]-N''-3-[methyl 2-benzyl-propionate]-1,3-benzenedicarboxamide (7-2)

Treatment of 2-1 with CDI, 1-6 and methyl 2-benzyl-3-aminopropionate (7-1) (Phytochemistry 1988, 27, 711–14) as described for 1-2 gave 7-2. R$_f$ 0.34 (silica, 5% MeOH/CHCl$_3$).

$^1$H NMR (300 MHz, CHCl$_3$) δ 1.0 (2H, m) 1.5 (9H, s), 2.6 (3H, m), 1.65 (2H, d), 2.6 (2H, t), 2.8 (1H, dd), 2.95–3.05 (2H, m) 3.40 (2H, m), 3.61 (3H, s), 3.40–3.65 (2H, m), 4.0 (2H, d), 6.75 (1H, t), 7.05 (1H, t), 7.10–7.30 (6H, m), 7.41 (1H, t), 7.78 (1H, d), 7.90 (1H, d), 8.12 (1H, s).

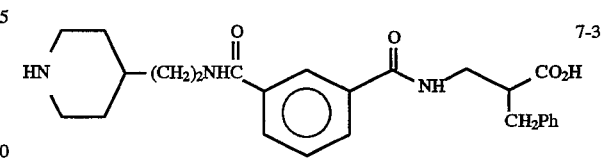

N-2-(4-Piperidinylethyl)-N'-3-(2-benzylpropionic
Acid)-1,3-benzenedicarboxamide (7-3)

7-2 was hydrolyzed with LiOH.H$_2$O and then deprotected with HCl gas in EtOAc as described for 3-4 to provide pure 7-3. R$_f$ 0.22 (silica, EtOH/H$_2$O/MeOH 9:1:1).

$^1$H NMR (300 MHz, D$_2$O+DCl) δ 1.2 (2H, m), 1.6–1.8 (3H, m), 2.0 (2H, d), 2.95 (4H, m), 3.20 (1H, m), 3.40 (4H, m), 3.60 (2H, m), 7.25 (5H, m), 7.60 (1H, t), 7.83 (1H, d), 7.88 (1H, d), 7.94 (1H, s).

SCHEME 8

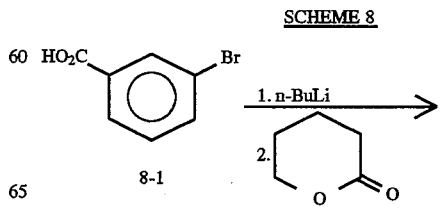

37

-continued
SCHEME 8

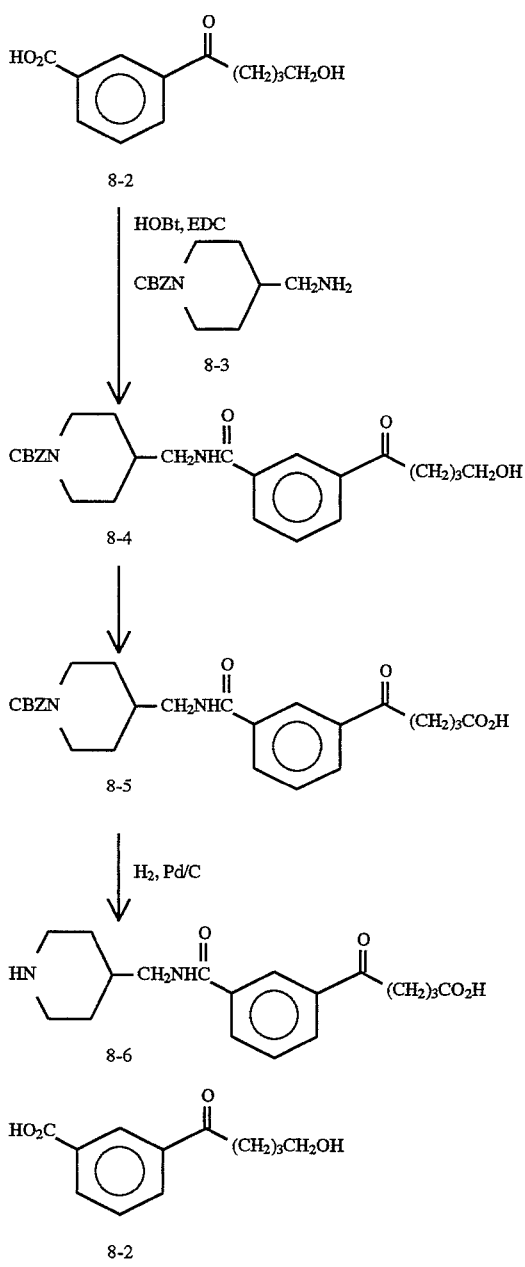

3-(5-Hydroxypentanoyl)benzoic Acid (8-2)

A solution of 3-bromobenzoic acid (Aldrich) (10.05 g, 0.05 moles) (8-1) in THF (250 ml) at −78° was treated with n-BuLi (0.1 moles) and the resulting solution was stirred at −78° for 1 hour. To this was added a solution of δ-valerolactone (Aldrich) (5.0 g, 0.05 moles) in THF (10 ml) at −78° and this was stirred at −78° for 3 hours and then allowed to gradually warm to room temperature overnight. The reaction was quenched with enough 10% KHSO₄ solution to provide a pH 2–3 and then extracted with EtOAc. The organic extract was washed with brine, dried (Na₂SO₄) and the solvent was removed. The resulting residue was purified by flash chromatography on silica gel eluting with CHCl₃/MeOH/HOAc 95:5:1 to give pure 8-2, R$_f$ 0.3 (silica).

38

$^1$H NMR (300 MHz, CD$_3$OD) δ 1.65 (2H, m), 1.80 (2H, m), 3.10 (2H, t), 3.6 (2H, t), 7.61 (1H, t), 8.18 (2H, t), 8.50 (1H, m).

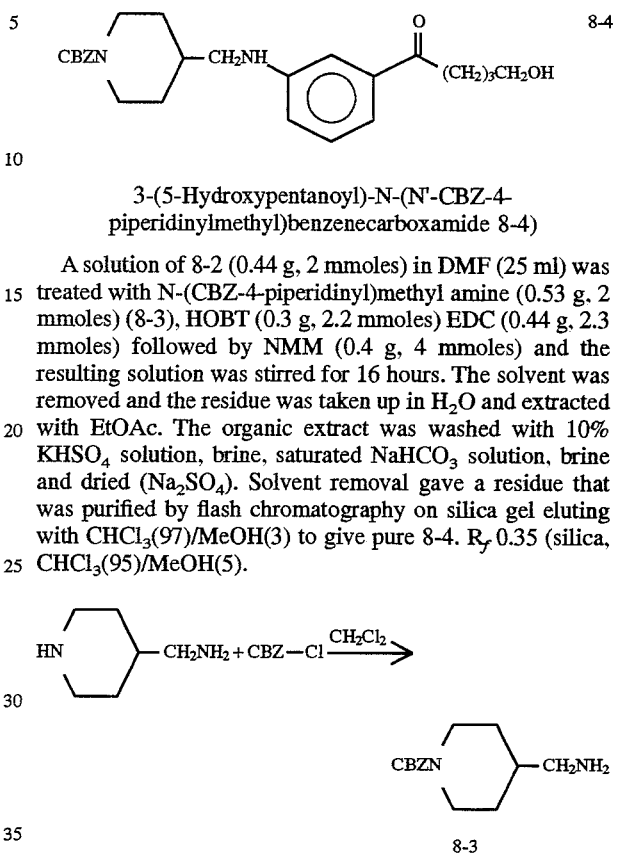

3-(5-Hydroxypentanoyl)-N-(N'-CBZ-4-piperidinylmethyl)benzenecarboxamide 8-4)

A solution of 8-2 (0.44 g, 2 mmoles) in DMF (25 ml) was treated with N-(CBZ-4-piperidinyl)methyl amine (0.53 g, 2 mmoles) (8-3), HOBT (0.3 g, 2.2 mmoles) EDC (0.44 g, 2.3 mmoles) followed by NMM (0.4 g, 4 mmoles) and the resulting solution was stirred for 16 hours. The solvent was removed and the residue was taken up in H$_2$O and extracted with EtOAc. The organic extract was washed with 10% KHSO$_4$ solution, brine, saturated NaHCO$_3$ solution, brine and dried (Na$_2$SO$_4$). Solvent removal gave a residue that was purified by flash chromatography on silica gel eluting with CHCl$_3$(97)/MeOH(3) to give pure 8-4. R$_f$ 0.35 (silica, CHCl$_3$(95)/MeOH(5).

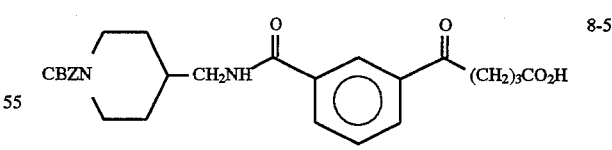

N-CBZ-(4-Aminomethyl)piperidine

A solution of 4-(aminomethyl)piperidine (Aldrich) (5.0 g, 0.0438 mol) in CH$_2$Cl$_2$ (100 ml) was cooled to −78° and treated with CBZ-Cl (Aldrich) (0.022 mol) dropwise. The reaction mixture was stirred at −78° for 0.5 hours and then allowed to warm to 0° over 1 hour. The reaction mixture was filtered and the solution concentrated to give a residue that was purified by flash chromatography on silica gel eluting with 5% MeOH/CHCl, +1% Et$_3$N to give pure product.

$^1$H NMR (300 MH$_3$, CDCl$_3$) δ 1.1 (2H, m), 1.4 (3H, m), 1.7 (2H, bd), 2.57 (2H, d), 2.75 (2H, bt), 4.2 (2H, bs), 5.11 (2H, s), 7.2–7.4 (5H, m).

3-(4-Carboxybutanoyl)-N-(N'CBZ-4-piperidinylmethyl)benzenecarboxamide (8-5)

An acetone solution (15 ml) of 8-3 was treated with Jones reagent at −10° and the resulting orange-brown solution was stirred for 1 hour. The reaction mixture was diluted with H$_2$O and extracted with EtOAc. The organic extract was dried (Na$_2$SO$_4$), concentrated, and the resulting residue purified by flash chromatography on silica gel eluting with CHCl$_3$ (95)/MeOH(5)/HOAc(1), R$_f$ 0.3.

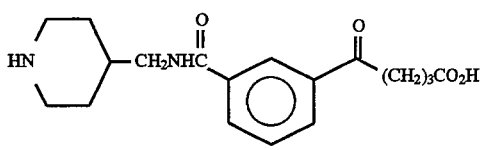

3-(5-Carboxypentanoyl)-N-(4-piperidinylmethyl)-benzenecarboxamide (8-6)

A solution of 8-5 (0.19 g) in MeOH (20 ml) was treated with 150 mg 10% Pd/C and this suspension was hydrogenated for 16 hours under balloon pressure. After the catalyst was removed by filtration, the solvent was removed and the residue purified by flash chromatography on silica gel eluting with EtOH(10)/conc. NH$_4$OH(1)/H$_2$O(1) to give pure 8-6.

$^1$H NMR (300 MHz, CD$_3$OD) δ 1.56 (4H, m), 1.82 (2H, m), 1.93 (3H, m), 2.20 (2H, m), 2.93 (2H, t), 3.40 (4H, m), 4.71 (1H, m), 7.45 (1H, t), 7.55 (1H, d), 7.70 (1H, d), 7.95 (1H, s).

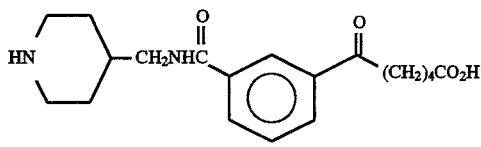

3-(5-Carboxypentanoyl)-N-(4-piperidinylmethyl) benzenecarboxamide (8-7)

This compound was prepared as described for 8-6, wherein E-caprolactam (Aldrich) is used in the inital step, to provide 8-7 as a white solid.

$^1$H NMR (300 MHz, CD$_3$OD) δ 1.40–1.60 (2H, m), 1.60–1.85 (4H, m), 1.90–2.10 (3H, m), 2.35 (2H, t), 3.00 (2H, dt), 3.12 (2H, t), 3.33–3.5 (4H, m), 7.61 (1H, t), 8.06 (1H, d), 8.17 (1H, d), 8.43 (1H, s).

SCHEME 9

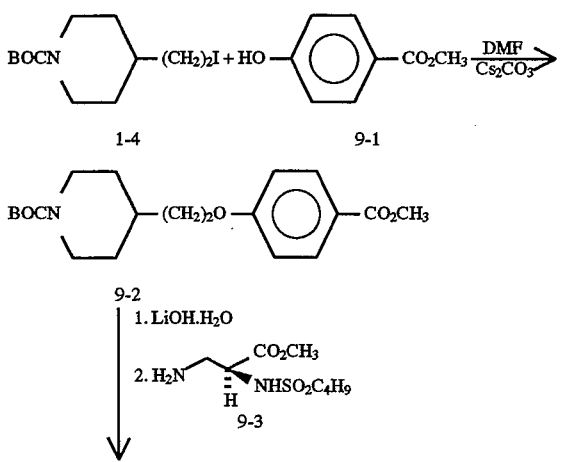

-continued
SCHEME 9

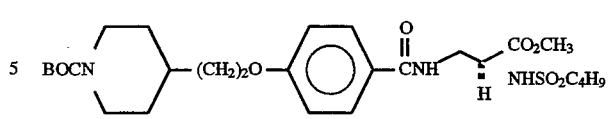

Methyl 4-[2-(N-BOC-4-Piperidinyl)ethyloxy] benzoate (9-2)

A solution of methyl 4-hydroxybenzoate (Aldrich) (0.4 g, 2.6 mmoles) 9-1 in DMF (10 ml) was treated with 2-(N-Boc-4-piperidinyl)ethyl iodide 1-4 (0.6 g, 1.77 mmoles) and CS$_2$CO$_3$ (1.15 g, 3.5 mmoles) with stirring at room temperature for 48 hours. The reaction mixture was diluted with EtOAc, washed with H$_2$O, saturated NaHCO$_3$, 10% KHSO$_4$, brine dried (MgSO$_4$) and concentrated. The residue was purified by flash chromatography on silica gel eluting with 20% EtOAc/hexanes to give pure 9-2. R$_f$ 0.3.

$^1$H NMR (300 MHz, CDCl$_3$) δ 1.36 (2H, m), 1.45 (9H, s), 2.44 (5H, m), 2.70 (2H, t), 3.88 93H, s), 6.88 (2H, d), 7.96 (2H, d).

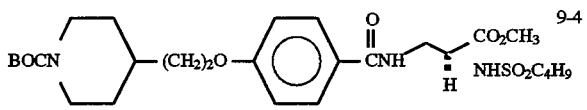

4-[2-(N-BOC-piperidin-4-yl)ethyloxy]benzoyl-2(S)-n-butylsulfonylamino-β-alanine Methyl Ester (9-4)

A solution of 9-2 (0.4 g, 1.14 mmoles) in H$_2$O (3 ml)/THF(4 ml) was treated with LiOH (2 mmoles) and the resulting solution stirred overnight at room temperature. The reaction mixture was acidified with 5% KHSO$_4$ extracted with EtOAc and the organic phase was washed with brine, dried (MgSO$_4$) and concentrated to give the desired acid. R$_f$ 0.5 (silica, CHCl$_3$(10)/MeOH(0.25)/AcOH(0.25).

This acid (0.1 g, 0.37 mmoles) was dissolved in CH$_3$CN (2 ml) and treated with methyl 3-amino-2(S)-n-butylsulfonylamino propionate (9-3) (0.1 g, 0.37 mmoles), BOP (0.246 g, 0.55 mmoles) and NMM (0.15 g, 1.48 mmoles) and the resulting mixture was stirred overnight. Then, the reaction mixture was diluted with EtOAc, washed with H$_2$O, saturated NaHCO$_3$, 10% KHSO$_4$, brine, dried (MgSO$_4$) and concentrated. The residue was purified by flash chromatography on silica gel eluting with 60% EtOAc/hexanes to give pure 9-4. R$_f$ 0.4 (silica, 60% EtOAc/hexanes).

$^1$H NMR (300 MHz, CDCl3) δ 0.92 (3H, s), 1.20 (2H, m), 1.45 (9H, s), 1.67 (4H, m), 2.76 (2H, bt), 3.04 (2H, t), 3.80

(5H, m), 4.10 (4H, m), 4.31 (1H, m), 6.92 (2H, d), 7.79 (2H, d).

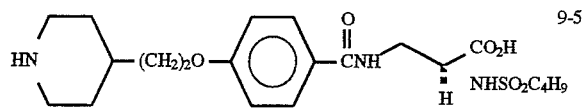

4-[2-(4-Piperidinyl)ethyloxy]-N-[3-(2(S)-n-butylsulfonylamino)propionate]benzamide (9-5)

A solution of (9-4) (0.2 g, 037 mmoles) in EtOH (2 ml) was treated with NaOH (0.5 mmoles) and the resulting solution was stirred for 1 hour at room temperature. The reaction mixture was then acidified to pH 2–3 with 10% KHSO₄ solution and extracted with EtOAc. The organic extract was washed with brine, dried (MgSO₄) and concentrated to give the desired acid. R$_f$ 0.25 (silica, CHCl₃(10)/MeOH(0.5)/AcOH(0.5).

This acid (0.18 g, 0.34 mmoles) was dissolved in CH₂Cl₂ (2 ml) and treated at room temperature with CF₃CO₂H (2 ml) for 1 hour. The solvents were removed and the residue was purified by flash chromatography on silica gel eluting with EtOH(10/H₂O(1)/NH₄OH(1) to give pure 9-5. R$_f$ 0.5.

¹H NMR (300 MHz, D₂O) δ 0.68 (3H, s), 1.18 (2H, m), 1.40 (2H, m), 1.59 (2H, m), 1.73 (2H, m), 1.80 (2H, m), 1.94 (2H, bd), 2.92 (2H, dt), 3.06 (2H, t), 3.37 (2H, bd), 3.54 (1H, m), 3.81 (1H, dd), 4.12 (2H, t), 4.31 (1H, m), 7.02 (2H, d), 7.75 (2H, d).

Preparation of Methyl 3-Amino-2(S)-n-butylsulfonylaminopropionate (9-3)

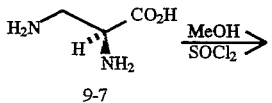
9-7

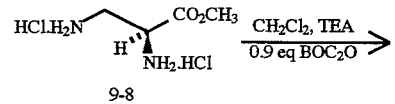
9-8

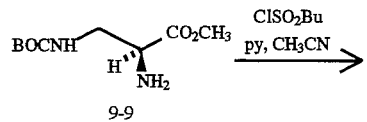
9-9

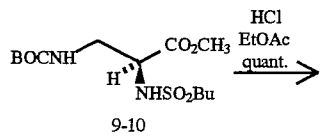
9-10

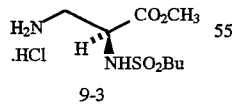
9-3

Methyl 2(S),3-Diaminopropanoate (9-8)

Methanol (400 mL) was cooled to 0° C. and thionyl chloride (217 mL, 3.0 moles, 20 eq) was added dropwise under argon. After addition was completed, the solution was warmed to room temperature for 20 minutes. 2(S),3-Diaminopropanoic acid (Schweizerhall) (20 g, 0.243 mole) was crushed to a fine powder and added to the solution. The reaction was heated to reflux for 48 hours, at which time TLC showed a small amount of starting material remaining. An additional portion of methanol (100 mL) and thionyl chloride (72 mL) was prepared as before and added to the reaction at room temperature; the reaction was then stirred overnight at room temperature. The reaction was worked up by removal of solvent at 40° C. in vacuo, to provide 9-8. R$^f$ 0.72 (9:1:1 EtOH/H₂O/NH₄OH).

¹H NMR (400 MHz, D₂O) δ 4.55 (dd, J=5.4, 8.2Hz, 1H), 3.92 (s, 3H), 3.64 (dd, J=8.2, 13.8Hz, 1H), 3.55 (dd, J=5.4, 13.8Hz, 1H).

Methyl 2(S)-3(N-t-Butyloxycarbonyl) diaminopropanoate (9-9)

9-8 (6.0 g, 31.5 mmoles) was crashed to a fine powder, suspended in 1 L of CH₂Cl₂ and cooled to –78° C. under argon. Triethylamine (17.5 mL, 0.126 moles, 4 eq) was added dropwise; the solution gradually became homogenous. Di-t-butyldicarbonate (6.18 g, 2.83 mmoles, 0.9 eq) was dissolved in 50 mL CH₂Cl₂ and added dropwide to the solution. After the addition was completed, the reaction was placed in an ice bath and stirred for 1½ hours. The reaction was transferred to a separatory funnel and extracted with 3×50 mL of 10% KHSO₄ solution. The aqueous layer was washed with 3×10 mL of CH₂Cl₂, then basified with saturated NaHCO₃ and 3N NaOH solution to pH 10 and extracted with 10×100 mL of CH₂Cl₂. The organic layer was dried with Na₂SO₄, filtered and evaporated to give 4.9 g of a pale yellow oil. Column chromatography in 2.5% MeOH/EtOAc gave 9-9 as an oil. R$^f$ 0.39 (5% MeOH/EtOAc).

¹H NMR (400 MHz, CDCl₃) δ 5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

Methyl 2(S)-(N-Butylsulfonylamino)-3-(N-t-butyloxycarbonylamino)diaminopropionic (9-10)

9-9 was dissolved in acetonitrile (100 mL) and three portions of n-butylsulfonly chloride (1.62 mL, 12.5 mmoles), and pyridine (1.0 mL, 12.5 mmoles) were added over a period of three hours. The reaction was allowed to stir overnight, concentrated to ¼ its original volume, then diluted with 100 mL EtOAc and washed with 10% KHSO₄ (5×20 mL), dried with brine and MgSO₄, filtered and evaporated. Column chromatography in 20%–40% EtOAc/hexanes gave 9-10 as an oil. R$^f$ 0.6 (5% MeOH/CHCl3).

¹H NMR (400 MHz, CDCl₃) δ 5.48 (bd, 1H), 4.9 (bs, 2H), 4.22 (m, 1H), 3.8 (s, 3H), 3.53 (m, 2H), 3.02 (m, 2H), 1.80 (m, 2H), 1.46 (m, 2H), 1.43 (s, 9H), 0.94 (t, J=7.4Hz, 3H).

2(S)-(N-Butylsulfonylamino)-3-aminopropionic Acid Methyl Ester Hydrochloride (9-3)

9-10 (2.0 g, 5.9 mmoles) was dissolved in 30 mL of EtOAc and cooled to –40° C. HCl gas was bubbled through the solution until it was saturated, then the reaction was warmed to 0° C. and stirred for 1 hour. The excess HCl was removed under vaccum at room temperature and the reaction was concentrated at 35° C. to give 9-3. R$^f$ 0.6 (9:1 EtOH/H₂O).

¹H NMR (400 MHz, CDCl₃) δ 0.1 (bs, 2H), 7.2 (m, 1H), 4.65 (m, 1H), 3.82 (s, 3H), 3.65 (m, 1H), 3.54 (m, 1H), 3.20 (bs, 2H), 1.8 (m, 2H), 1.45 (m, 2H), 0.95 (t, J=7.3Hz).

Preparation of Methyl 2(S)-Phenylsulfonylamino-3-aminopropionate Hydrochloride (9-12)

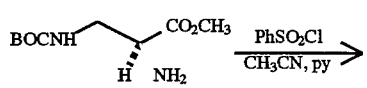

9-9

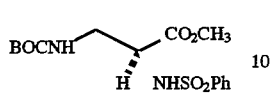

9-11

↓

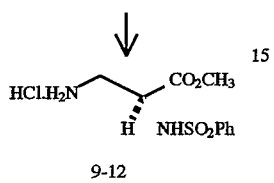

9-12

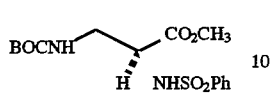

9-11

2(S)-(Phenylsulfonylamino)-3-(N-t-butyloxycarbonylamino)propionic Acid Methyl Ester (9-11)

Utilizing the procedure for converting 9-9 to 9-10, 9-9 (700 mg, 3.1 mmol) gave 9-11 (900 mg) as a white solid after flash chromatography (silica, 30% EtOAc/hexanes).

$^1$H NMR (400 MHz, CDCl$_3$) δ 7.85 (m, 2H), 7.60-7.50 (m, 3H), 5.67 (m, 1H), 4.00 (m, 1H), 3.56 (s, 3H), 3.47 (m, 2H), 1.45 (s, 9H).

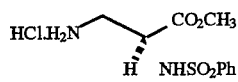

9-12

Methyl 2(S)-(Phenylsulfonylamino)-3-aminopropionate Hydrochloride (9-12)

Utilizing the procedure for converting 9-10 to 9-3, 9-11 (900 mg) gave 9-12 (800 mg) as a white solid.

$^1$H NMR (400 MHz, CD$_3$OD) δ 7.88 (m, 2H), 7.65 (m, 1H), 7.60 (m, 1H), 4.25 (m, 1H), 3.42 (s, 3H), 3.35 (m, 1H), 3.10 (m, 1H).

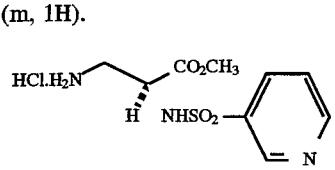

9-13

Methyl 2(S)-(3-Pyridylsulfonylamino)-3-aminopropionate Hydrochloride (9-13)

Compound 9-13 was prepared in a manner similar to that used for 9-12, utilizing 3-chlorosulfonylpyridine (Synthesis, 1983, p. 822). R$_f$ 0.34 (9:1:1 EtOH/H$_2$O/NH$_4$OH) δ 9.3 (s, 1H), 9.0 (dd, J=1.5Hz, 1H), 8.9 (d, J=9Hz, 1H), 8.2 (dd, J=5, 9Hz, 1H), 4.6 (dd, J=5, 9Hz, 1H), 3.6 (s, 3H), 3.5 (dd, J=5, 13Hz, 1H), 3.3 (dd, J=9, 13Hz, 1H).

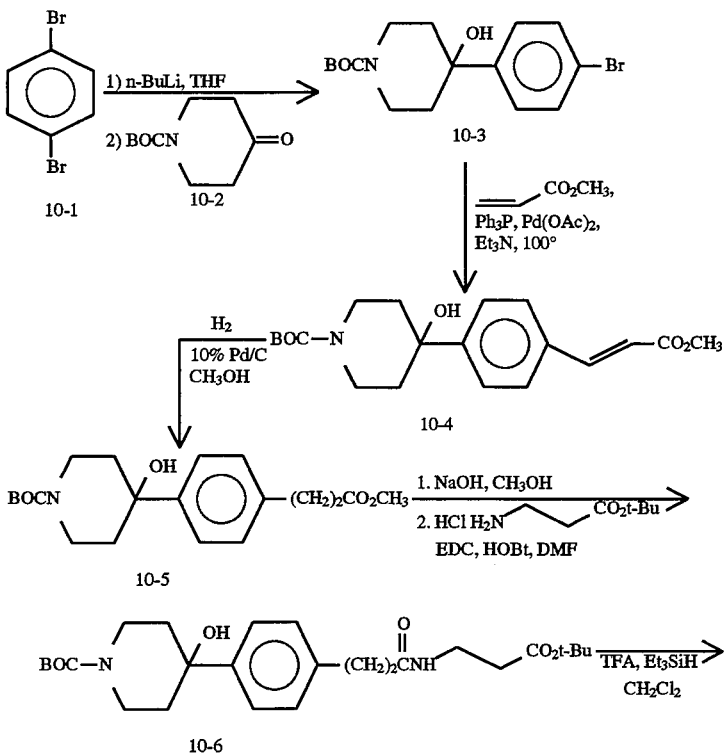

SCHEME 10

-continued
SCHEME 10

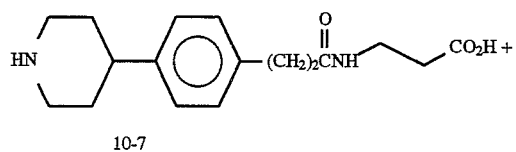

10-7

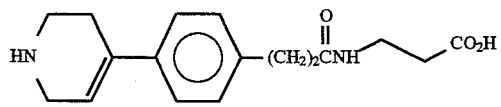

10-8

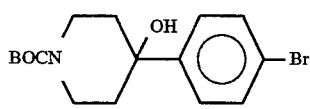

4-(N-BOC-4-Hydroxypiperidin-4-yl)bromobenzene (10-3)

A solution of 1,4-dibromobenzene (7.10 g, 30.1 mmoles) in THF (50 ml) at −78° was treated with n-BuLi (18.7 ml, 30 mmoles, 1.6M/hexane) and after 1.0 hour stirring at −78°, N-BOC-4-piperidone (10-2) (2.0 g, 10.04 mmoles) in THF (2 ml) was added. After 1 hour the cooling both was removed and the reaction mixture was stirred for 2 hours. The reaction mixture was then diluted with EtOAc, washed with water, 10% KHSO$_4$, brine, dried (MgSO$_4$) and concentrated. The residue was purified by flash chromatography on silica gel eluting with 20% EtOAc/hexanes to give pure 10-3. $R_f$ 0.15 (silica, 20% EtOAc/hexanes).

$^1$H NMR (300 MHz, CDCl$_3$) δ 1.45 (9H, s), 1.67 (2H, bs), 1.90 (2H, m), 3.16 (2H, dt), 3.97 (2H, bd), 7.30 (2H, d), 7.43 (2H, d).

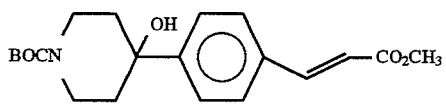

Methyl 3-[4-(N-BOC-4-Hydroxypiperidin-4-yl)phenyl]acrylate (10-4)

A solution of 10-3 (0.5 g, 1.4 mmoles), methyl acylate (1.2 g, 14 mmoles), Pd(OAc)$_2$ (0.031 g, 0.24 mmoles) Et$_3$N (0.56 g, 5.6 mmoles) and Ph$_3$P (0.17 g, 0.56 mmoles) in CH$_3$CN (40 ml) was heated at 100° in a sealed tube for 24 hours.

The cooled reaction mixture was diluted with EtOAc, washed with H$_2$O, 10% KHSO$_4$, brine, dried (MgSO$_4$) and concentrated. The residue was purified by flash chromatography on silica gel eluting with 25% EtOAc/hexanes to give pure 10-4. $R_f$ 0.55 (silica, 50% EtOAc/hexanes).

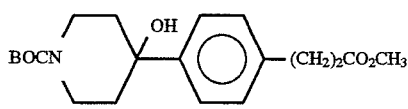

Methyl 3-[4-(N-BOC-4-Hydroxypiperidin-4-yl)phenyl]propionate (10-5)

A solution of 10-4 (0.42 g, 1.16 mmoles) in MeOH (6 ml) was treated with 0.17 g 10% Pd/C and this was hydroge-
nated under 1 atm. of H$_2$ pressure for 48 hours. Solvent removal and purification by flash chromatography on silica gel eluting with 50% EtOAc/hexanes gave pure 10-5. $R_f$ 0.55 (silica, 50% EtOAc/hexanes).

$^1$H NMR (300 MHz, CDCl$_3$) δ 1.45 (9H, s), 1.62 (2H, m), 1.72 (2H, bd), 1.97 (2H, m), 2.64 (2H, t), 2.95 (2H, t), 3.24 (2H, by), 4.03 (2H, m), 7.21 (2H, d), 7.40 (2H, d).

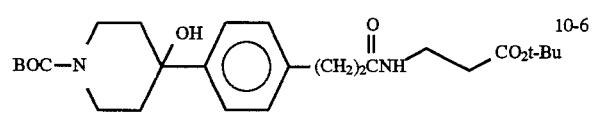

4-(N-BOC-4-Hydroxypiperidin-4-yl)phenyl-3-propionyl-β-alanine t-Butyl Ester (10-6)

A solution of 10-5 (0.4 g, 1.1 mmoles) in CH$_3$OH (6 ml) was treated at room temperature with 1N NaOH (4.4 ml) and the resulting solution was stirred for 1 hour. The solvent was removed, the residue acidified with 10% KHSO$_4$ and extracted with EtOAc. The organic extract was dried (MgSO$_4$) and concentrated to give the desired acid (10-9) as a white solid. $R_f$ 0.75 (silica, CH$_2$Cl$_2$(10/AcOH(0.51/MeOH(0.50).

A solution of this acid (0.275 g, 0.79 mmoles) in DMF (5 ml) at −15° was treated with β-alanine hydrochloride t-butyl ester (0.16 g, 0.94 mmoles), HOBT (0.12 g, 0.94 mmoles), DIPEA (0.6 ml, 3.1 mmoles) followed by EDC (0.18 g, 0.94 mmoles). The cooling bath was then removed and the reaction mixture stirred at ambient temperature for 18 hours. The reaction mixture was diluted with EtOAc (50 ml), washed with H$_2$O, saturated NaHCO$_3$, 10% KHSO$_4$, brine, dried (MgSO$_4$) and concentrated. The residue was purified by flash chromatography on silica gel eluting with 80% EtOAc/hexanes to give pure 10-6. $R_f$ 0.25 (silica, 80% EtOAc/hexanes).

$^1$H NMR (300 MHz, CDCl$_3$) δ 1.45 (9H, s), 1.50 (9H, s), 1.75 (2H, bd), 2.00 (2H, m), 2.38 (2H, t), 2.46 (2H, t), 2.96 (2H, t), 3.26 (2H, t), 3.46 (2H, q), 4.04 (2H, bd), 7.22 (2H, d), 7.40 (2H, d).

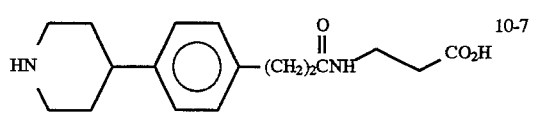

and

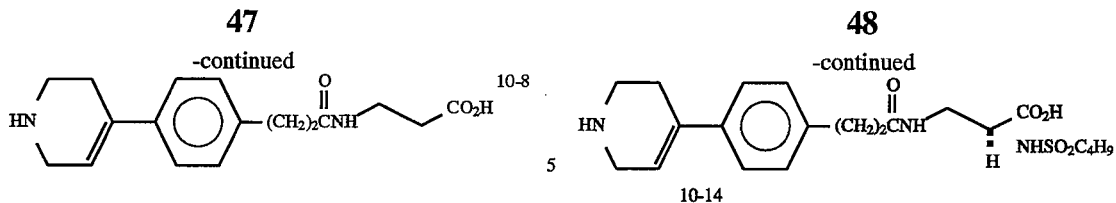

4-(Piperidin-4-yl)phenyl-3-propionyl-β-alanine (10-7) 4-(1,2,5,6-Tetrahydropyridin-4-yl)phenyl-3-propionyl-β-alanine (10-8)

A solution of 10-6 (0.225 g, 0.47 mmoles) in $CH_2Cl_2$ (5 ml) was treated with $Et_3SiH$ (0.33 g, 4.2 mmoles) at ambient temperature and the resulting solution was stirred for 18 hours. The solvent was removed and the residue was purified by flash chromatgraphy on silica gel eluting with EtOH(10)/$H_2O$(1)/$NH_4OH$(1) to give two components: 10-8 had $R_f$ 0.25 under these conditions:

1H NMR (300 MHz, $D_2O$) δ 2.48 (2H, t), 2.87 (2H, t), 3.13 (2H, b), 3.25 (2H, t), 3.56 (2H, t), 3.72 (2H, t), 4.20 (2H, bs), 6.49 (1H, m), 7.59 (2H, d), 7.78 (2H, d).

10-7 had $R_f$ 0.2 (silica, EtOH(10)/$H_2O$(1)/$NH_4OH$(1) and $^1H$ NMR (300 MHz, $D_2O$) d 1.87 (2H, m), 2.10 (4H, m), 2.50 (2H, t), 2.88 (2H, t), 3.12 (2H, dt), 3.20 (2H, t), 3.5 (2H, m), 7.41 (2H, d), 7.48 (2H, d).

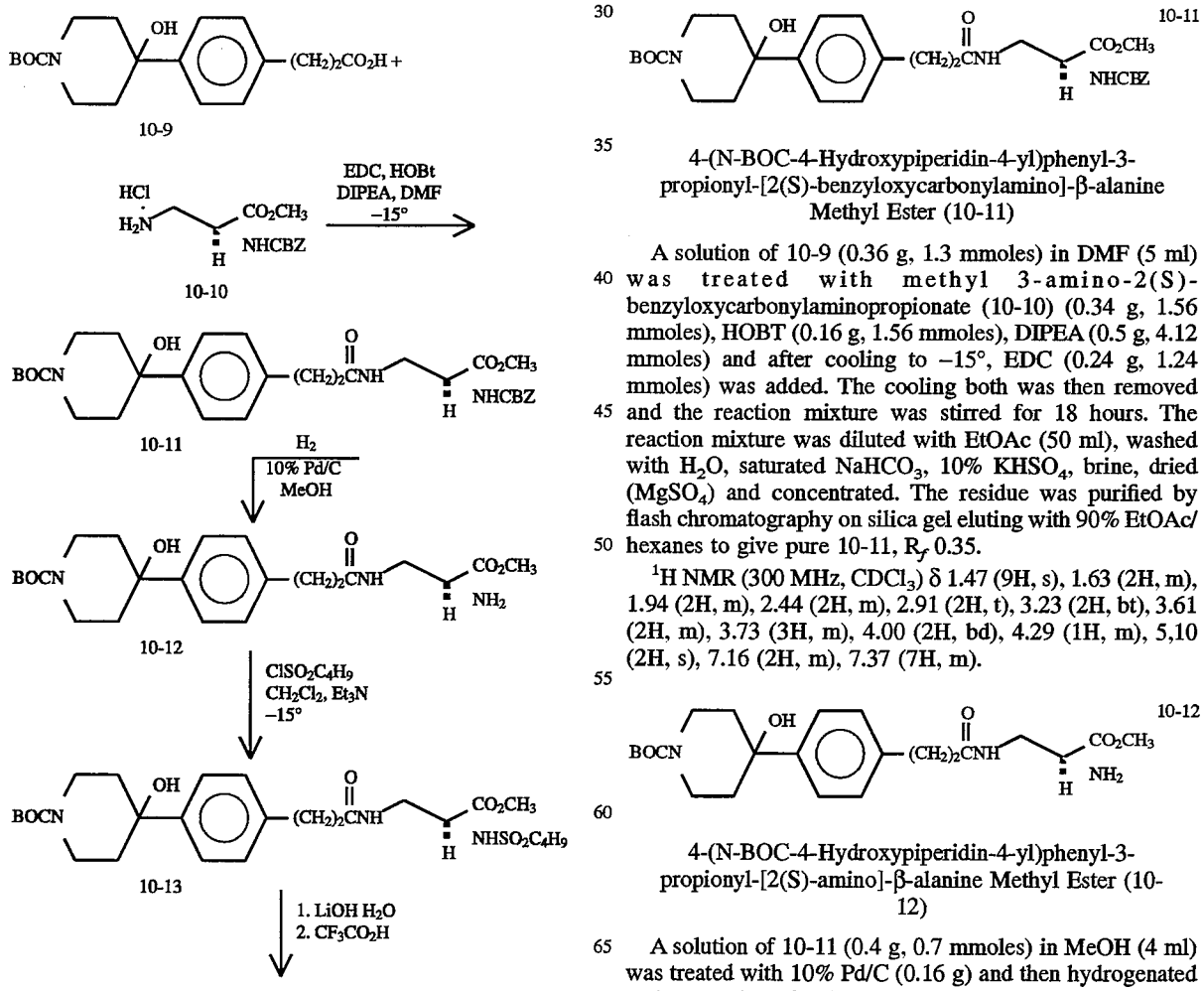

Methyl 3-amino-2(S)-benzyloxycarbonylaminopropionate Hydrochloride (10-10)

3-Amino-2(S)-benzyloxycarbonylaminopropionic acid (Fluka) (5.0 g, 21.0 mmoles) was suspended in MeOH and at −10° $SOCl_2$ (23.0 mmoles) was added. The reaction mixture was allowed to gradually warm to room temperature over 16 hours. The solvent was then removed and the resulting solid was triturated with $Et_2O$ to give 10-10.

$^1H$ NMR (300 MHz, $D_2O$) δ 3.32 (2H, m), 3.52 (2H, m), 3.70 (1H, m), 3.80 (4H, m), 4.59 (1H, m), 5.18 (3H, s), 7.45 (5H, s).

4-(N-BOC-4-Hydroxypiperidin-4-yl)phenyl-3-propionyl-[2(S)-benzyloxycarbonylamino]-β-alanine Methyl Ester (10-11)

A solution of 10-9 (0.36 g, 1.3 mmoles) in DMF (5 ml) was treated with methyl 3-amino-2(S)-benzyloxycarbonylaminopropionate (10-10) (0.34 g, 1.56 mmoles), HOBT (0.16 g, 1.56 mmoles), DIPEA (0.5 g, 4.12 mmoles) and after cooling to −15°, EDC (0.24 g, 1.24 mmoles) was added. The cooling both was then removed and the reaction mixture was stirred for 18 hours. The reaction mixture was diluted with EtOAc (50 ml), washed with $H_2O$, saturated $NaHCO_3$, 10% $KHSO_4$, brine, dried ($MgSO_4$) and concentrated. The residue was purified by flash chromatography on silica gel eluting with 90% EtOAc/ hexanes to give pure 10-11, $R_f$ 0.35.

$^1H$ NMR (300 MHz, $CDCl_3$) δ 1.47 (9H, s), 1.63 (2H, m), 1.94 (2H, m), 2.44 (2H, m), 2.91 (2H, t), 3.23 (2H, bt), 3.61 (2H, m), 3.73 (3H, m), 4.00 (2H, bd), 4.29 (1H, m), 5,10 (2H, s), 7.16 (2H, m), 7.37 (7H, m).

4-(N-BOC-4-Hydroxypiperidin-4-yl)phenyl-3-propionyl-[2(S)-amino]-β-alanine Methyl Ester (10-12)

A solution of 10-11 (0.4 g, 0.7 mmoles) in MeOH (4 ml) was treated with 10% Pd/C (0.16 g) and then hydrogenated at 1 atmosphere for 1 hour. The catalyst was removed and the reaction mixture was concentrated to give 10-12 as a white solid. R$_f$ 0.35 (silca, 20% CH$_3$OH/EtOAc).

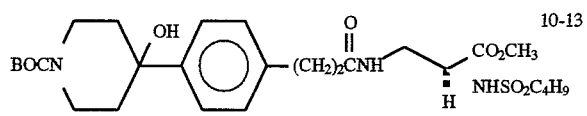

4-(N-BOC-4-Hydroxypiperidin-4-yl)phenyl-3-propionyl-[2(S)-n-butylsulfonylamino]-β-alanine Methyl Ester (10-13)

A solution of 10-12 (0.3 g, 0.7 mmoles) in CH$_2$Cl$_2$ (5 ml) was treated at 0° C. with Et$_3$N (0.14 g, 1.4 mmoles) followed by n-butylsulfonyl chloride (0.22 g, 1.4 mmoles) and the resulting mixture was stirred for 1.0 hours. The reaction mixture was then diluted with EtOAc, washed with H$_2$O, saturated NaHCO$_3$, 10% KHSO$_4$, brine dried (MgSO$_4$) and concentrated. The residue was purified by flash chromatography on silica gel eluting with 60% EtOAc/hexanes to give pure 10-13, R$_f$ 0.2 (silica, 60% EtOAc/hexanes).

$^1$H NMR (300 MHz, CDCl$_3$), δ 0.95 (3H, t), 1.48 (9H, s), 1.59 (3H, m), 1.73 (2H, m), 1.95 (2H, m), 2.50 (2H, t), 2.94 (2H, m), 3.24 (2H, dt), 3.57 (2H, m), 3.79 (3H, s), 4.02 (2H, m), 7.22 (2H, d), 7.43 (2H, d).

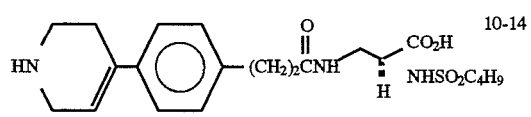

4-(1,2,5,6-Tetrahydropyridin-4-yl)phenyl-3-propionyl-[2(S)-n-butylsulfonylamino]-β-alanine (10-14)

A solution of 10-13 (0.2 g, 0.36 mmoles) in CH$_3$OH (2 ml) was treated with LiOH (1.0 mmoles) at room temperature with stirring for 4 hours. The solvent was removed, the residue acidified with 10% KHSO$_4$ and this was extracted with EtOAc. The organic extract was washed with brine, dried (MgSO$_4$), and concentrated to give the desired acid. R$_f$ 0.25 (silica, CH$_2$Cl$_2$(10)/MeOH(0.5)/AcOH(0.5)).

This acid (0.18 g, 0.33 mmoles) was dissolved in CH$_2$Cl$_2$ (2 ml) and treated with CF$_3$CO$_2$H (2 ml) at room temperature with stirring for 1 hour. The solvent was removed and the residue was purified by flash chromatography on silica gel eluting with EtOH(10)/NH$_4$OH(1)/H$_2$O(1) to give pure 10-14.

$^1$H NMR (300 MHz, D$_2$O) δ 0.75 (3H, t), 1.26 (2H, m), 1.54 (2H, m), 2.45 (2H, m), 2.64 (2H, bs), 2.78 (2H, m), 2.92 (2H, m), 3.35 (4H, m), 3.70 (2H, m), 3.91 (1H, m), 6.00 (1H, m), 7.12 (2H, d), 7.30 (2H, d).

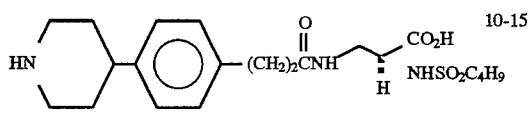

4-(Piperidin-4-yl)phenyl-3-propionyl-[2(S)-n-butylsulfonylamino]-β-alanine (10-15)

A solution of 10-14 (0.05 g, 0.114 mmoles) in CH$_3$OH (1 ml) was treated with 10% Pd/C (25 mg) and then hydrogenated for 2 hours at 1 atom H$_2$. The catalyst was then removed by filtration. The solution concentrated to give pure 10-15. R$_f$ 0.3 (silica, EtOH(10)/H$_2$O(1)/NH$_4$OH(1).

$^1$H NMR (300 MHz, CD$_3$OD) δ 0.86 (3H, t), 1.35 (2H, m), 1.68 (2H, m), 1.80 (2H, m), 1.96 (2H, bd), 2.40 (2H, m), 2.79 (3H, m), 2.97 (2H, m), 3.02 (2H, dt), 3.40 (2H, bd), 3.52 (2H, m), 4.06 (1H, m), 7.08 (5H, s).

SCHEME 11

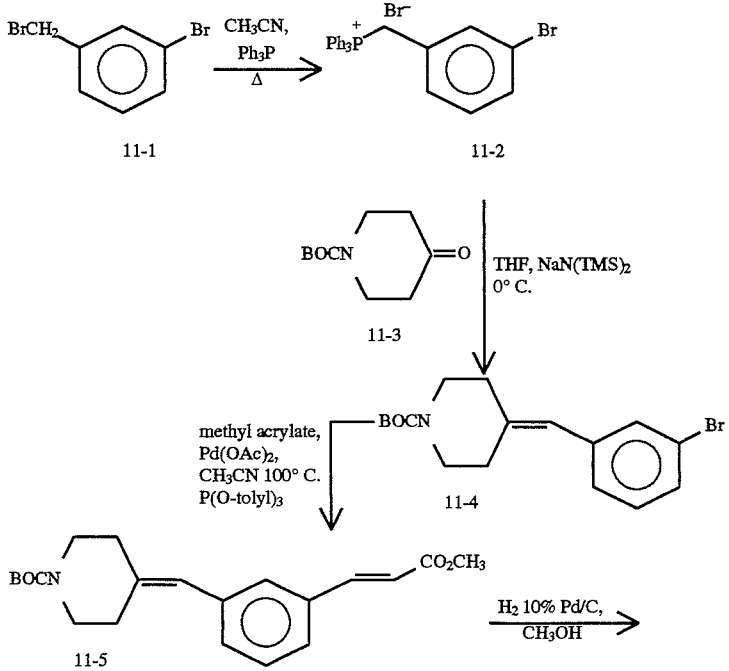

-continued
SCHEME 11

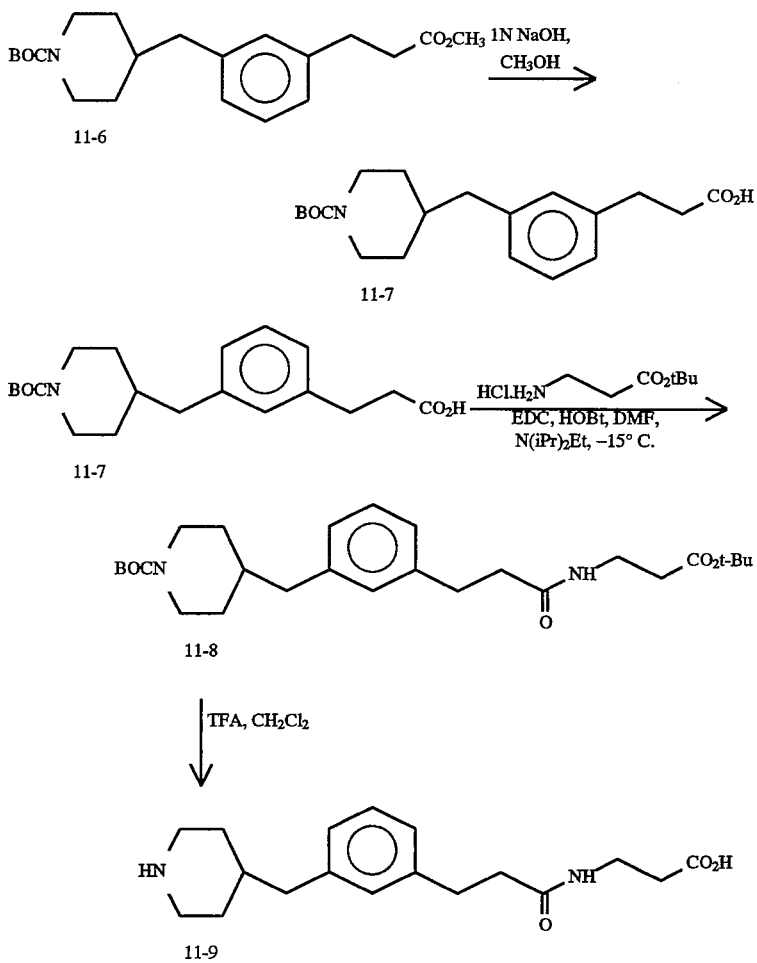

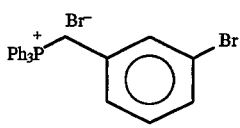

3-Bromobenzyltriphenylphosphonium Bromide (11-2)

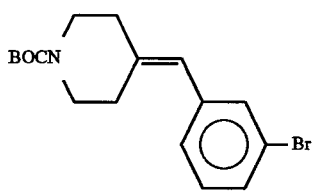

3-[(N-Boc-(1,2,3,5,6-pentahydropyridin-4-ylmethylene)-bromobenzene (11-4)

A stirred mixture of 3-bromobenzyl bromide (Aldrich) (5.1 g, 20.5 mmoles), triphenylphosphine (54 g, 0.20 moles), and $CH_3CN$ (100 mL) was refluxed for 20 hours. The cooled reaction mixture was then concentrated and the residue triturated with hexanes (10×) to remove excess triphenylphosphine. The remaining white solid was collected by filtration and then dried in vacuo to give 11-2 as a white solid.

$^1$H NMR (300 MHz, $CDCl_3$) δ 7.90-7.60 (m, 15H), 7.28 (m, 2H), 7.06 (t, J=8Hz, 1H), 6.97 (m, 1H), 5.60 (d, J=15Hz, 2H).

To a stirred solution of 11-2 (5.1 g, 10.0 mmoles) in THF (50 mL) at 0° C. was added $NaN(TMS)_2$ (13.0 mL), 13.0 mmoles, 1M/hexanes) dropwise. After 15 minutes the orange mixture was treated with 11-3 (2.0 g, 10.0 mmoles) in THF (10 mL), followed by removal of the cooling bath. After 20 hours the reaction mixture was diluted with EtOAc and then washed with $H_2O$, saturated $NaHCO_3$, 5% $KHSO_4$, and brine, dried ($MgSO_4$) and concentrated. Flash chromatography (silica, 5% EtOAc/hexanes) gave 11-4 as a colorless oil. $R_f$ 0.49 (silica, 5% EtOAc/hexanes).

$^1$H NMR (300 MHz, $CDCl_3$) δ 7.40-7.10 (m, 4H), 6.29 (s, 1H), 3.50 (m, 2H), 3.40 (m, 2H), 2.42 (m, 2H), 2.32 (m, 2H), 1.47 (s, 9H).

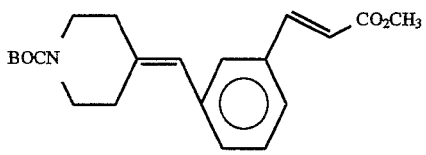

Methyl 3-[3-(N-BOC-1,2,3,5,6-Pentahydropyridin-4-yl-methylene)phenyl]acrylate (11-5)

A mixture of 11-4 (400 mg, 1.1 mmoles), methyl acrylate (1.0 g, 1.0 mL, 10.0 mmoles), Pd(OAc)$_2$ (26 mg, 0.11 mmoles), NEt$_3$ (0.16 mL, 1.1 mmol), tri-o-toluyl-phosphine (0.14 g, 0.45 mmoles), and CH$_3$CN (6 mL) was heated at 100° C. in sealed tube. After 24 hour the cooled reaction mixture was diluted with EtOAc and then washed H$_2$O, saturated NaHCO$_3$, 5% KHSO$_4$, and brine, dried (MgSO$_4$), and concentrated. Flash chromatography (silica, 5% EtOAc/hexanes) gave 11-5 as yellow solid. R$_f$=0.30 (silica, 5% EtOAc/hexanes).

$^1$H NMR (300 MHz, CDCl$_3$) δ 7.70 (d, J=17Hz, 1H), 7.40-7.20 (m, 4H), 6.42 (d, J=17Hz, 1H), 6.37 (s, 1H), 3.53 (m, 2H), 3.38 (m, 2H), 2.43 (m, 2H), 2.35 (m, 2H), 1.48 (s, 9H).

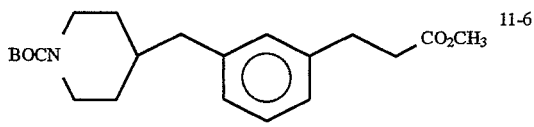

Methyl 3-[3-(N-BOC-Piperidin-4-ylmethyl)phenyl]propionate (11-6)

A mixture of 11-5 (310 mg, 0.87 mmoles), 10% Pd/C (125 mg), and CH$_3$OH (6 mL) was stirred under hdyrogen atmosphere (1 atm) at ambient temperature. After 20 hours the reaction mixture was filtered through a celite pad and the filtrate concentrated to give 11-6 as a yellow oil. R$_f$ 0.30 (silica, 10% EtOAc/hexanes).

$^1$H NMR (300 MHz, CDCl$_3$) δ 7.21 (m, 2H), 7.02 (m, 2H), 4.10 (m, 2H), 3.88 (s, 3H), 2.95 (m, 2H), 2.64 (m, 4H), 2.53 (d, J=7Hz, 2H), 1.65 (m, 2H), 1.47 (s, 9H), 1.15 (m, 2H).

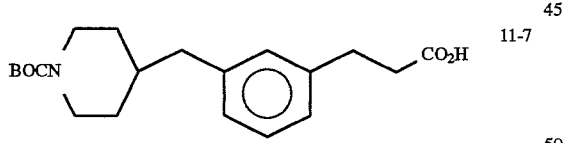

3-[3-(N-BOC-piperidin-4-ylmethyl)phenyl]propionic Acid (11-7)

A solution of 11-6 (290 mg, 0.80 mmoles), 1N NaOH (3 mL), and CH$_3$OH (4 mL) was stirred at ambient temperature for 1.0 hour. The reaction was then acidified with 10% KHSO$_4$ and extracted with EtOAc. The EtOAc portion was then washed with brine, dried (MgSO$_4$), and concentrated to give 11-7 as a yellow oil. R$_f$ 0.58 (silica, 10.5:0.5 CH$_2$Cl$_2$/CH$_3$OH/HOAc).

$^1$H NMR (300 MHz, CDCl$_3$) δ 7.22 (m, 2H), 7.01 (m, 2H), 4.07 (m, 2H), 2.94 (m, 2H), 2.68 (m, 2H), 2.65 (m, 2H), 2.52 (d, J=7Hz, 2H), 1.62 (m, 2H), 1.47 (s, 9H), 1.14 (m, 2H).

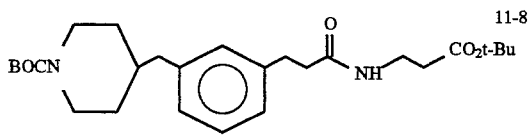

3-[3-(N-BOC-piperidin-4-ylmethyl)phenyl]propionyl-β-alanine-tert-butyl Ester (11-8)

To a stirred solution of 11-7 (275 mg, 0.79 mmoles), HOBT (130 mg, 0.95 mmoles), N(i-Pr)$_2$Et (0.55 mL, 3.2 mmoles), tert-butyl-β-alanine hydrochloride (160 mg, 0.95 mmoles), and DMF (4 mL), at −15° C. was added EDC (183 mg, 0.95 mmoles) followed by removal of the cooling bath. After 20 hours the reaction mixture was diluted with EtOAc and then washed with H$_2$O, saturated NaHCO$_3$, 10% KHSO$_4$, and brine, dried (MgSO$_4$), and concentrated. Flash chromatography (silica, 50% EtOAc/hexanes) gave 11-8 as a colorless oil. R$_f$ 0.21 (silica, 50% EtOAc/hexanes).

$^1$H NMR (300 MHz, CDCl$_3$) δ 7.22 (m, 2H), 7.00 (m, 3H), 6.04 (m, 1H), 4.10 (m, 2H), 3.48 (m, 2H), 2.96 (m, 2H), 2.66 (m, 2H), 2.51 (m, 2H), 2.43 (m, 2H), 1.63 (m, 2H), 1.48 (s, 18H), 1.16 (m, 2H).

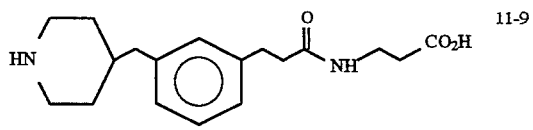

3-[3-(Piperidin-4-ylmethyl)phenyl]propionyl-β-alanine (11-9)

A solution of 11-8 (225 mg, 0.48 mmoles), TFA (2.5 mL), and CH$_2$Cl$_2$ (2.5 mL) was stirred at ambient temperature for 1.0 h. Concentration followed by flash chromatography (silica, 10:1:1 ethanol/H$_2$O/NH$_4$OH) gave 11-9 as a white solid. R$_f$ 0.44 (silica, 10:1:1 ethanol/H$_2$O/NH$_4$OH).

$^1$H NMR (400 MHz, D$_2$O) δ 7.40-7.00 (m, 4H), 3.38 (m, 2H), 3.21 (m, 2H), 2.90 (m, 2H), 2.60 (d, J=7Hz, 2H), 2.50 (m, 2H), 2.19 (m, 2H), 1.83 (m, 3H), 1.40 (m, 2H).

SCHEME 12

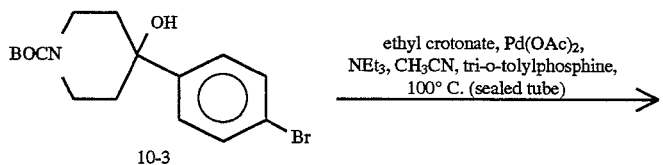

-continued
SCHEME 12

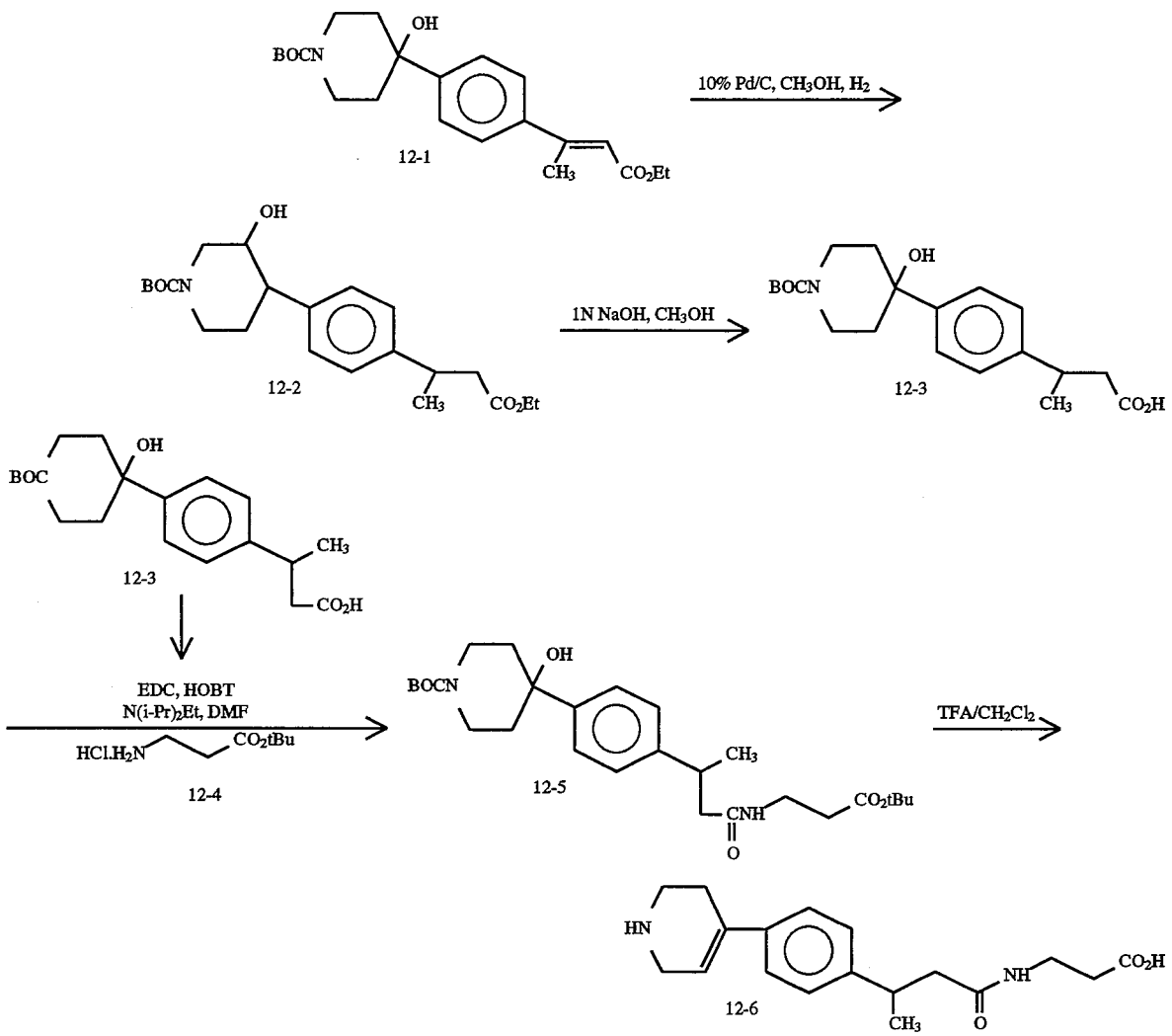

Ethyl 3-[4-(N-BOC-4-hydroxypiperidin-4-yl)phenyl]crotonate (12-1)

A mixture of 10-3 (500 mg, 1.4 mmoles), ethyl crotonate (1.7 mL, 3.8 mmoles), Pd(OAc)$_2$ (31 mg, 0.14 mmoles), NEt$_3$ (0.78 mL, 8 mmoles), tri-o-tolylphosphine (170 mg, 0.56 mmoles), and CH$_3$CN (7 mL) was heated in a sealed tube at 100° C. for 24 hours. The cooled reaction mixture was diluted with EtOAc and then washed with H$_2$O, 10% KHSO$_4$, saturated NaHCO$_3$, and brine, dried (MgSO$_4$), and concentrated. Flash chromatography (silica, 25% EtOAc/hexanes) gave 12-1 as a waxy yellow solid. R$_f$ 0.33 (silica, 25% EtOAc/hexanes).

$^1$H NMR (300 MHz, CDCl$_3$) δ 7.49 (m, 4H), 6.16 (s, 1H), 4.23 (q, J=7Hz, 2H), 4.05 (m, 2H), 3.27 (m, 2H), 2.59 (s, 3H), 2.00 (m, 2H), 1.72 (m, 3H), 1.46 (s, 9H), 1.33 (t, J=7Hz, 3H).

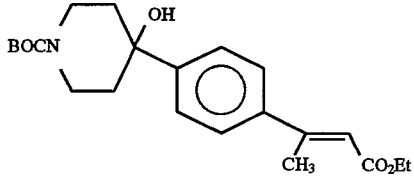

Ethyl 3-[4-(N-BOC-hydroxypiperidin-4-yl)phenyl]butyrate (12-2)

A mixture of 12-1 (400 mg, 1.0 mmoles), 10% Pd/C (160 mg), and CH$_3$OH (5 mL) was stirred at ambient temperature under a hydrogen atmosphere for 3.0 hours. The reaction mixture was filtered through a celite pad and the filtrate concentrated to give 12-2 as a yellow oil. R$_f$ 0.33 (silica, 30% EtOAc/hexanes).

$^1$H NMR (300 MHz, CDCl$_3$) δ 7.45-7.20 (m, 4H), 4.10 (q, J=7hz, 2H), 4.05 (m, 2H), 3.30 (m, 3H), 2.60 (m, 2H), 2.00 (m, 2H), 1.74 (m, 2H), 1.60 (m, 2H), 1.46 (s, 9H), 1.32 (d, J=7Hz, 3H), 1.20 (t, J=7Hz, 3H).

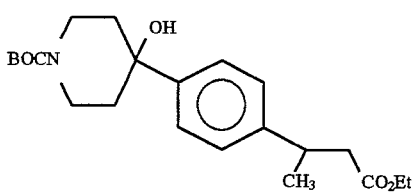

3-[4-(N-BOC-Hydroxypiperidin-4-yl)phenyl]butyric Acid (12-3)

A mixture of 12-2 (400 mg, 1.0 mmoles), 1N NaOH (4 mL, 4.0 mmoles), and CH$_3$OH (5 mL) was stirred at ambient temperature for 4.0 hours. The reaction mixture was acidified with 10% KHSO$_4$ and then extracted with EtOAc (2×). The combined extracts were washed with brine, dried (MgSO$_4$), and then concentrated to give 12-3 as a white solid. R$_f$ 0.66 (silica, 10/0.5/0.5 CH$_2$Cl$_2$/CH$_3$OH/HOAc).

$^1$H NMR (300 MHz, CDCl$_3$) δ 7.42 (m, 2H), 7.23 (m, 2H), 4.04 (m, 2H), 3.28 (m, 2H), 2.63 (m, 2H), 2.00 (m, 2H), 1.72 (m, 2H), 1.48 (s, 9H), 1.35 (d, J=7Hz, 3H).

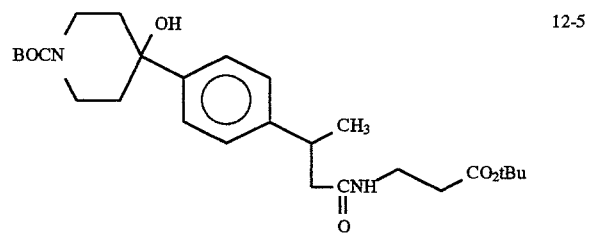

3-[4-(N-BOC-Hydroxypiperidin-4-yl)phenyl]butyryl-β-alanine-tert-butyl Ester (12-5)

To a stirred solution of 12-3 (125 mg, 0.34 mmoles), 12-4 (69 mg, 0.41 mmoles), HOBT (54 mg, 0.41 mmoles), N(i-Pr)$_2$Et (228 mL, 0.82 mmoles), and DMF (2 mL) at −15° C. was added EDC (79 mg, 0.41 mmol) followed by removal of the cooling bath. After 20 hours the reaction mixture was diluted with EtOAc and then washed with H$_2$O, saturated NaHCO$_3$, 10% KHSO$_4$, and brine, dried (MgSO$_4$), and concentrated. Flash chromatography (silica, 60% EtOAc/hexanes) gave 12-5 as a white solid. R$_f$ 0.26 (silica, 60% EtOAc/hexanes).

$^1$H NMR (300 MHz, CDCl$_3$) δ 7.43 (d, J=8Hz, 2H), 7.23 (d, J=8Hz, 2H), 5.88 (m, 1H), 4.03 (m, 2H), 3.32 (m, 5H), 2.41 (d, J=7Hz, 2H), 2.32 (m, 1H), 2.20 (m, 1H), 2.00 (m, 2H), 1.77 (m, 2H), 1.49 (s, 9H), 1.47 (s, 9H), 1.32 (d, J=5Hz, 3H).

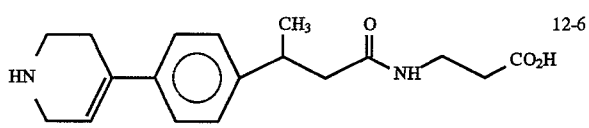

3-[4-(1,2,5,6-Tetrahydropyridin-4-yl)phenyl]butyryl-β-alanine (12-6)

A mixture of 12-5 (120 mg, 0.25 mmoles), CH$_2$Cl$_2$ (1.0 mL), and TFA (1.0 mL) was stirred at ambient temperature for 4.0 hours and then concentrated with azeotropic removal of the excess TFA. Flash chromatography (silica, 10/1/1 ethanol/NH$_4$OH/H$_2$O/gave 12-6 as a white solid. R$_f$ 0.13 (10/1/1 ethanol/NH$_4$OH/H$_2$O).

$^1$H NMR (400 MHz, D$_2$O) δ 7.44 (d, J=8Hz, 2H), 7.27 (d, J=8Hz, 2H), 6.13 (s, 1H), 3.84 (d, J=2Hz, 2H), 3.47 (t, J=6Hz, 2H), 3.25 (m, 1H), 3.17 (m, 2H), 2.77 (m, 2H), 2.55 (m, 1H), 2.42 (m, 1H), 2.28 (m, 1H), 2.11 (m, 1H), 1.27 (d, J=7Hz, 3H).

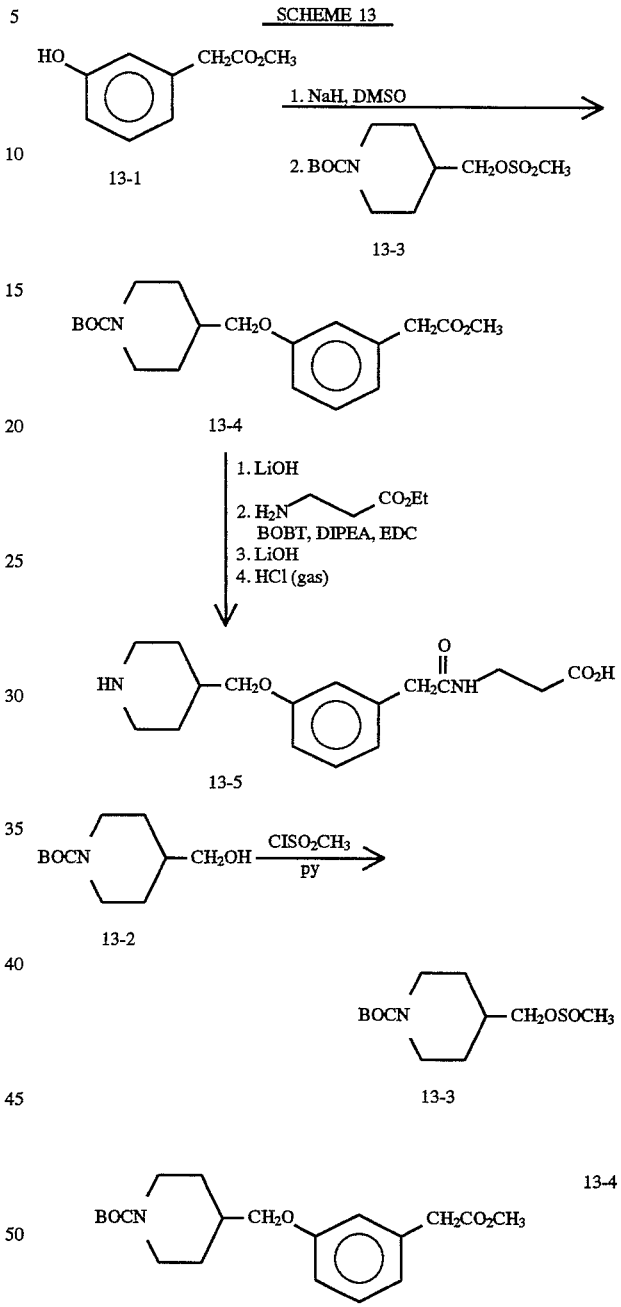

Methyl 3-[(N-BOC-4-Piperidinyl)methyloxy]phenyl Acetate (13-4)

1.57 g (9.48 mmoles) of methyl 3-hydroxy-phenyl acetate (13-1) was dissolved in DMSO (5 ml) and treated with 0.36 g (9.09 mmoles) of 60% NaH (0.36 g, 9.09 mmoles) in oil. N-BOC-4-hydroxymethylpiperidine mesylate (13-3) [prepared from N-Boc-4-hydroxymethylpiperidine (13-2) by treatment with methanesulfonyl chloride and pyridine in methylene chloride] (2.79 g, 9.5 mmoles) was added in one portion and the resulting mixture heated to 60° for 8 hours and stirred at 25° for 48 hours. The reaction mixture was diluted with H$_2$O and Et$_2$O and the organic phase was washed with 1N NaOH solution, brine, then dried (Na$_2$SO$_4$) and concentrated to give 13-4 as an oil.

¹H NMR (300 MHz, CDCl₃): 1.26 (m, 2H), 1.50 (s, 9H), 1.86 (bd, 2H), 1.97 (m, 1H), 2.75 (dt, 2H), 3.60 (s, 3H), 3.70 (s, 3H), 3.80 (d, 2H), 4.08 (bd, 2H), 6.84 (m, 3H), 7.25 (dd, 1H) ppm.

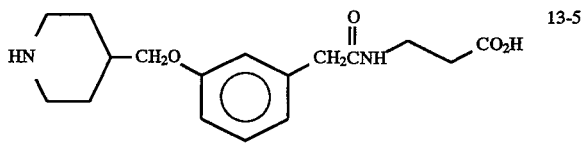

3-[(4-Piperidinyl)methyloxy]-N-(2-carboxyethyl)phenyl Acetamide (13-5)

1.0 g (2.75 mmoles) 13-4 was treated with LiOH (8.25 ml of 1N) in 50 ml H₂O and 50 ml THF at 25° for 3 hours. The reaction mixture was then acidified to pH 5.5 with citric acid, concentrated and extracted with ethyl acetate. The organic extract was dried (Na₂SO₄) and concentrated to give the desired acid (13-6).

¹H NMR (partial) (300 MHz, CDCl₃): 1.25 (m, 2H), 1.24 (s, 9H), 2.75 (dt, 2H), 3.60 (s, 2H), 3.80 (d, 2H) ppm.

This acid (0.35 g, 1.0 mmoles) was dissolved in DMF (3 ml) and treated sequentially with 0.36 g (2.0 mmoles) β-alanine ethyl ester.HCl, 0.23 g (0.15 mmoles) HOBT (1.5 mmoles), DIEA (0.53 ml, 3.0 mmoles), and 0.288 g (1.5 mmoles) EDC. This mixture was stirred for 4 hours, diluted with H₂O and EtOAc and the organic phase was washed with 10% citric acid, saturated NaHCO₃, H₂O, brine, dried (Na₂SO₄) and concentrated. The resulting oil was treated with LiOH (2.5 ml of 1N aqueous solution) as described for 13-4 to provide the desired acid. This was dissolved in EtOAc (60 ml), cooled to −15° and treated with HCl gas for 10 minutes. The solvent was removed to give 13-5 as a white powder.

¹H NMR (300 MHz, d₆-DMSO): 1.48 (m, 2H), 1.80 (m, 2H), 2.08 (m, 1H), 2.38 (t, 2H), 2.89 (dt, 2H), 3.25 (m, 4H), 3.35 (s, 2H), 3.82 (d, 2H), 6.80 (m, 3H), 7.20 (t, 1H) ppm.

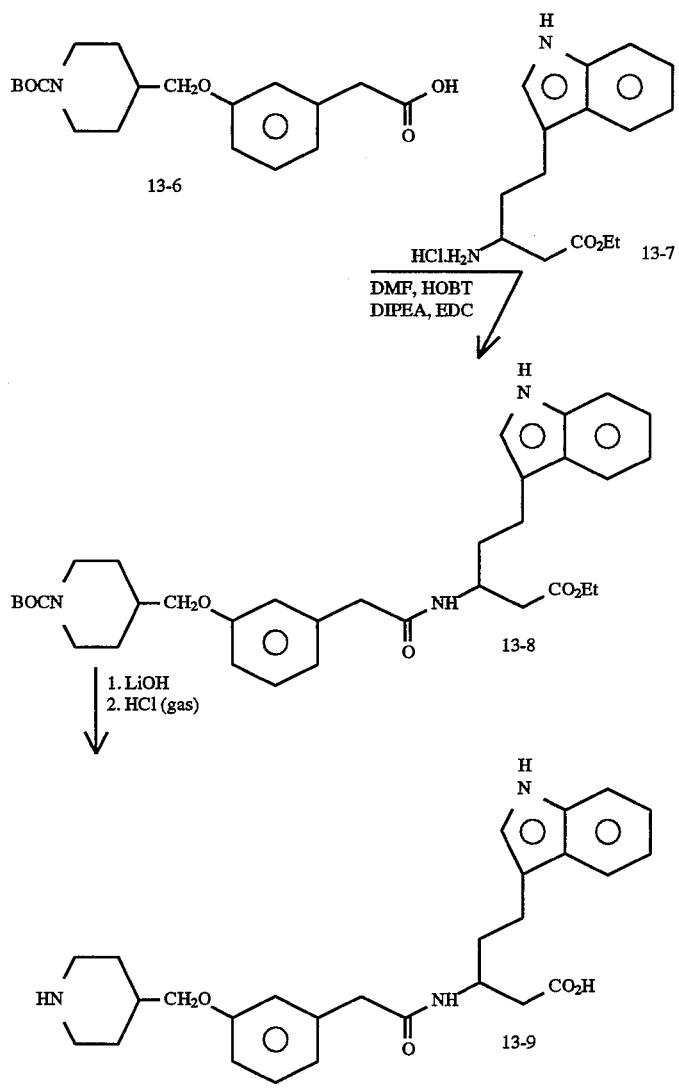

3-[(N-BOC-4-Piperidinyl)methyloxy]-N-[ethyl 3-(2-Indol-3-yl)ethyl)propionate]phenyl Acetamide (13-8)

Treatment of 13-6 (0.35 g, 1.0 mmoles) in DMF (3 ml) as described for 13-5 employing ethyl 3-[2-(indol-3-yl)ethyl]

propionate (13-7) (prepared as in Example 36, page 40, of European Publication 478,362, published Apr. 1, 1992) provided the desired adduct 13-8.

3-[(4-Piperidinyl)methyloxy]-N-[3-(2-indol-3-yl) ethyl Propionic Acid]-phenyl Acetamide (13-9)

Treatment of 13-8 with LiOH.H$_2$O and subsequently with HCl (gas) as described for 13-5 provided 13-9 as a white solid.

$^1$H NMR (partial) (300 MHz, d$_6$-DMSO) 1.40 (m, 2H), 1.65 (d, 2H), 1.82 (m, 2H), 2.30 (m, 2H), 3.40 (s, 2H), 6.80 (m, 2H), 6.92 (m, 2H), 7.05 (m, 2H), 7.18 (t, 1H), 7.30 (d, 1H), 7.40 (d, 1H), 8.14 (d, 1H) ppm.

Methyl 6-[2-(N-BOC-4-Piperidinyl)ethyloxy] nicotinate (14-2)

To a stirred solution of 1-4 (2.0 g, 8.8 mmol) in THF (40 mL) at 0° C. was added NaH (350 mg, 60% dispersion in mineral oil). After 20 min, 14-1 (750 mg, 4.4 mmol, available from Lancaster Chemical Co.) was added, followed by heating to reflux for 2 h. The cooled reaction mixture was concentrated then purified by flash chromatography (silica, 20% EtOAc/hexanes) to give 14-2 (650 mg) as a white solid R$_f$ 0.25 (silica, 20% EtOAc/hexanes).

$^1$H NMR (300 MHz, CDCl$_3$) δ 8.83 (m, 1H), 8.17 (m, 1H), 6.77 (m, 1H), 4.37 (t, J=7Hz, 2H), 4.10 (m, 2H), 3.91 (s, 3H), 2.70 (m, 2H), 1.80-1.10 (m, 7H), 1.47 (s, 7H).

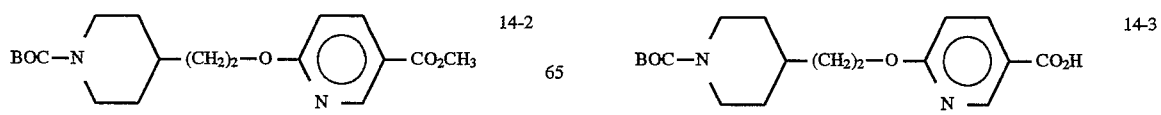

6-[2-(N-BOC-4-Piperidinyl)ethyloxy]nicotinic Acid (14-3)

A solution of 14-2 (650 mg, 1.2 mmol), 1N LiOH (3 mL), and THF (5 mL) was stirred at ambient temperature for 20 h. The reaction mixture was then washed with EtOAc followed by acidification with 5% $KHSO_4$, then extraction with EtOAc. The EtOAc extract was washed with brine, dried ($MgSO_4$) and concentrated to give 14-3 (260 mg) as a white solid. $R_f$ 0.64 (silica, 10:2:2 ($CH_2Cl_2/CH_3OH/AcOH$)).

$^1H$ NMR (300 MHz, $CDCl_3$) δ 8.89 (d, J=2Hz, 1H), 8.21 (dd, J=8 and 2Hz, 1H), 6.78 (d, J=8Hz, 1H), 4.44 (t, J=7Hz, 2H), 4.10 (m, 2H), 2.70 (m, 2H), 1.80-1.10 (m, 7H), 1.46 (s, 9H).

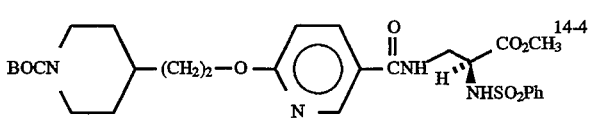

6-[2-(N-BOC-piperidin-4-yl)ethyloxy]-nicotinamide-N-[Methyl 3-(2(S)-phenylsulfonylamino)propionate] (14-4)

Utilizing the procedure for converting 9-3 carboxylic acid to 9-5, 14-3 (100 mg, 0.29 mmol) gave 14-4 (130 mg) as a colorless oil after flash chromatography (silica, 60% EtOAc/hexanes). $R_f$ 0.13 (silica, 60% EtOAc/hexanes).

$^1H$ NMR (300 MHz, $CDCl_3$) δ 8.62 (d, J=2Hz, 1H), 8.03 (dd, J=8 and 2Hz, 1H), 7.55 (m, 5H), 6.80 (d, J=8Hz, 1H), 6.74 (m, 1H), 5.76 (d, J=8Hz, 1H), 4.43 (t, J=7Hz, 2H), 4.10 (m, 2H), 3.65 (s, 3H), 2.70 (m, 2H), 1.80-1.10 (m, 7H), 1.47 (s, 9H).

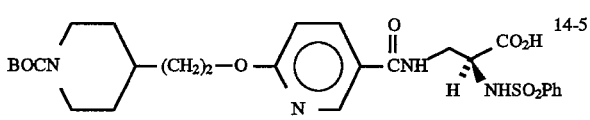

6-[2-(N-BOC-Piperidin-4-yl)ethyloxy]-nicotinamide-N-[3-(2(S)-phenylsulfonylamino) propionic Acid] (14-5)

A solution of 14-4 (120 mg, 0.21 mmol), in 1N NaOH (1 mL), and $CH_3OH$ (1 mL) was stirred at ambient temperature for 1.0 h followed by acidification with 10% $KHSO_4$. The reaction mixture was then extracted with EtOAc and the EtOAc extract washed with brine, dried ($MgSO_4$), and concentrated to give 14-5 (115 mg) as a white solid. $R_f$ 0.48 (10:1:1 $CH_2Cl_2/CH_3OH/AcOH$).

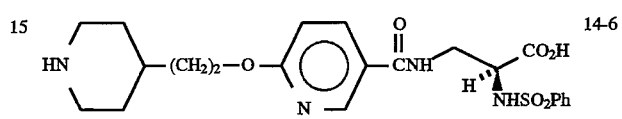

6-[2-(Piperidin-4-yl)ethyloxy]nicotinamide-N-[3-(2(S)-phenylsulfonylamino)propionic Acid] (14-6)

A solution of 14-5 (110 mg, 0.19 mmol), TFA (1.0 mL), and $CH_2Cl_2$ (1.0 mL) was stirred at ambient temperature for 1.0 h. The solution was concentrated and then azeotroped with toluene to remove residual TFA. Flash chromatography (silica, 10:1:1 $EtOH/H_2O/NH_4OH$) gave 14-6 (35 mg) as a white solid. $R_f$ 0.17 (silica, 10:1:1 $EtOH/H_2O/NH_4OH$).

$^1H$ NMR (300 MHz, $D_2O/DCl$) δ 8.46 (s, 1H), 8.44 (m, 1H), 7.78 (m, 1H), 7.42 (m, 5H), 4.57 (t, J=7Hz, 2H), 4.25 (m, 1H), 3.79 (dd, J=14 and 5Hz, 1H), 3.50 (dd, J=14 and 9Hz, 1H), 3.40 (m, 2H), 2.97 (m, 2H), 2.05-1.80 (m, 5H), 1.45 (m, 2H).

SCHEME 15

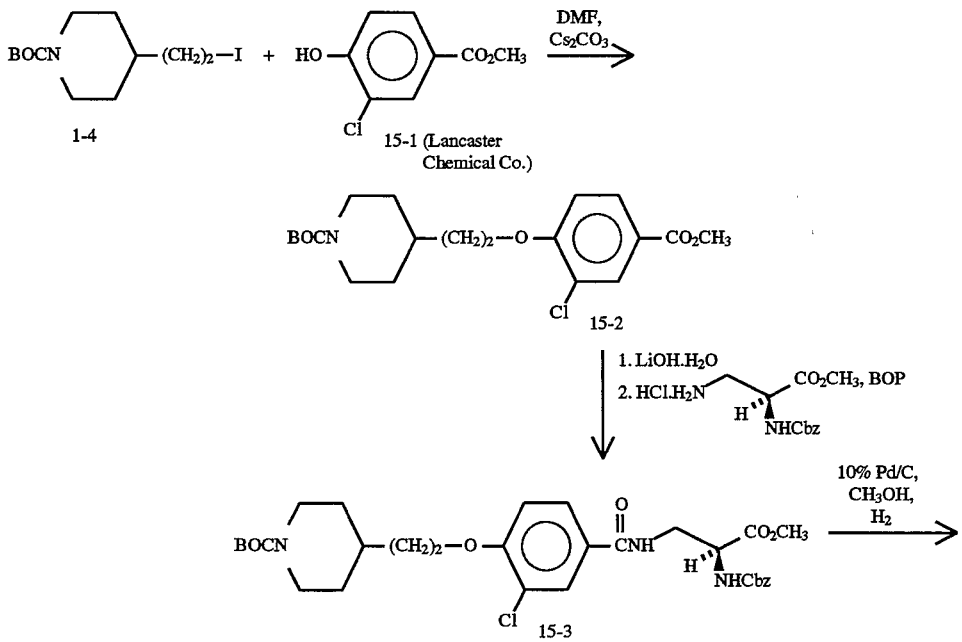

-continued
SCHEME 15

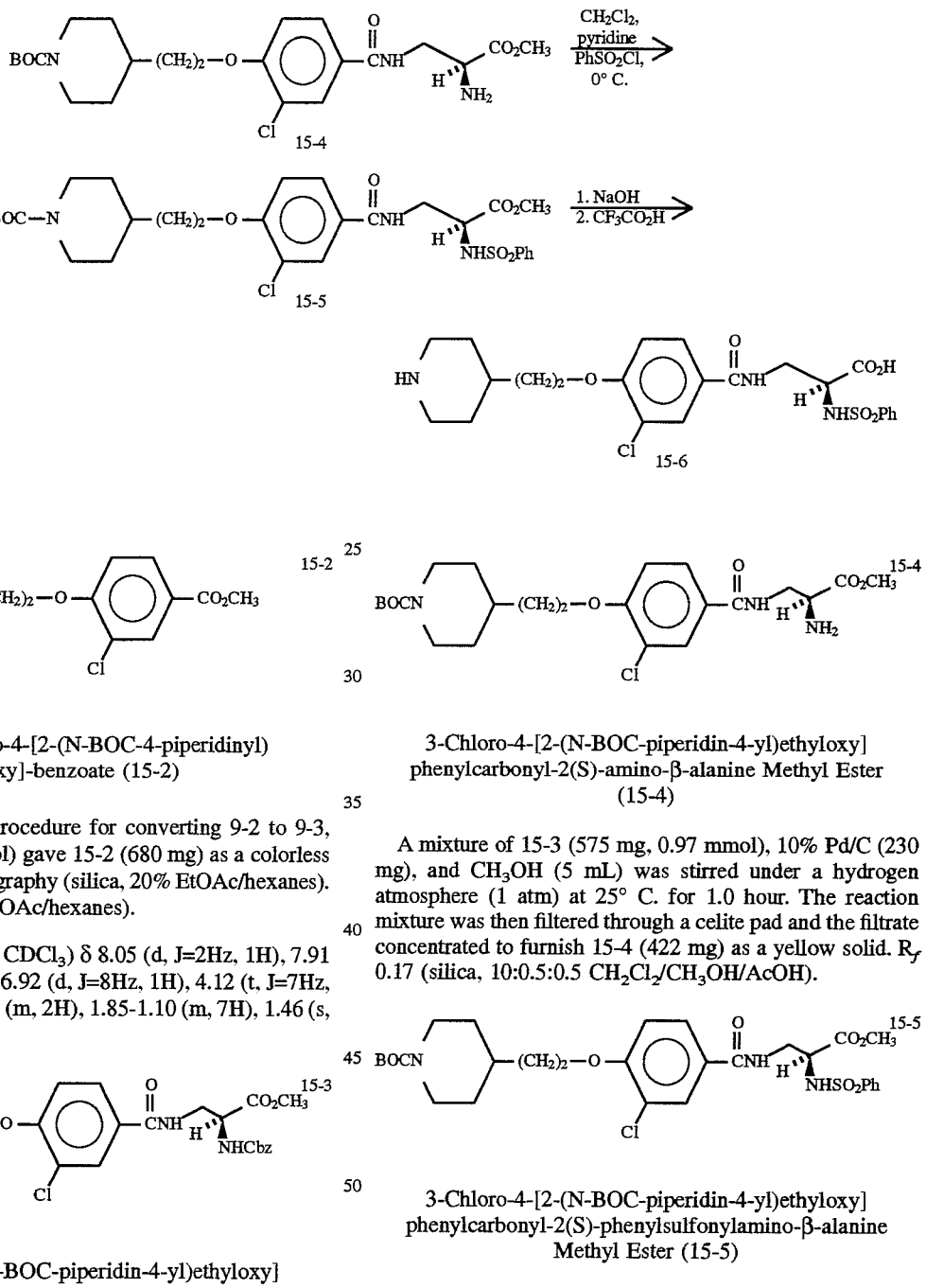

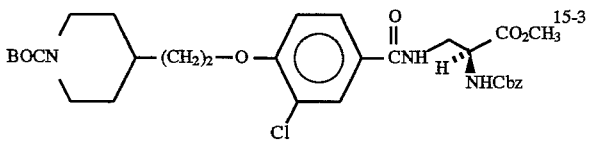

Methyl 3-Chloro-4-[2-(N-BOC-4-piperidinyl)
ethyloxy]-benzoate (15-2)

Utilizing the same procedure for converting 9-2 to 9-3, 15-1 (363 mg, 1.9 mmol) gave 15-2 (680 mg) as a colorless oil after flash chromatography (silica, 20% EtOAc/hexanes). R$_f$ 0.51 (silica, 20% EtOAc/hexanes).

$^1$H NMR (300 MHz, CDCl$_3$) δ 8.05 (d, J=2Hz, 1H), 7.91 (dd, J=8 and 2Hz, 1H), 6.92 (d, J=8Hz, 1H), 4.12 (t, J=7Hz, 2H), 4.09 (m, 2H), 2.71 (m, 2H), 1.85-1.10 (m, 7H), 1.46 (s, 9H).

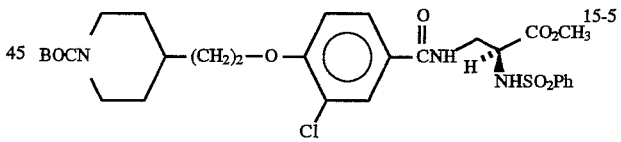

3-Chloro-4-[2-(N-BOC-piperidin-4-yl)ethyloxy]
phenylcarbonyl-2(S)-benzyloxycarbonylamino-β-
alanine Methyl Ester (15-3)

Utilizing the same procedure for converting 9-3 to 9-5, 15-2 (650 mg, 1.7 mmol) gave 15-3 (630 mg) as a white solid after flash chromatography (silica, 50% EtOAc/hexanes). R$_f$ 0.24 (silica, 50% EtOAc/hexanes).

$^1$H NMR (300 MHz, CDCl$_3$) δ 7.85 (d, J=2Hz, 1H), 7.80 (dd, J=8 and 2Hz, 1H), 7.34 (m, 5H), 6.96 (d, J=8Hz, 1H), 5.13 (m, 2H), 4.50 (m, 1H), 4.14 (t, J=7Hz, 2H), 4.08 (m, 2H), 4.78 (s, 3H), 3.46 (m, 2H), 2.74 (m, 2H), 1.80 (m, 5H), 1.46 (s, 9H), 1.23 (m, 2H).

3-Chloro-4-[2-(N-BOC-piperidin-4-yl)ethyloxy]
phenylcarbonyl-2(S)-amino-β-alanine Methyl Ester
(15-4)

A mixture of 15-3 (575 mg, 0.97 mmol), 10% Pd/C (230 mg), and CH$_3$OH (5 mL) was stirred under a hydrogen atmosphere (1 atm) at 25° C. for 1.0 hour. The reaction mixture was then filtered through a celite pad and the filtrate concentrated to furnish 15-4 (422 mg) as a yellow solid. R$_f$ 0.17 (silica, 10:0.5:0.5 CH$_2$Cl$_2$/CH$_3$OH/AcOH).

3-Chloro-4-[2-(N-BOC-piperidin-4-yl)ethyloxy]
phenylcarbonyl-2(S)-phenylsulfonylamino-β-alanine
Methyl Ester (15-5)

To a stirred solution of 15-4 (375 mg, 0.82 mmol), CH$_2$Cl$_2$ (4 mL), and pyridine (0.2 mL, 2.4 mmol) at 0° C. was added phenylsulfonyl chloride (435 mg, 2.5 mmol) followed by removal of the cooling bath. After 20 hours the reaction mixture was diluted with EtOAc and then washed with H$_2$O, saturated NaHCO$_3$, 10% KHSO$_4$ and brine, dried (MgSO$_4$), and concentrated. Flash chromatography (silica, 60% EtOAc/hexanes gave 15-5 (315 mg) as a white solid. R$_f$ 0.26 (silica, 60% EtOAc/hexanes).

$^1$H NMR (300 MHz, CDCl$_3$) δ 7.90-7.50 (m, 7H), 6.92 (d, J=8Hz, 1H), 6.61 (m, 1H), 5.75 (m, 1H), 4.10 (t, J=7Hz, 2H), 4.10 (m, 3H), 3.87 (m, 1H), 3.69 (m, 1H), 3.62 (s, 3H), 2.72 (m, 2H), 1.75 (m, 5H), 1.46 (s, 9H), 1.20 (m, 2H).

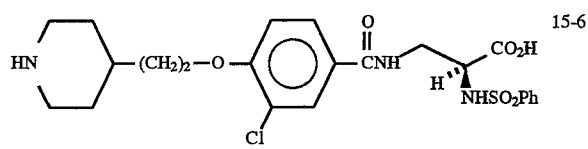
3-Chloro-4-[2-(piperidin-4-yl)ethyloxy]
phenylcarbonyl-2(S)-phenylsulfonylamino-β-alanine
(15-6)
Utilizing the procedure for convening 9-5 to 9-6, 15-5 (275 mg, 0.46 mmol) gave 15-6 (85 mg) after flash chromatography (silica, 10:1:1 ethanol/H$_2$O/NH$_4$OH). R$_f$ 0.39 (silica, 10:1:1 ethanol/H$_2$O/NH$_4$OH).
$^1$H NMR (300 MHz, DCl/D$_2$O) δ 7.70-7.00 (m, 8H), 4.23 (m, 3H), 3.75 (dd, J=14 and 4Hz, 1H), 3.40 (m, 3H), 2.97 (m, 2H), 2.10-1.80 (m, 5H), 1.46 (m, 2H).
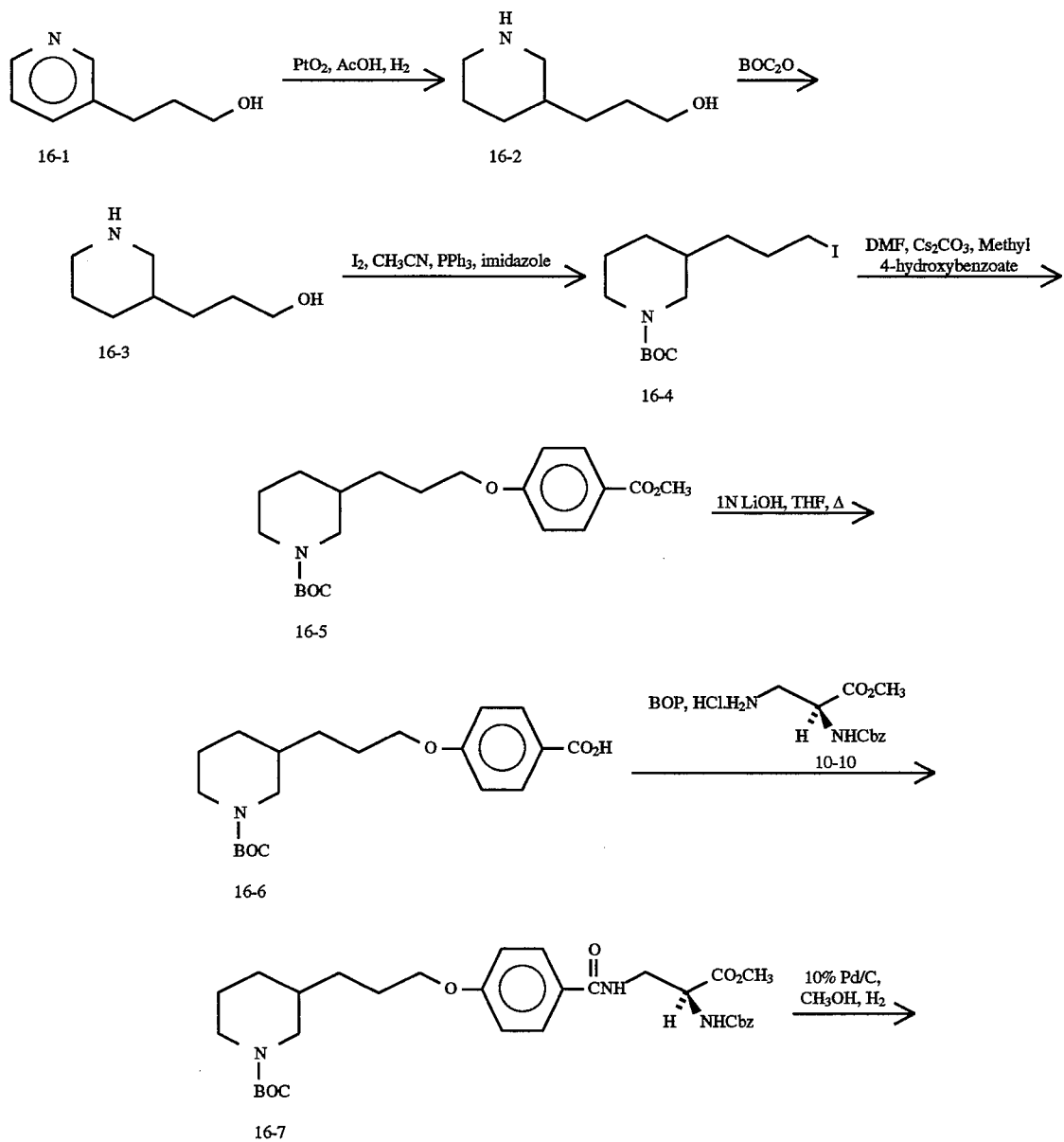
SCHEME 16

-continued
SCHEME 16

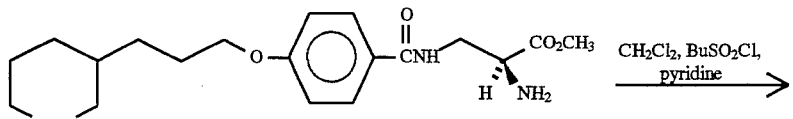

16-8

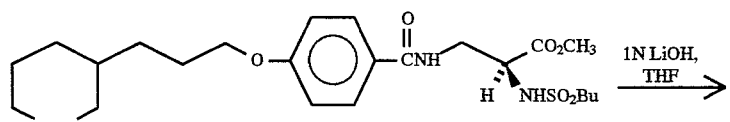

16-9

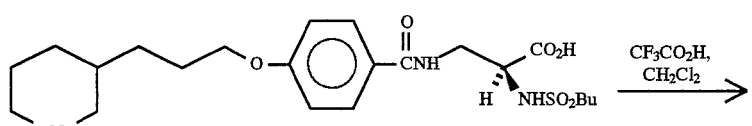

16-10

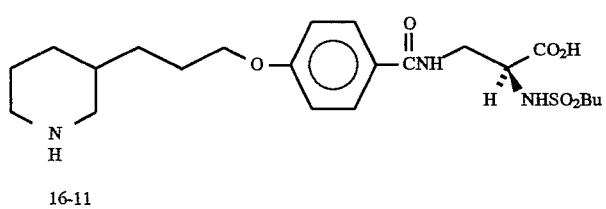

16-11

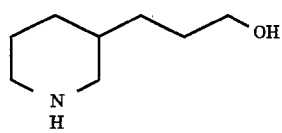

3-Piperidin-3-ylpropanol (16-2)

A mixture of 16-1 (Aldrich Co.) (25 g, 0.18 mmol), PtO₂ (2 g), and AcOH (150 mL) was shaken on the Parr apparatus at 50 PSI for 8 h. The reaction was filtered through a celite pad to give 16-2 (~25 g) as a yellow oil after solvent evaporation. R_f 0.31 (silica, 4:1:1 CH₂Cl₂/CH₃OH/AcOH).

¹H NMR (400 MHz, DMSO) δ 3.32 (m, 2H), 3.19 (m, 2H), 2.62 (m, 1H), 2.37 (m, 1H), 1.80-1.00 (m, 9H).

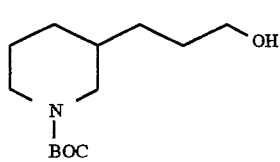

3-N-BOC-Piperidin-3-ylpropanol (16-3)

To a stirred solution of 16-2 (25 g, ~0.18 mol), NEt₃ (30 mL, 0.22 mol), and DMF (500 mL) at 0° C. was added BOC₂O (47 g, 0.22 mmol). After 4 h the reaction mixture was diluted with EtOAc and then washed with 10% KHSO₄, H₂O, sat. NaHCO₃, and brine, dried (MgSO₄), and concentrated to give 16-3 as a yellow oil which was used directly for the next reaction. R_f 0.55 (silica, 50% EtOAc/hexanes).

3-N-BOC-Piperidin-3-ylpropyl iodide (16-4)

To a stirred solution of crude 16-3 (~45 g, 0.18 mol), CH₃CN (500 mL), imidazole (18 g, 0.27 mol), and PPh₃ (52 g, 0.2 mol) at ambient temperature was added iodine (50 g, 0.2 mol). After 20 h the reaction mixture was diluted with EtOAc and then washed with 10% KHSO₄, sat. Na₂SO₃, H₂O, and brine, dried (MgSO₄), and concentrated. Flash chromatography (silica, 10% EtOAc/hexanes) gave 16-4 (12 g) as an oil. R_f 0.95 (silica, 50% EtOAc/hexanes).

¹H NMR (400 MHz, CDCl₃) δ 3.87 (m, 2H), 3.15 (t=7 Hz, 2H), 2.77 (m, 2H), 1.90–1.00 (m, 9H), 1.45 (s, 9H).

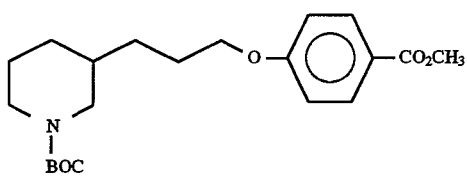

Methyl 4-[3-(N-BOC-piperidin-3-yl)propyloxy]benzoate (16-5)

A mixture of 16-4 (1.0 g, 3 mmol), methyl 4-hydroxybenzoate (Aldrich)(0.46 g, 3 mmol), Cs$_2$CO$_3$ (2.9 g, 9 mmol), and DMF (30 mL) was stirred at 60° C. for 20 h. The cooled reaction mixture was diluted with EtOAc and then washed with H$_2$O (2×) and brine, dried (MgSO$_4$), and concentrated. Flash chromotography (silica, 15% EtOAc/hexanes) gave 16-5 (0.75 g) as an oil. R$_f$ 0.45 (silica, 30% EtOAc/hexanes).

$^1$H NMR (300 MHz, DCDl$_3$) δ 7.97 (d, J=9 Hz, 2H), 6.89 (d, J=9 Hz, 2H), 4.00 (t, J=7 Hz, 2H), 3.95 (m, 2H), 3.88 (s, 3H), 2.77 (m, 2H), 1.90–1.00 (m, 9H), 1.45 (s, 9H).

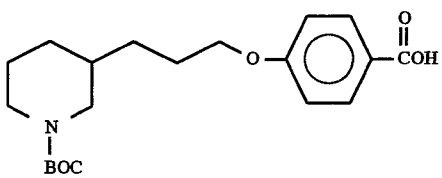

4-[3-(N-BOC-Piperidin-3-yl)propyloxy]benzoic acid (16-6)

A mixture of 16-5 (0.75 g, 2 mmol), THF (30 ml) and 1N LiOH (10 mL) was heated at reflux for 7 h. The cooled reaction mixture was diluted with EtOAc and 10% KHSO$_4$. The organic portion was then washed with brine, dried (MgSO$_4$) and concentrated to give 16-6 (740 mg) as a white solid. R$_f$ 0.86 (silica, EtOAc).

$^1$H NMR (400 MHz, CDCl$_3$) δ 8.03 (d, J=8 Hz, 2H), 6.95 (d, J=8 Hz, H), 4.00 (t, J=7 Hz, 2H), 3.90 (m, 2H), 2.77 (m, 1H), 2.50 (m, 1H), 1.85 (m, 4H), 1.63 (m, 2H), 1.45 (s, 9H), 1.42 (m, 2H), 1.10 (m, 1H).

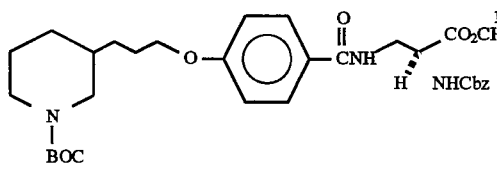

4-[3-(N-BOC-Piperidin-3-yl)propyloxy]-N-[methyl 3-(2-(S)-benzyloxy-carbonylamino)propionyl)benzamide (16-7)

To a stirred solution of 16-6 (410 mg, 1.1 mmol), 10-10 (308 mg, 1.1 mmol), NMM (0.3 mL, 1.3 mmol), and CH$_3$CN (11 mL) at ambient temperature was added BOP reagent (0.6 g, 1.3 mmol). After 20 h, the reaction mixture was diluted with EtOAc and then washed with 10% KHSO$_4$, sat. NaHCO$_3$, H$_2$O, and brine, dried (MgSO$_4$), and concentrated. Flash chromotography (silica, 60% EtOAc/hexanes) gave 16-7 (430 mg) as an oil. R$_f$ 0.82 (silica, 50% EtOAc/hexanes).

$^1$H NMR (400 MHz, CDCl$_3$) δ 7.70 (d, J=9 Hz, 2H), 7.33 (m, 5H), 6.88 (d, J=9 Hz, 2H), 7.33 (m, 5H), 6.88 (d, J=9 Hz, 2H), 6.69 (m, 1H), 5.97 (m, 1H), 5.11 (0.5, 2H), 4.53 (m, 1H), 3.98 (t, J=7 Hz, 2H), 3.93–3.80 (m, H), 3.76 (s, 3H), 2.77 (m, 1H), 2.50 (m, 1H), 1.80–1.00 (m, 9H), 1.45 (s, 9H).

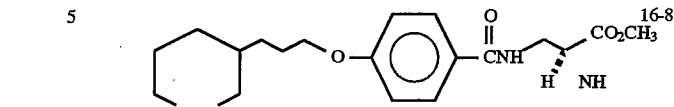

4-[3-(N-BOC-Piperidin-3-yl)propyloxy]-N-[methyl 3-(2(S)-amino)-propionyl)]benzamide (16-8)

A mixture of 16-7 (430 mg, 0.72 mmol), 10% Pd/C, and CH$_3$OH (7 mL) was stirred at ambient temperature under a hydrogen atmosphere (1 atm) for 20 h. The reaction mixture was then filtered through a celite pad and the filtrate concentrated to give 16-8 (333 mg) as an oil. R$_f$ 0.75 (silica, 9:1:1 CH$_2$Cl$_2$/CH$_3$OH/AcOH).

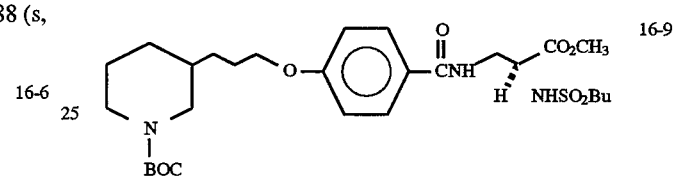

4-3-(N-BOC-Piperidin-3-yl)propyloxy]-N-[methyl 3-(2-(S)-butyl-sulfonylamino)propionyl]benzamide (16-9)

To a stirred solution of 16-8 (333 mg, 0.72 mmol), in CH$_2$Cl$_2$ (7 mL) at 0° C. was added pyridine (0.12 mL, 1.4 mmol) and n-butylsulfonyl chloride (0.19 mL, 1.4 mmol), followed by removal of the cooling bath. After 20 h, the reaction mixture was diluted with EtOAc and then washed with 10% KHSO$_4$, sat. NaHCO$_3$. H$_2$O and brine, dried (MgSO$_4$), and concentrated. Flash chromatography (silica, 60% EtOAc/hexanes) gave 16-9 (300 mg) as a colorless oil. R$_f$ 0.15 (silica, 50% EtOAc/hexanes).

$^1$H NMR (400 MHZ, CDCl$_3$) δ 7.74 (d, J=9 Hz, 2H), 6.89 (d, J=9 Hz, H), 6.72 (m, 1H), 5.66 (m, 1H), 4.33 (m, 1H), 3.98 (t, J=7 Hz, 2H), 3.90 (m, 2H), 3.82 (s, 3H), 3.77 (m, 2H), 3.03 (m, 2H), 2.78 (m, 1H), 2.50 (m, 1H), 1.90–1.00 (m, 9H), 1.45 (s, 9H), 0.91 (t, J=7 Hz, 3H).

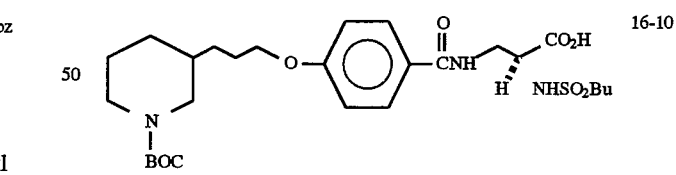

4-[3 -(N-BOC-Piperidin-3-yl)propyloxy]-N-[3-(2(S) -butylsulfonyl-amino)propionic acid]benzamide (16-10)

A solution of 16-9 (300 mg, 0.5 mmol), THF (5 mL), and 1N LiOH (1.5 mL, 1.5 mmol) was stirred at ambient temperature for 30 min. The reaction mixture was acidified with 10% KHSO$_4$, and then extracted with EtOAc. The EtOAc extract was washed with brine, dried (MgSO$_4$), and concentrated to give 16-10 (273 mg) as an oil. R$_f$ 0.87 (silica, 9:1:1 CH$_2$Cl$_2$/CH$_3$OH/AcOH.

$^1$H NMR (400 MHz, CDCl$_3$) δ 7.75 (d, J=9 Hz, 2H), 7.14 (m, 1H), 6.89 (d, J=9 Hz, 2H), 5.88 (m, 1H), 4.24 (m, 1H), 3.98 (t, J=7 Hz, 2H), 4.00–3.70 (m, 4H), 3.05 (m, 2H), 2.60 (m, 2H), 1.90–1.00 (m, 9H), 1.45 (s, H), 0.89 (t, J=7 Hz, 3H).

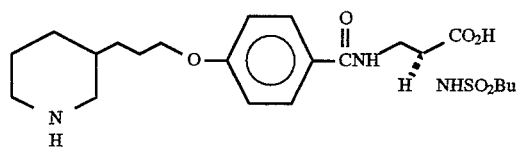

4-[3-(Piperidin-3-yl)propyloxy]-N-[3-(2(S)-butylsulfonylamino)-propionic acid]benzamide (16-11)

A solution of 16-10 (273 mg, 0.48 mmol), TFA (2.4 mL), and CH$_2$Cl$_2$ was stirred at 25° C. for 1.0 h. Concentration followed by flash chromatography (silica, 10:1:1 ethanol/NH$_4$OH/H$_2$O) gave 16-11 (70 mg) as a white solid.

$^1$H NMR (400 MHz, D$_2$O) δ 7.63 (d, J=9 Hz, 2H), 6.90 (d, J=9 Hz, 2H), 4.22 (m, 1H), 3.97 (t, J=7 Hz, 2H), 3.70 (m, 1H), 3.44 (m, 1H), 3.20 (m, H), 2.96 (m, 2H), 2.72 (m, 1H), 2.50 (m, 1H), 1.80–1.00 (m, 9H), 0.58 (t, J=7 Hz, 3H).

4-[2-(N-BOC-Piperidin-4-yl)ethyloxy]phenylcarbonyl-2(S)-hydroxy-β-alanine methyl ester (17-2)

A solution of 9-3 (60mg, 0.18 mmol), 1% 1 (Pol. J. Chem 9, 53, 1533–9) (28mg, 0.18 mmol), NMM (78 ml, 0.72 mmol), and CH$_3$CN (1 mL) at ambient temperature was treated with BOP (118 mg, 0.27 mmol). After 72 h, the reaction mixture was diluted with EtOAc and then washed with H$_2$O, sat. NaHCO$_3$, 10% KHSO$_4$, and brine, dried (MgSO$_4$), and concentrated. Flash chromatography (silica, 80% EtOAc/hexanes) gave 17-2 (47 mg) as a colorless oil. R$_f$ 0.18 (silica, EtOAc/hexanes).

$^1$H NMR (300 MHz, CDCl$_3$) δ 7.72 (d, J=8 Hz, 2H), 6.92 (d, J=8 Hz, H), 6.45 (m, 1H), 4.42 (m, 1H), 4.13 (m,1H), 4.08 (m, 4H), 2.70 (m, H), 1.80–1.10 (m, 7H), 1.46 (s, 9H).

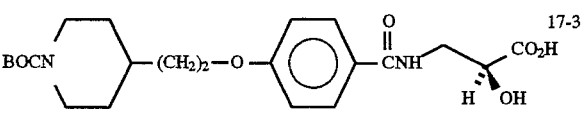

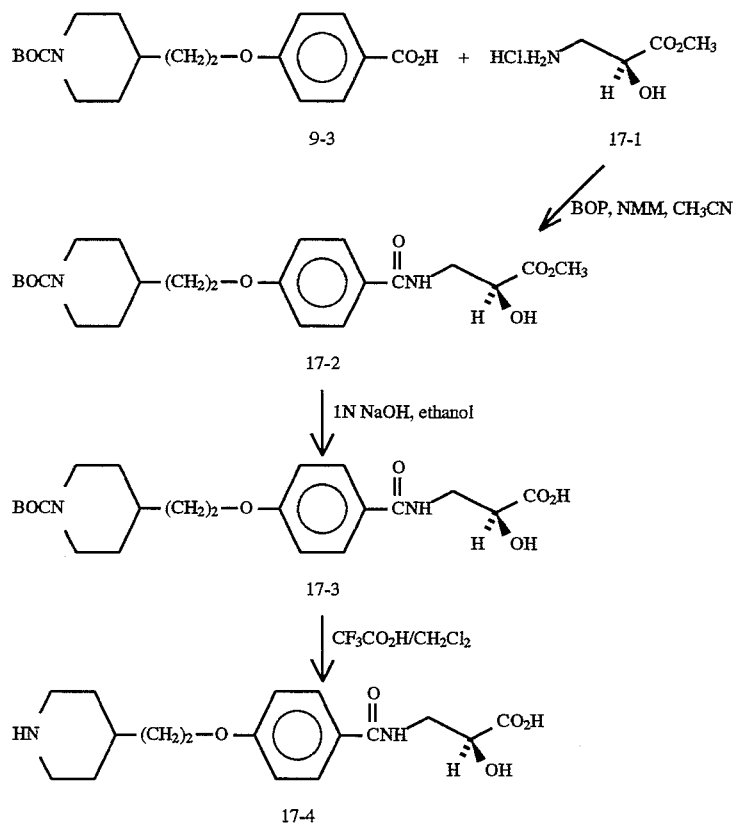

4-[2-(N-BOC-piperidin-4-yl)ethyloxy]phenylcarbonyl-2(S)-hydroxy-β-alanine (17-3)

A solution of 17-2 (45 mg, 0.10 mmol), 1N NaOH (400 L), and ethanol (500 μl) was stirred at ambient temperature for 1.0 h. The reaction was acidified with 10% KHSO$_4$ and then extracted with EtOAc. The EtOAc portion was washed with brine, dried (MGSO$_4$), and concentrated to give 17-3 (45 mg) as a white solid. R$_f$ 0.26 (silica, 10:1:1 CH$_2$Cl$_2$/CH$_3$OH/AcOH).

¹H NMR (400 MHz, CDCl₃) δ 7.70 (m, 1H), 7.60 (d, J=8 Hz, 2H), 6.63 (d, J=8 Hz, 2H), 4.20–4.00 (m, 5H), 3.70–3.60 (m, 2H), 2.65 (m, 2H), 1.80–1.00 (m, 7H), 1.46 (s, 9H).

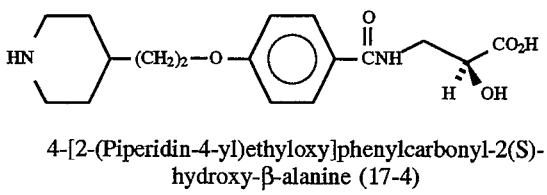

4-[2-(Piperidin-4-yl)ethyloxy]phenylcarbonyl-2(S)-hydroxy-β-alanine (17-4)

A solution of 17-3 (45 mg, 0.10 mmol), TFA (1 mL), and CH₂Cl₂ (1 mL) was stirred at ambient temperature for 1.0 h. Concentration and flash chromatography (silica, 10:1:1 etha-nol H₂O/NH₄OH) gave 17-4 (28 mg) as a white solid. R_f 0.17 (10:1:1 ethanol) H₂O/NH₄OH).

¹H NMR (400 MHz, DCl/D₂O) δ 7.73 (d, J=8 Hz, 2H), 7.03 (d, J=8 Hz, 2H), 4.48 (t, J=7 Hz, 1H), 4.17 (t, J=7 Hz, 2H), 3.73 (m, 2H), 3.40 (m, 2H), 2.95 (m, 2H), 2.00 (m, 2H), 1.87 (m, 1H), 1.79 (m, 2H), 1.46 (m, 2H).

-continued
SCHEME 18

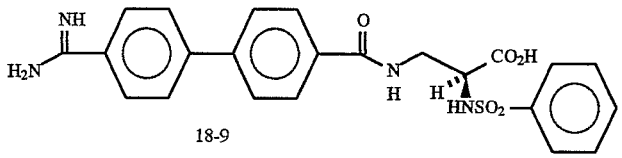

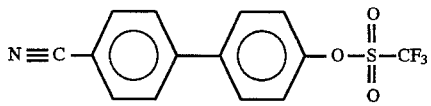

4'-Trifluorosulfonyloxy-4-biphenylnitrile (18-2)

A suspension of 4'-hydroxy-4-biphenylnitrile (18-1) (Aldrich) (5.0 g, 25.6 mmol) in 200 mL $CH_2Cl_2$ was cooled to –40° C. and treated with 2,6 lutidine (4.5 mL, 38.4 mmol), 4-dimethylamino-pyridine (0.625 g, 5.12 mmol) and trifluoromethanesulfonic anhydride (6.5 mL, 38.4 mmol). The mixture became homogeneous after warming to room temperature and was stirred for three hours, then concentrated, adsorbed onto silica and chromatographed eluting with EtOAc/Hexanes to yield 18-2 as a white solid. $R_f$ 0.3 (10% EtOAc/Hexanes).

$^1$H NMR (400 MHz, $CDCl_3$) δ 7.8 (d, 2H), 7.6 (m, 4H), 7.4 (d, 2H).

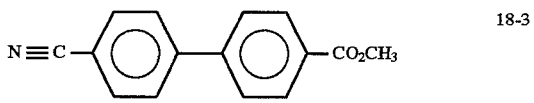

Methyl 4'-Cyano-4-biphenylcarboxylate (18-3)

A solution of 18-2 (8 g, 24.4 mmole) in 60 mL MeOH and 35 mL DMSO was treated with triethylamine (7.8 mL, 56 mmol), Palladium Acetate (0.164 g, 0.73 mmol) and 1,3-Bis (diphenyl phosphino)propane (0.3 g, 0.73 mmol). Carbon monoxide was bubbled through the solution while the reaction was heated to reflux for five hours. The solvents were removed in vacuo and the residue purified by flash chromatography on silica gel eluting with 10% EtOAc/Hexanes to give 18-3. $R_f$ 0.19 (10% EtOAc/Hex).

$^1$H NMR (300 MHz, $CDCl_3$) δ 8.2 (d, 2H), 7.8 (m, 4H), 7.7 (d, 2H).

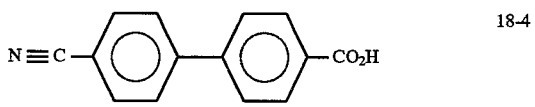

4'-Cyano-4-biphenylcarboxylic acid (18-4)

Compound 18-3 (3.4 g, 15.1 mmole), and LiOH•$H_2O$ (3.1 g, 75.5 mmol) were dissolved in THF/MeOH/$H_2O$ (30 mL/30 mL/30 mL) and stirred at room temperature overnight. The solution was diluted with EtOAc and washed with 10% $KHSO_4$. The organic layer was washed with brine, dried over $MgSO_4$, filtered and concentrated to yield 18-4 as a white solid.

$^1$H NMR (400 MHz, $CD_3OD$) δ 8.1 (d, 1H), 7.7 (m, 4H), 7.6 (d, 2H).

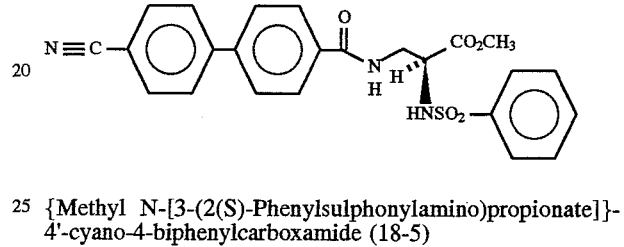

{Methyl N-[3-(2(S)-Phenylsulphonylamino)propionate]}-4'-cyano-4-biphenylcarboxamide (18-5)

A slurry of 18-4 (1.5 g, 7.1 mmole) and 9-12 (2.0 g, 7.1 mmol) in 30 mL acetonitrile was treated with BOP (3.1 g, 7.1 mmol) at 0° C. NMM (1.5 mL, 14.2 mmol) was added and the slurry was stirred for 16 hours, then diluted with EtOAc and washed successively with $H_2O$, 10% $KHSO_4$, $H_2O$, sat. $NaHCO_3$ and brine. Concentration of the organic layer and chromatography of the residue on silica gel (eluting with 60% EtOAc/Hexanes) gave 18-5 as a white solid. $R_f$ 0.62 (70% EtOAc/Hexanes).

$^1$H NMR (400 MHz, $CDCl_3$) δ 7.9 (d, 2H), 7.85 (d, 2H), 7.75 (d, 2H), 7.70 (d, 2H), 7.65 (d, 2H), 7.55 (m, 1H), 7.5 (m, 2H), 4.1 (m, 1H), 3.85 (dd, 1H), 3.7 (dd, 1H), 3.6 (s, 3H).

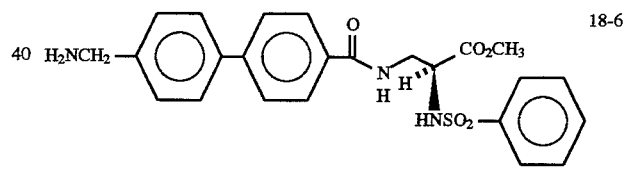

{Methyl N-[3-(2(S)-Phenylsulphonylamino)propionate]}-4'-amino-methyl-4-biphenylcarboxamide (18-6)

A solution of 18-5 (0.5 g, 1.11 mmol) in 10 mL MeOH and 0.55 mL concentrated HCl was treated with 10% Pd/C (0.1 g) and hydrogenated under balloon pressure for 16 hours. The solution was filtered through celite and concentrated to give 18-6 as a white solid.

$^1$H NMR (400 MHz, $CD_3OD$) δ 7.85 (m, 4H), 7.75 (m, 4H), 7.6 (d, 2H), 7.5 (m, 3H), 4.25 (m, 1H), 4.2 (s, 2H), 3.8–3.5 (m, 2H), 3.5 (s, 3H).

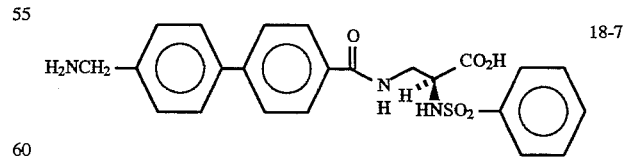

N-[3-(2(S)-Phenylsulphonylamino)propionate]-4'-aminomethyl-4-biphenylcarboxamide (18-7)

A solution of 18-6 (0.5 g, 1.02 mmol) in 6N HCl (5 mL) and dioxane (5 mL) was stirred at room temperature for 48 hours, concentrated, and chromatographed on silica gel eluting with 10:1:1 EtOH/$H_2O$/$NH_4OH$ to yield 18-7 as a white solid.

$^1$H NMR (400 MHz, D$_2$O+dTFA) δ 7.1 (m, 4H), 6.95 (d, 2H), 6.85 (d, 2H), 6.6 (s, 5H), 3.6 (m, 1H), 3.6 (s, 2H), 3.2 (dd, 1H), 2.8 (dd, 1H).

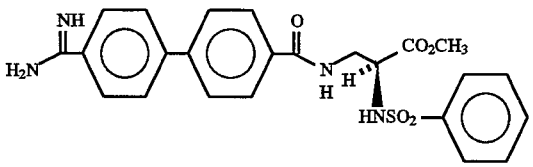

18-8

{Methyl N-[3-(2(S)-Phenylsulphonylamino)propionate]}-4'-amidino-4-biphenyl carboxamide A solution of 18-5 (0.2 g, 0.44 mmol) in 10 mL MeOH was cooled to −20° C. and saturated with HCl gas and stirred at room temperature for 16 hours. The reaction was concentrated, then dissolved in 10 mL MeOH and treated with NH$_4$CO$_3$ (0.25 g) for 16 hours. The solution was concentrated and the residue purified by flash chromatography eluting with 9:1:1 EtOH/H$_2$O/NH$_4$OH to give 18-8 as a white solid. R$_f$ 0.25 (9:1:1 EtOH/H$_2$O/NH$_4$OH).

$^1$H NMR (400 MHz, CD$_3$OD) δ 7.9 (m, 8H), 7.8 (m, 3H), 7.5 (m, 2H), 4.2 (m, 1H), 3.7 (dd, 1H), 3.55 (m, 1H), 3.5 (s, 3H).

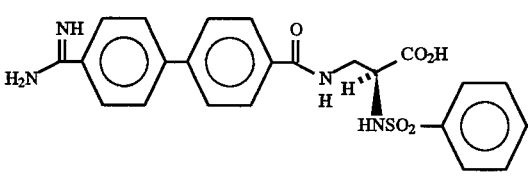

18-9

N-[3-(2(S)-Phenylsulphonylamino)propionate]-4'-amidino-4-biphenylcarboxamide (18-9)

A solution of 18-8 (0.2 g, 0.42 mmol) in 5 mL 6N HCl and 2 mL dioxane was stirred 48 hours at room temperature. An additional 4 mL of 6N HCl was added and after 26 hours the solution was concentrated to yield 18-9 as a white solid.

$^1$H NMR (400 MHz, DMSO) δ 9.5 (s, 2H), 9.3 (s, 2H), 8.7 (m, 1H), 8.3 (d, 1H), 8.0 (m, 4H), 7.9 (s, 4H), 8.8 (d, 2H), 7.3 (m, 3H), 4.0 (m, 1H), 3.5 (m, 1H), 3.3 (m, 1H).

SCHEME 19

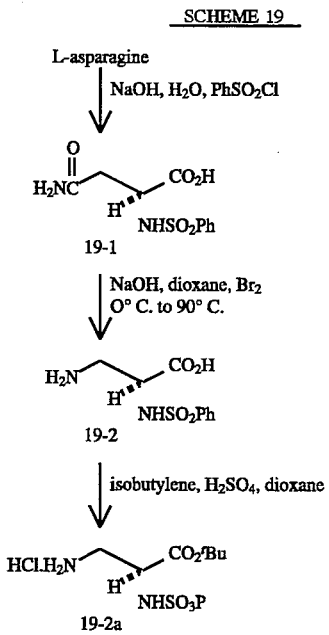

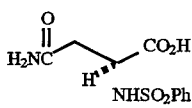

19-1

N-Phenylsulfonyl-L-asparagine (19-1)

To a stirred solution of L-asparagine (Aldrich) (10 g, 76 mmol), NaOH (3.4 g, 85 mmol), H$_2$O (50 mL), and dioxane (50 mL) at 0° C. was added PhSO$_2$Cl (10.6 mL, 84 mmol). After 1 min, NaOH (3.4 g) in H$_2$O (50 mL) was added and the reaction mixture stirred for 30 min. The reaction mixture was then concentrated to remove the dioxane then washed with EtOAc. The aqueous phase was then cooled to 0° C. and acidified to pH with conc. HCl to effect product precipitation. The resulting solid was collected by filtration, washed with H$_2$O (20 mL) and dried at 50° C. under vacuum to give 19-1 as a white solid. R$_f$ 0.40 (silica, 10:1:1 ethanol/H$_2$O/NH$_4$OH).

$^1$H NMR (300 MHz, D$_2$O) δ 7.59 (m, 2H), 7.26 (m, 3H), 3.92 (m, 1H), 3.02 (m, 1H), 2.35 (m, 1H).

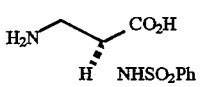

19-2

2(S)-Phenylsulfonylamino-3-aminopropionic acid (19-2)

To a stirred solution of NaOH (15.6 g, 0.4 mol) in H$_2$O (70 mL), cooled with an icebath, was added bromine (3.6 mL, 0.07 mol) dropwise. After 5 min, a cold solution of 19-1 (14.6 g, 54 mmol) and NaOH (4.3 g, 0.1 mol) in H$_2$O (50 mL) was added in one portion. The solution was stirred for 20 min at 0° C. then 30 min at 90° C. The reaction mixture was recooled to 0° C. and the pH adjusted to 7 through dropwise addition of conc. HCl. The white precipitate formed was collected by filtration and dried to give 19-2 as a white solid.

$^1$H NMR (300 MHz, D$_2$O) δ 8.00 7.50 (m, 5H), 3.88 (m, 1H), 3.37 (m, 1H), 3.12 (m, 1H).

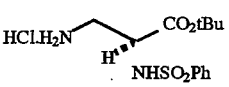

19-2a tert-Butyl 2(S)-phenylsulfonylamino-3-aminopropionate hydrochloride (19-2a)

In a Fischer-Porter tube, a mixture of 19-2 (10.2 g, 42 mmol) and DME (150 mL) was sequentially, treated with H$_2$SO$_4$ (6.4 mL, 0.12 mol), cooled to −78° C., and then condensed with isobutylene (75 mL). The cooling bath was removed. After 2 h, ice/water (250 mL) was added followed by washing with ether (2×). The aqueous phase was basified with aq 6N NaOH, saturated with NaCl, and extracted with EtOAc (3×). The combined extracts were washed with brine, dried (MgSO$_4$), and concentrated to give a white solid. This was dissolved in CHCl$_3$ then treated with 1N HCl/ether (22 mL) then concentrated to give 19-2a as a glossy yellow solid.

$^1$H NMR (400 MHz, DMSO) δ 8.25–8.00 (m, 4H), 7.85–7.58 (m, 5H), 4.08 (m, 1H), 3.10 (m, 1H), 2.73 (m, 1H), 1.17 (s, 9H).

SCHEME 19 (CONT'D)

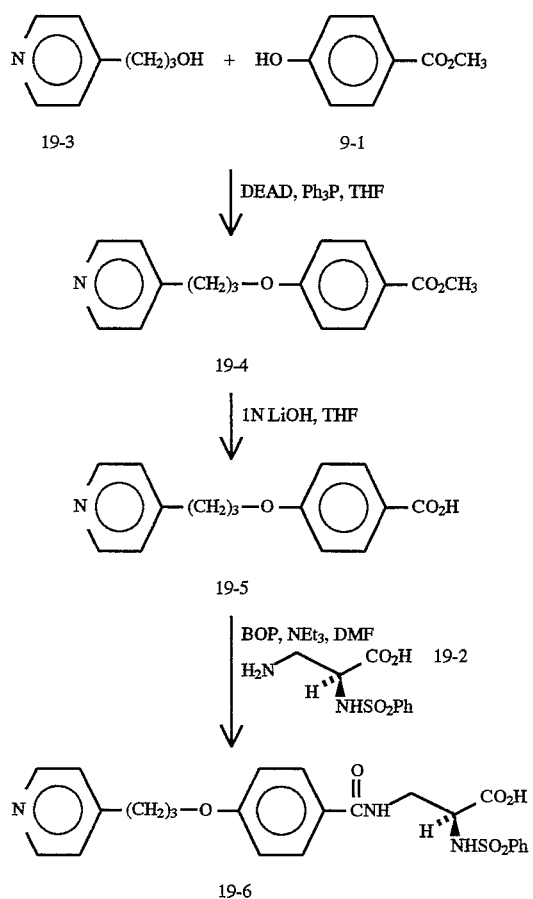

(0.22 mL, 1.5 mmol) and 19-2 (190 mg, 0.78 mmol) were added. After 20 h, the reaction mixture was concentrated and subjected to flash chromatography (silica, 10/1/1 $CH_2Cl_2$/$CH_3OH$/AcOH) to give impure 19-6 (400 mg). Prep HPLC purification (Delta Pak C-18Å column, 0 to 100% $CH_3CN$/$H_2O$ containing 0.1% trifluoroacetic acid) gave pure 19-6 as a whim solid after lyophilization. $R_f$ 0.74 (silica, 10/1/1 $CH_2Cl_2$/$CH_3OH$/AcOH).

$^1$H NMR (400 MHz, $D_2O$) δ 8.38 (m, 2H), 7.72 (m, 2H), 7.51 (m, 2H), 7.33 (m, 2H), 7.28 (m, 3H), 6.93 (m, 2H), 4.13 (t, J=6 Hz, 2H), 3.84 (dd, J=10 and 4 Hz, 1H), 3.64 (dd, J=14 and 4 Hz, 1H), 3.32 (dd, J=14 and 10 Hz, 1H), 2.88 (t, J=7 Hz, 2H), 2.18 (m, 2H).

SCHEME 20

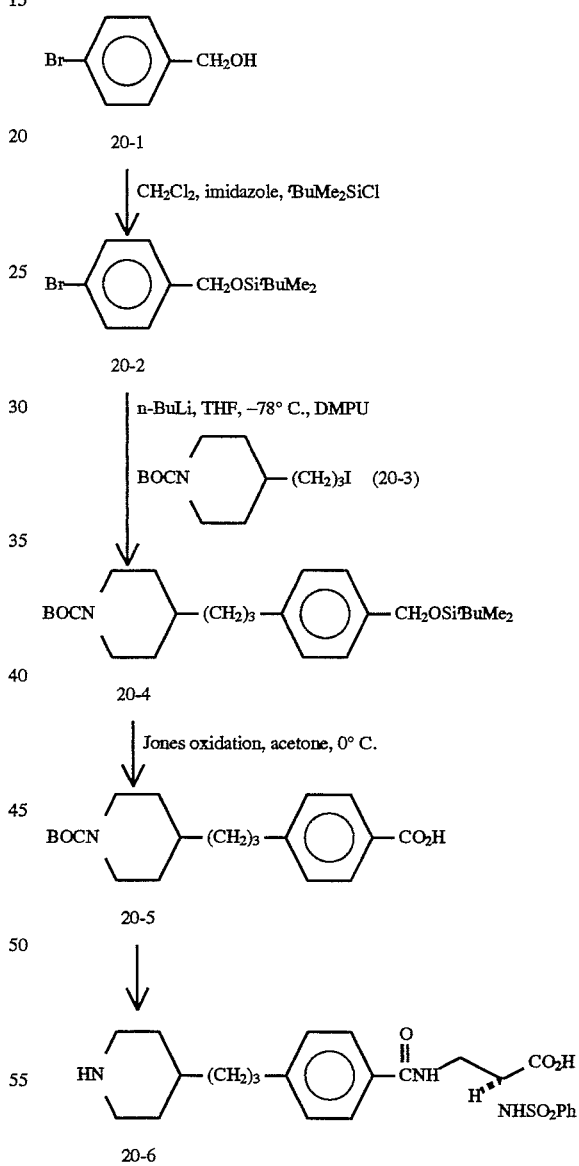

Methyl 4-[3-(Pyridin-4-yl)propyloxy]benzoate (19-4)

To a stirred solution of 9-1 (Aldrich) (2.0 g, 13.2 mmol), $PPh_3$ (4.3 g, 16.4 mmol), 19-3 (Aldrich) (2.0 g, 14.5 mmol), and THF (60 mL) at ambient temperature was added diethyl azodicarboxylate (DEAD) (2.9 g, 2.6 mL, 16.4 mmol) in THF (10 mL) dropwise over a 5 min period. After stirring overnight, the reaction mixture was diluted with EtOAc and then washed with $H_2O$, sat. $NaHCO_3$ and brine, dried ($MgSO_4$) and concentrated. Flash chromatography (silica, 50% EtOAc/hexanes) gave 19-4 as a colorless oil. $R_f$ 0.22 (silica, 50% EtOAc/hexanes).

$^1$H NMR (300 MHz, $CDCl_3$) δ 8.51 (m, 2H), 8.00 (m, 2H), 7.18 (m, 2H), 6.89 (m, 2H), 4.02 (t, J=7 Hz, 2H), 3.89 (s, 3H), 2.85 (t, J=7 Hz, 2H), 2.15 (m, 2H).

4-[3-(Pyridin-4-yl)propyloxy]benzoic acid (19-5)

A solution of 19-4 (3.2 g, 11.9 mmol), 1N LiOH (25 mL), and THF (50 mL) was stirred overnight at ambient temperature. After 20 h, the solution was washed with EtOAc and then acidified with 10% $KHSO_4$ to give a suspension of white solid. The aqueous portion was extracted with $CHCl_3$ and then the aqueous portion containing the solid was filtered. After drying the solid at 50° C. for 3 h, 19-5 was obtained. $R_f$ 0.47 (silica, 10/1/1 $CH_2Cl_2$/$CH_3OH$/AcOH).

$^1$H NMR (300 MHz, $D_2O$+$K_2CO_3$) δ 8.00 (m, 2H), 7.69 (m, 2H), 6.68 (m, 2H) 6.53 (m, 2H), 3.50 (m, 2H), 2.23 (m, 2H), 1.55 (m, 2H).

4-[3-(Pyridin-4-yl)propyloxy]benzoyl-2(S)-phenylsulfonylamino-β-alanine (19-6)

A solution of 19-5 (200 mg, 0.78 mmol), $NEt_3$ (0.22 mL, 1.5 mmol), and DMF (4 mL) at ambient temperature was treated with BOP (345 mg, 0.78 mmol). After 3.0 h, $NEt_3$

4-Bromobenzyl alcohol t-butyldimethylsilyl ether (20-2)

A stirred solution of 20-1 (Aldrich; 3.0 g, 16.0 mmol) in $CH_2Cl_2$ (80 mL) at ambient temperature was treated sequentially with imidazole (1.2 g, 17.6 mmol) and tert-butyldimethylsilyl chloride (2.7 g, 17.6 mmol). After 1.5 h the reaction mixture was washed with $H_2O$ and brine, dried ($MgSO_4$) and concentrated to give 20-2 as a yellow oil. $R_f$ 0.70 (silica, 10% EtOAc/hexanes).

¹H NMR (300 MHz, CDCl₃) δ 7.34 (d, J=8 Hz, 2H), 7.09 (d, J=8 Hz, 2H), 4.07 (s, 2H), 0.85 (s, 9H), 0.99 (s, 6H).

4-[3-(N-Boc-Piperidin-4-yl)propyl]benzyl alcohol t-butyldimethylsilyl ether (20-4)

A stirred solution of 20-2 (401 mg, 1.33 mmol) in THF (13 mL) at −78° C. was treated with n-BuLi (0.9 mL, 1.46 mmol; 1.6 M/hexanes). After 5 min., 1,3-dimethyl-3,4,5,6-tetrahydro-2(1H)-pyrimidinone (DMPU) (0.32 mL, 2.7 mmol) was added followed by addition of 20-3 (47 1 mg, 1.33 mmol; see European Publication 478,328 for preparation) in THF (1 mL) after 5 min. The cooling bath was removed after 15 min and the reaction was stirred overnight. After 16 hours, the reaction was diluted with EtOAc and then washed with H₂O and brine, dried (MgSO₄), and concentrated. Flash chromatography (silica, 5% EtOAc/hexanes) gave 20-4 as a yellow oil. R$_f$ 0.81 (silica, 10% EtOA/hexanes).

¹H NMR (400 MHz, CDCl₃) δ 7.14 (d, J=8 Hz, 2H), 7.03 (d, J=8 Hz, 2H), 4.62 (s, 2H), 3.96 (m, 2H), 2.56 (m, 2H), 2.48 (t, J=7 Hz, 2H), 1.60–0.90 (m, 9H), 1.36 (s, 9H), 0.85 (s, 9H), 0.00 (s, 6H).

4-[3-(N-BOC-Piperidin-4-yl)propyl]benzoic acid (20-5)

To a vigorously stirred solution of 20-4 (230 mg, 0.51 mmol) in acetone (5 mL) at 0° C. was added Jones Reagent dropwise until the color changed from green to orange. The excess Jones Reagent was quenched with isopropanol (1 mL) followed by stirring for 15 min. The reaction mixture was diluted with EtOAc and then washed with H₂O and brine, dried (MgSO₄) and concentrated to give 20-5 as a yellowish oil.

¹H NMR (400 MHz, CDCl₃) δ 8.01 (d, J=8 Hz, 2H), 7.25 (d, J=8 Hz, 2H), 4.02 (m, 2H), 2.63 (m, 2H), 1.70–1.00 (m, 9H), 1.42 (s, 9H).

4-[3-(Piperidin-4-yl)propyl]benzoyl-2(S)-phenyl-sulfonylamino-β-alanine (20-6)

20-5 was treated with 9-12 as described for 18-5 to afford the desired ester which was hydrolyzed as described for 18-7 to provide 20-6. R$_f$ 0.4 (silica, ethanol/H₂O/NH₄OH 10:1:1).

¹H NMR (400 MHz, D₂O) δ 7.59 (m, 2H), 7.32 (d, 2H), 7.17 (m, 5H), 4.08 (m, 1H), 3.62 (dd, 1H), 3.30 (dd, 1H), 3.20 (m, 2H), 2.77 (m, 2H), 2.52 (t, 2H), 1.80–1.10 (m, 9H).

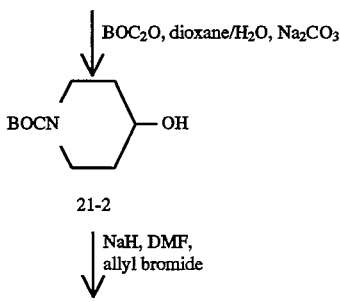

SCHEME 21

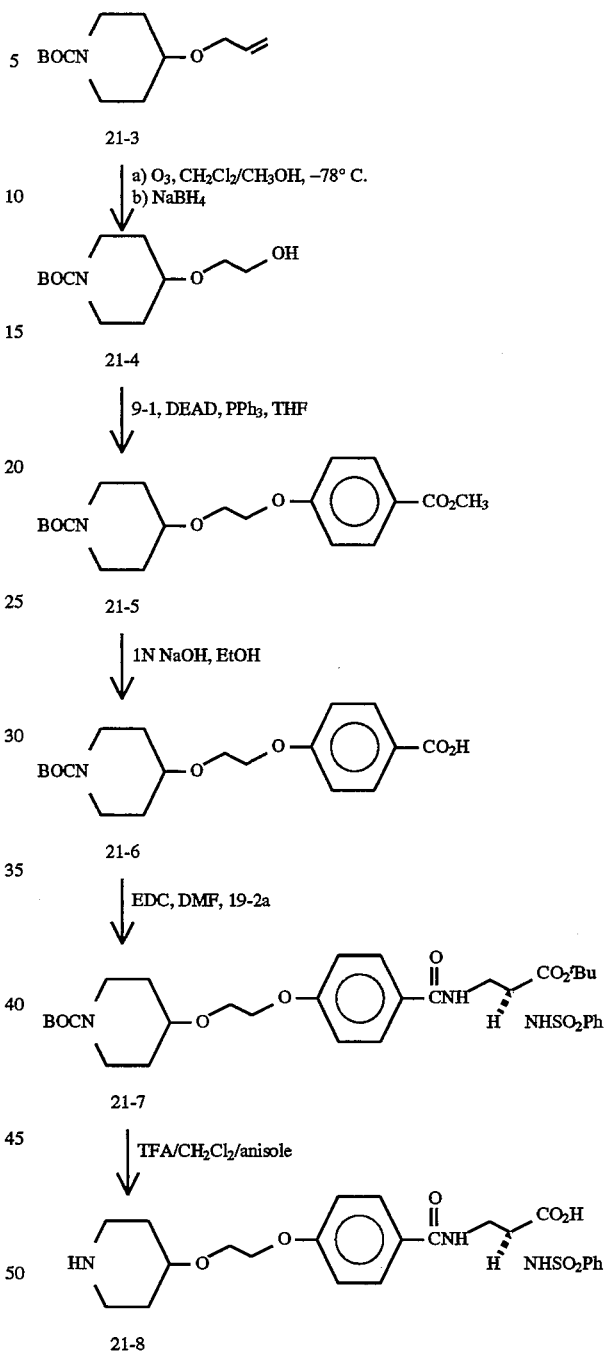

N-Boc-4-Hydroxypiperidine (21-2)

A stirred solution of 21-1 (9.4 g, 93 mmol), dioxane (100 mL), and 8% Na₂CO₃ (100 mL) at ambient temp. was treated with BOC₂O (23 g, 0.11 mmol). The reaction was continued for 30 min. while maintaining the pH at 8–10 with addition of Na₂CO₃. The dioxane was then evaporated and the residue diluted with H₂O and extracted with EtOAc (2×). The combined extracts were washed with brine, dried (MgSO₄), and concentrated to give 21-2 as an off-white solid. R$_f$ 0.25 (silica, 50% EtOAc/hexanes).

¹H NMR (400 MHz, CDCl₃) δ 3.85 (m, 3H), 3.01 (m, 2H), 1.85 (m, 2H), 1.46 (m, 2H), 1.44 (s, 9H).

3-[(N-Boc-Piperidin-4-yl)oxy]propene (21-3)

To a suspension of NaH (0.48 g, 11.9 mmol; 60% dispersion) in dry DMF (50 mL) at 0° C. was added a solution of 21-2 (2.0 g, 9.9 mmol) in DMF (15 mL). After 10 min, the cooling bath was removed, but then returned after another 10 min, followed by addition of allyl bromide (4.3 mL, 50 mmol). After 1.5 h, the reaction was quenched with 10% $KHSO_4$ and then diluted with $H_2O$ (90 mL). The reaction mixture was extracted with EtOAc, the layers separated, and the EtOAc portion washed with $H_2O$, 5% $KHSO_4$, sat. $NaHCO_3$ and brine, dried ($MgSO_4$) and concentrated. Flash chromatography (silica, 20% EtOAc/hexanes) gave 21-3 as a yellowish oil. $R_f$ 0.47 (silica, 20% EtOAc/hexanes).

$^1$H NMR (400 MHz, $CDCl_3$) δ 5.92 (m, 1H), 5.28 (m, 1H), 5.17 (m, 1H), 4.02 (m, 2H), 3.79 (m, 2H), 3.50 (m, 1H), 3.08 (m, 2H), 1.82 (m, 2H), 1.51 (m, 2H), 1.45 (s, 9H).

2-[(N-Boc-Piperidin-4-yl)oxy]ethanol (21-4)

Ozone was bubbled into a solution of 21-3 (1.5 g, 6.4 mmol) in 2:1 $CH_3OH/CH_2Cl_2$ (102 mL) at −78° C. After 5 min no starting material remained so oxygen was bubbled through the solution for 15 min to remove excess ozone. $NaBH_4$ (1.7 g, 45 mmol) was added and the cooling bath removed. After 1 h the reaction mixture was concentrated. The residue was diluted with $H_2O$ (30 mL) and then extracted with $CHCl_3$ (300 mL). The organic phase was washed with brine (30 mL), dried ($MgSO_4$), and concentrated. Flash chromatography (silica, EtOAc) gave 21-4 as a nearly colorless oil. $R_f$ 0.42 (silica, EtOAc).

$^1$H NMR (400 MHz, $CDCl_3$) δ 3.75 (m, 4H), 3.59 (m, 2H), 3.50 (m, 1H), 3.08 (m, 2H), 1.84 (m, 2H), 1.53 (m, 2H), 1.46 (s, 9H).

Methyl 4-[2-(N-Boc-Piperidin-4-yloxy)ethyloxy]benzoate (21-5)

A stirring solution of 9-1 (0.80 g, 5.2 mmol), $PPh_3$ (1.7 g, 6.5 mmol), and THF (20 mL) at ambient temperature was treated dropwise with a solution of 21-4 (1.3 g, 5.2 mmol), DEAD (1.0 mL, 6.5 mmol) and THF (20 mL). After addition was complete the reaction mixture was stirred for 20 hours at ambient temperature. The reaction mixture was then diluted with EtOAc and washed with $H_2O$, sat. $NaHCO_3$, 5% $KHSO_4$ and brine. Drying ($MgSO_4$), concentration, and then flash chromatography (silica, 30% EtOAc/hexanes) gave 21-5 as a colorless oil. TLC $R_f$=0.29 (silica, 30% EtOAc/hexanes);

$^1$H NMR (300 MHz, $CDCl_3$) δ 7.99 (d, J=11 Hz, 2H), 6.93 (d, J=11 Hz, 4.17 (m, 2H), 3.88 (s, 3H), 3.82 (m, 2H), 3.78 (m, 2H), 3.56 (m, 1H), 3.10 (m, 2H), 1.85 (m, 2H), 1.55 (m, 2H), 1.46 (s, 9H).

4-[2-(N-Boc-Piperidin-4-yloxy)ethyloxy]benzoic acid (21-6)

A solution of 21-5 (1.6 g, 4.1 mmol), ethanol (41 mL), and 1N NaOH (21 mL) was stirred at ambient temperature for 20 hours. The reaction was then concentrated and the residue dissolved in $H_2O$ and then washed with ether. The aqueous phase was acidified with 5% $KHSO_4$ and then extracted with EtOAc. The EtOAc portion was washed with 5% $KHSO_4$ and brine, dried ($MgSO_4$), and concentrated to furnish 21-6 as a white solid. TLC $R_f$=0.68 (silica, acetone);

$^1$H NMR (300 MHz, $CDCl_3$) δ 8.05 (d, J=11 Hz, 2H), 6.95 (d, J=11 Hz, 2H), 4.18 (m, 2H), 3.85 (m, 2H), 3.78 (m, 2H), 3.57 (m, 1H), 3.12 (m, 2H), 1.85 (m, 2H), 1.55 (m, 4H), 1.46 (s, 9H).

4-[2-(N-Boc-Piperidin-4-yloxy)ethyloxy]benzoyl-2(S)-phenyl-sulfonylamino-β-alanine tert-butyl ester (21-7)

A stirring solution of 21-6 (100 mg, 0.27 mmol), DMF (1.5 mL), NMM (105 gL, 0.96 mmol), 19-2a (86 mg, 0.29 mmol), and HOBT (48 mg, 0.36 mmol) at 0° C. was treated with EDC (68 mg, 0.36 mmol) followed by removal of the cooling bath. After 20 h the reaction mixture was diluted with EtOAc and then washed with $H_2O$, 5% $KHSO_4$, sat. $NaHCO_3$ and brine, dried ($MgSO_4$), and concentrated. Flash chromatography (silica, 65% EtOAc/hexanes) gave 21-7 as an oil. TLF $R_f$=0.38 (silica, 65% EtOAc/hexanes);

$^1$H NMR (300 MHz, $CDCl_3$) δ 7.86 (m, 2H), 7.76 (d, J=11 Hz, 2H), 7.52 (m, 3H), 6.93 (d, J=11 Hz, 2H), 6.63 (m, 1H), 5.68 (d, J=8 Hz, H), 4.15 (m, 2H), 3.95–3.70 (m, 6H), 3.55 (m, 2H), 3.10 (m, 2H), 1.85 (m, 2H), 1.57 (m, 2H), 1.45 (S, 9H), 1.28 (S, 9H).

4-[2-(Piperidin-4-yloxy)ethyloxy]benzoyl-2(S)-phenylsulfonylamino-β-alanine (21-8)

A solution of 21-7 (168 mg, 0.26 mmol), anisole (56 mg, 0.52 mg), $CH_2Cl_2$ (1.3 mL), and TFA (1.3 mL) was stirred at ambient temperature for 15 min. Concentration and then flash chromatography (silica, 10:0:0.8 ethanol/$NH_4OH$/$H_2O$) gave 21-8 as a white solid. TLC $R_f$=0.32 (silica, 10:0.8:0.8 ethanol/$NH_4OH$/$H_2O$); $R_f$ 0.46 (silica, 0/0.8/0.8 ethanol/$NH_4OH$/$H_2O$)

$^1$H NMR (400 MHz, $D_2O$) δ 7.77 (m, 2H), 7.57 (m, 2H), 7.39 (m, 3H), 7.04 (m, 2H), 4.30 (m, 2H), 4.25 (m, 1H), 3.95 (m, 2H), 3.86 (m, 1H), 3.79 (dd, J=14 and 4 Hz, 1H), 3.48 (dd, J=16 and 10 Hz) 1H, 3.38 (m, 2H), 3.13 (m, 2H), 2.14 (m, 2H), 1.86 (m, 2H).

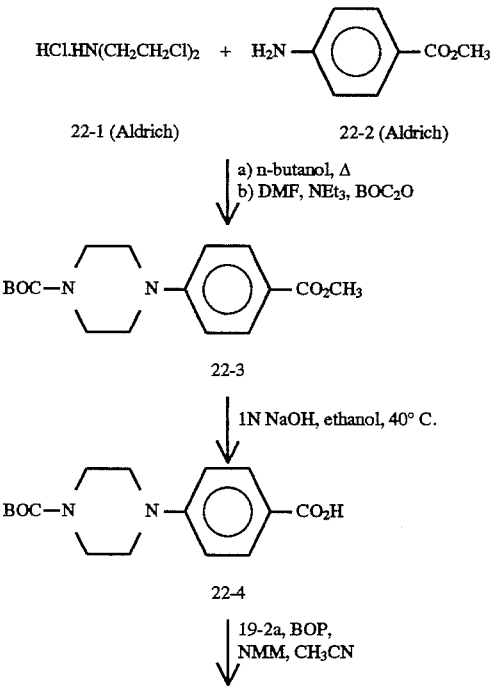

SCHEME 22

SCHEME 22 (continued)

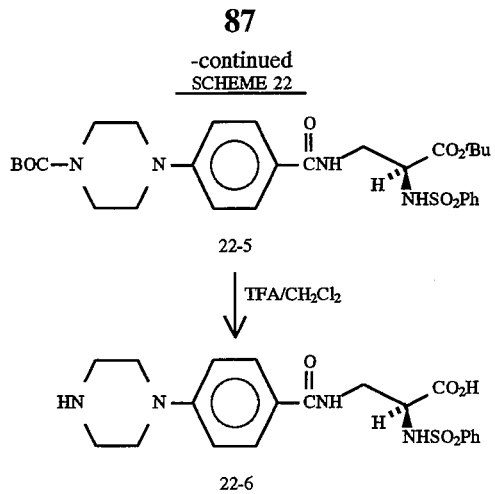

Methyl 4-(N-Boc-N'-piperazinyl)benzoate (22-3)

A mixture of 22-1 (2.4 g, 13.2 mmol), 22-2 (2.0 g, 13.2 mmol), and n-butanol (6.5 mL) was refluxed for 5 days. The cooled reaction mixture was then filtered to give the crude phenylpiperazine as a white solid. The crude solid was dissolved in DMF and treated with diisopropylethylamine (2.1 mL, 40 mmol) and Boc$_2$O (1.6 g, 20 mmol). After 1.0 h the reaction mixture was diluted with EtOAc and then washed with H$_2$O, sat. NaHCO$_3$, 10% KHSO$_4$ and brine, dried (MgSO$_4$), and concentrated. Flash chromatography (silica, 10% EtOAc/hexanes) gave 22-3 as a white solid. TLC R$_f$=0.34 (silica, 20% EtOAc/hexanes);

$^1$H NMR (300 MHz, CD$_3$OD) 7.90 (d, J=11 Hz, 2H), 6.96 (d, J=11 Hz, 2H), 3.87 (s, 9H), 3.60 (m, 4H), 3.33 (m, 4H), 1.50 (s, 9H).

4-(N-Boc-N'-piperazinyl)benzoic acid (22-4)

A mixture of 22-3 (700 mg, 2.2 mmol), 1N NaOH, and ethanol (10 mL) was heated at 40° C. for 4 hours. The cooled reaction mixture was acidified with 10% KHSO$_4$ and then extracted with EtOAc. The organic portion was washed with brine, dried (MgSO$_4$) and concentrated to give 22-4 as a white solid. TLC R$_f$=0.80 (silica, 10:0.5:0.5 CH$_2$Cl$_2$/CH$_3$OH/AcOH);

$^1$H NMR (400 MHz, CD$_3$OD) δ 7.92 (d, J=11 Hz, 2H), 7.01 (d, J=11 Hz, 2H), 3.62 (m, 4H), 3.34 (m, 4H), 1.52 (s, 9H).

4-(N-Boc-N'-Piperazinyl)benzoyl-2(S)-phenylsulfonylamino-β-alanine tert-butyl ester (22-5)

A mixture of 22-4 (300 mg, 1.0 mmol), 19-2a (329 mg, 1.0 mmol), NMM (430 gL, 4.0 mmol), and CH$_3$CN (5 mL) at ambient temperature was treated with BOP (650 mg, 1.5 mmol). After 20 h the reaction mixture was diluted with EtOAc and then washed with 10% KHSO$_4$ and brine, dried (MgSO$_4$) and concentrated. Flash chromatography (silica, 40% EtOAc/hexanes) gave 22-5 as a white solid. TLC R$_f$=0.16 (silica, 40% EtOAc/hexanes);

$^1$H NMR (300 MHz, CD$_3$OD) δ 7.75 (m, 2H), 7.60 (d, J=11 Hz, 2H), 7.40 (m, 3H), 6.88 (d, J=11 Hz, 2H), 4.03 (m, 1H), 3.50 (m, 4H), 3.30 (m, 6H), 1.44 (s, 9H), 1.16 (s, 9H).

4-(N-Piperazinyl)benzoyl-2(S)-phenylsulfonylamino-β-alanine (22-6)

A solution of 22-5 (300 mg, 0.51 mmol), TFA (4 mL), and CH$_2$Cl$_2$ (4 mL) was stirred at ambient temperature for 3.0 hours. The solution was then concentrated followed by azeotropic removal of residual TFA with toluene. The residue was triturated with (10:1:1 ethanol/NH$_4$OH/H$_2$O), filtered, and dried in vacuo to give 22-5 as a white solid. TLC R$_f$=0.37 (silica, ethanol/NH$_4$OH/H$_2$O 10:1:1).

$^1$H NMR (400 MHz, CD$_3$OD) δ 7.85 (m, 2H), 7.77 (d, J=11 Hz, 2H), 7.50 (m, 3H), 7.20 (d, J=11 Hz, 2H), 4.26 (m, 1H), 3.80–3.45 (m, 10H).

SCHEME 23

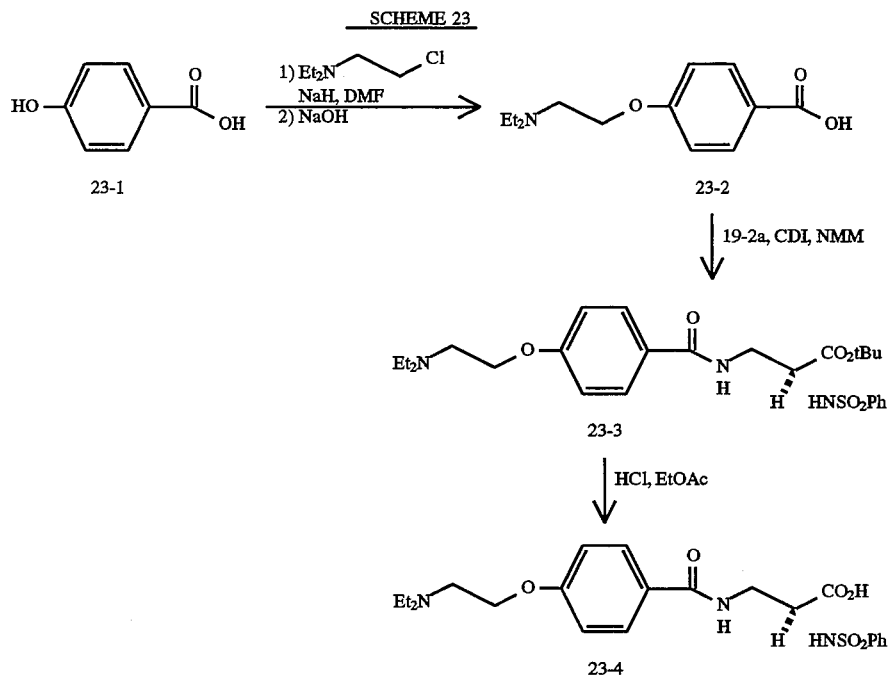

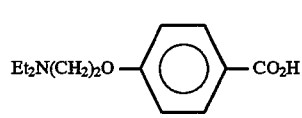

4-[2-(N,N-Diethylamino)ethyloxy]benzoic acid (23-2)

A solution of 4-hydroxybenzoic acid (Aldrich) (10 g, 72 mmol) in DMF (100 mL) was treated with NaH (50% dispersion in oil, 10.4 g, 216 mmol) and N,N-diethylchloroethylamine·HCl (Aldrich) (12.5 g, 72 mmol) at room temperature for 24 h. The solution was concentrated, the residue was dissolved in water, acidified to pH2, and extracted with 4× 100 mL EtOAc. The organic layers were concentrated to give the bis-alkylated product as a white solid which was dissolved in water (30 mL) and dioxane (50 mL) and treated with 5.4 g NaOH. After 24 h the solution was concentrated and the residue was chromatographed (40:1:1 EtOH/H$_2$O/NH$_4$OH) to give 23-2 as a white solid. R$_f$ (40:1:1 EtOH/H$_2$O/NH$_4$OH) 0.24

$^1$H NMR (300 MHz, D$_2$O) δ 7.9 (d, 2H), 7.0 (d, 2H), 4.35 (m, 2H), 3.50 (m, 2H), 3.22 (m, 4H), 1.35 (m, 6H).

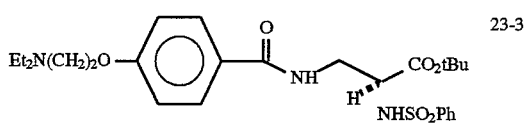

4-[2-(N,N-Diethylamino)ethloxy]benzoyl-2(S)-phenylsulfonylamino-β-alanine t-butyl ester (23-3)

A solution of 23-2 (0.6 g, 2.5 mmol) in DMF (10 mL) was treated with carbonyldiimidazole (0.49 g, 3 mmol) for 30 minutes, followed by 9-12 (0.85 g, 2.5 mmol) and N-methylmorpholine (0.84 mL, 7.6 mmol). The solution was stirred at room temperature for 24 h, then concentrated, adsorbed to silica and chromatographed (80% acetone/hexanes) to give 23-3 as a white solid. R$_f$ (80% acetone/hexanes) 0.37

$^1$H NMR (300 MHz, CDCl$_3$) δ 7.82 (d, 2H), 7.7 (m, 4H), 7.5 (d, 1H), 7.41 (d, 2H), 6.8 (d, 2H), 4.08 (m, 3H), 3.78 (m, 2H), 2.9 (t, 2H), 2.65 (q, 4H), 1.25 (s, 9H), 1.4 (t, 6H).

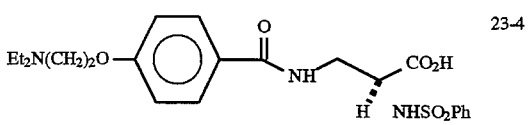

4-[2-(N,N-Diethylamino)ethyloxy]benzoyl-2(S)-phenylsulfonylamino-β-alanine (23-4)

A solution of 23-3 in EtOAc (10 mL) was cooled to −78° C., saturated with HCl gas and warmed to 0° C. for 1 h. The solution was concentrated and the residue was purified by preparative HPLC to give 23-4 as a white solid (TFA salt).

$^1$H NMR (300 MHz, D$_2$O) δ 7.72 (d, 2H), 7.55 (d, 2H), 7.35 (m, 3H), 7.0 (d, 2H), 4.20 (bs, 2H), 4.16 (dd, 1H), 3.72 (dd, 1H), 3.6 (bs, 2H), 3.4 (dd, 1H), 3.14 (m, 4H), 1.3 (m, 6H).

SCHEME 24

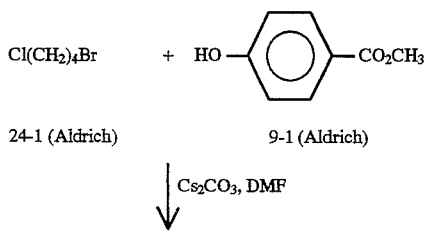

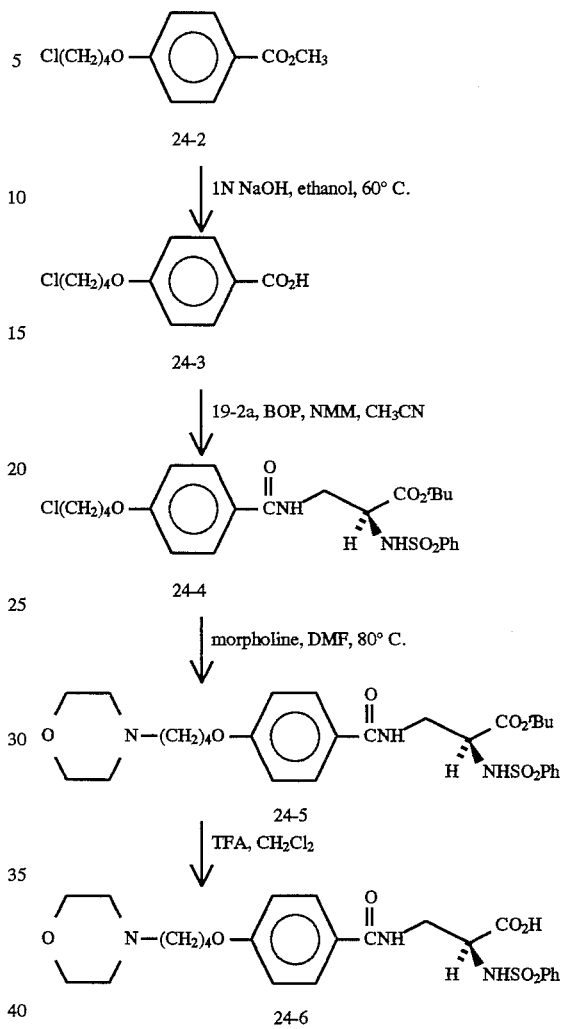

Methyl 4-(4-Chlorobutyloxy)benzoate (24-2)

A stirring solution of 9-1 (2.0 g, 13.1 mmol), 24-1 (4.5 g, 26.2 mmol) and DMF at ambient temperature was treated with Cs$_2$CO$_3$ (6.4 g, 20 mmol). After 1.0 hour the reaction mixture was diluted with EtOAc and then washed with H$_2$O, 10% KHSO$_4$ and brine, dried (MgSO$_4$), and concentrated. Flash chromatography (silica, 10% EtOAc/hexanes) gave 24-2 as a colorless oil. TLC R$_f$=0.58 (silica, 20% EtOAc/hexanes);

$^1$H NMR (300 MHz, CDCl$_3$) δ 7.99 (d, J=11 Hz, 2H), 6.90 (d, J=11 Hz, 2H), 4.06 (m, 2H), 3.89 (s, 3H), 3.62 (m, 2H), 1.98 (m, 2H).

4-(4-Chlorobutyloxy)benzoic acid (24-3)

A mixture of 24-2 (3.0 g, 12.4 mmol), 1N NaOH (30 mL), and ethanol was heated at 60° C. for 1.0 hour. The cooled reaction mixture was acidified with 10% KHSO$_4$ and then extracted with EtOAc. The EtOAc portion was washed with brine, dried (MgSO$_4$) and concentrated to give 24-3 as a white solid.

$^1$H NMR (300 MHz, CD$_3$OD) δ 7.98 (d, J=11 Hz, 2H), 6.98 (d, J=Hz, 2H), 4.07 (m, 2H), 3.63 (m, 2H), 1.94 (m, 4H).

4-(4-Chlorobutyloxy)benzoyl-2(S)-phenylsulfonylamino-β-alanine tert-butylester (24-4)

A stirring solution of 24-3 (250 mg, 1.1 mmol), 19-2a (368 mg, 1.1 mmol), NMM (442 mg, 4.4 mmol), and CH$_3$CN (5 mL) at ambient temperature was treated with BOP (483 mg, 1.1 mmol). After 20 h the reaction mixture was diluted with EtOAc and then washed with H$_2$O, sat. NaHCO$_3$, 10% KHSO$_4$ and brine, dried (MgSO$_4$) and concentrated. Flash chromatography (silica, 40% EtOAc/ hexanes) gave 24-4 as a white solid. TLC R$_f$=0.46 (silica, 50% EtOAc/hexanes);

$^1$H NMR (300 MHz, 10% CD$_3$OD/CDCl$_3$) δ 7.85 (m, 2H), 7.76 (d, J=11 Hz, 2H), 7.52 (m, 3H), 6.92 (d, J=11 Hz, 2H), 4.06 (m, 2H), 3.99 (m, 1H), 3.82–3.60 (m, 4H), 1.99 (m, 4H), 1.26 (s, 9H).

4-[4(N-Morpholino)butyloxy)benzoyl]-2(S)-phenylsulfonylamino-β-alanine tert-butyl ester (24-5)

A stirring solution of 24-4 (500 mg, 1.0 mmol), morpholine (437 gL, 5.0 mmol), and DMF (5 mL) was heated at 80° C. for 20 hours. The cooled reaction mixture was diluted with EtOAc and then washed with H$_2$O and brine, dried (MgSO$_4$) and concentrated. Flash chromatography (silica, EtOAc) gave 24-5 as a yellow solid. TLC R$_f$ 0.14 (silica, EtOAc);

$^1$H NMR (300 MHz, CD$_3$OD) δ 7.83 (m, 2H), 7.74 (d, J=11 Hz, 2H), 7.50 (m, 3H), 6.96 (d, J=11 Hz, 2H), 4.10 (m, 3H), 3.73–3.40 (m, 8H), 2.45 (m, 4H), 1.90–1.65 (m, 4H), 1.26 (s, 9H).

4-[4-(N-Morpholino)butyloxy]benzoyl-2(S)-phenylsulfonylamino-β-alanine (24-6)

A solution of 24-5 (430 mg, 0.76 mmol), TFA (5 mL), and CH$_2$Cl$_2$ (5 mL) was stirred at ambient temperature for 3.0 hours. Concentration of the reaction mixture followed by azeotropic removal of residual TFA with toluene gave crude 24-6. Flash chromatography (silica, 10:0.1:0.1 ethanol/H$_2$O/ NH$_4$OH) gave 24-6 as a white solid. TLC R$_f$=0.52 (silica, 10:0.1:0.1 ethanol/NH$_4$OH/H$_2$O);

$^1$H NMR (400 MHz, D$_2$O) δ 7.68 (d, J=10 Hz, 2H), 7.48 (d, J=11 Hz, H), 7.30 (m, 3H), 6.96 (d, J=11 Hz, 2H), 4.08 (m, 3H), 4.00–3.00 (m, H), 1.80 (m, 4H).

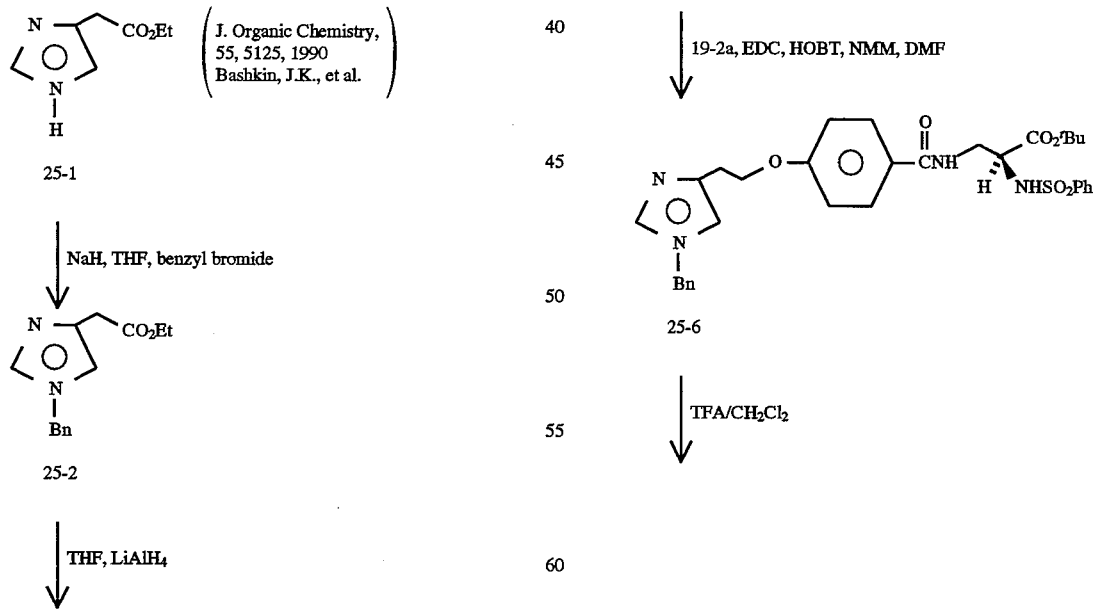

-continued
SCHEME 25

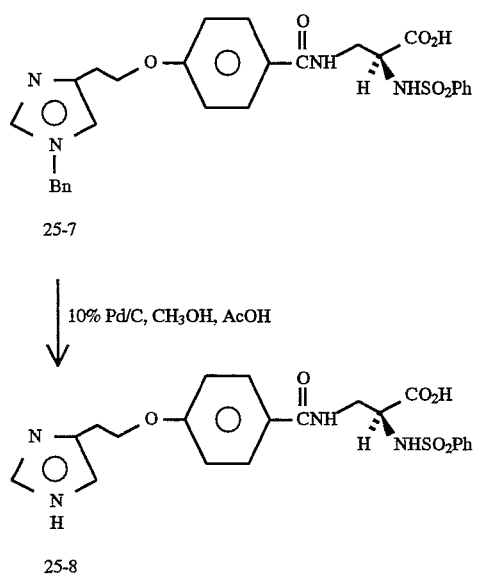

Ethyl (N-Benzylimidazol-4-yl)acetate (25-2)

To a magnetically stirred suspension of NaH (1.1 g, 26 mmol) in THF (25° C.) at 0° C. was added 25-1 (3.8 g, 24.6 mmol) in THF (15 mL) dropwise over 30 min., followed by removal of the cooling bath. After 3 hours benzyl bromide (2.8 mL, 23.4 mmol) added. After 20 hours the mixture was diluted with $CH_2Cl_2$ and then washed with $H_2O$, dried ($MgSO_4$) and concentrated. Flash chromatography (silica, ($CHCl_3/NH_3$)/EtOAc) gave 25-2 as a pale yellow liquid. TLC $R_f$=0.15 (silica, 40% ($CHCl_3/NH_3$)/EtOAc);

$^1$H NMR (300 MHz, $CDCl_3$) δ 7.47 (s, 1H), 7.40–7.15 (m, 5H), 6.87 (S, 1H), 5.07 (s, 2H), 4.26 (q, J=7 Hz, 2H), 3.63 (s, 2H), 1.26 (t, J=7 Hz, 3H).

(N-Benzylimidazol-4-yl)ethanol (25-3)

A solution of 25-2 (4.6 g, 18.8 mmol) in THF (50 mL) at ambient temperature was treated dropwise with $LiAlH_4$ (9.4 mL, 9.4 mmol, 1M in THF). After stirring for 1 hour the reaction was quenched with a saturated sodium potassium tartrate solution. The mixture was then poured into EtOAc and washed with $H_2O$ and brine, dried ($MgSO_4$) and concentrated to yield 25-3 as a yellow oil.

$^1$H NMR (300 MHz, $CDCl_3$) δ 7.45 (s, 1H), 7.40–7.10 (m, 5H), 6.68 (s, 1H), 5.03 (s, 2H), 3.88 (t, J=6 Hz, 2H), 2.78 (t, J=6 Hz, 2H).

Methyl 4-(2-(N-Benzylimidazol-4-yl)ethyloxy]benzoate (25-4)

A stirring solution of 9-1 (152 mg, 1.0 mmol), $PPh_3$ (341 mg, 1.3 mmol), and THF (20 mL) at ambient temperature was treated dropwise with DIAD (256 gL, 1.3 mmol), 25-3 (202 mg, 1.0 mmol), and THF (10 mL) over 30 min followed by heating at 70° C. for 24 hours. The cooled reaction mixture was concentrated and then chromatographed (silica, 40% ($CHCl_3/NH_3$)/EtOAc) to give 25-4 as a Colorless gum. TLC $R_f$=0.16 (silica, 40% ($CHCl_3/$ $NH_3$/EtOAc);

$^1$H NMR (300 MHz, $CDCl_3$) δ 7.96 (d, J=11 Hz, 2H, 7.48 (s, 1H), 7.40–7.10 (m, 5H), 6.90 (d, J=11 Hz, 2H), 6.74 (s, 1H), 5.05 (s, 2H), 4.28 (t, J=7 Hz, 2H), 3.85 (s, 3H), 3.06 (t, J=7 Hz, 2H).

4-[2-(N-Benzylimidazol-4-yl)ethyloxy]benzoic acid (25-5)

A mixture of the ester 25-4 (170 mg, 0.51 mmol), $CH_3OH$ (10 mL), and 1N NaOH (5 mL) was stirred for 20 hours at ambient temperature. The cooled reaction mixture was acidified with 1N HCl (5 mL) and extracted with EtOAc.

The EtOAc portion was concentrated to give 25-5 as a gelataneous solid.

$^1$H NMR (300 MHz, $CD_3OD$) δ 7.90 (d, J=11 Hz, 2H), 7.67 (s, 1H), 7.40–7.20 (m, 5H), 6.95 (s, 1H), 6.88 (d, J=11 Hz, 2h), 4.23 (t, J=6 Hz, 2H), 2.98 (t, J=6 Hz, 2H).

4-[2-(N-Benzylimidazol-4-yl)ethyloxy]benzoyl-2(S)-phenylsulfonyl-amino-β-alanine tert-butyl ester (25-6)

A stirring solution of 25-5 (147 mg, 0.46 mmol), 19-2a (154 mg, 0.46 mmol), HOBT (94 mg, 0.62 mmol), NMM (100 gL, 0.91 mmol), and DMF (120 mL) at 0° C. was treated with EDC (118 mg, 0.62 mmol) and the cooling bath removed. After 24 hours the reaction mixture was concentrated. Flash chromatgraphy (silica, $CH_2Cl_2$, $CH_3OH$/AcOH 9:0.5:0.5) gave 25-6 as a pale yellow solid. TLC $R_f$=0.35 (silica, 8:1:1 $CH_2Cl_2/CH_3OH$/AcOH);

$^1$H NMR (300 MHz, $CDCl_3$) δ 7.87 (m, 2H), 7.73 (d, J=11 Hz, 2H), 7.60–7.10 (m, 6H), 6.92 (d, J=11 Hz, 2H), 6.75 (s, 1H), 6.59 (m, 1H), 5.67 (m, 1H), 5.07 (s, 2H), 4.27 (t, J=6 Hz, 2H), 3.90 (m, 2H), 3.56 (m, 1H), 3.05 (t, J=6 Hz, 2H), 1.28 (s, 9H).

4-[2-(N-Benzylimidazol-4-yl)ethyloxy]benzoyl-2(S)-phenylsulfonyl-amino-β-alanine (25-7)

Utilizing the procedure for converting 24-5 to 24-6, 25-6 (252 mg, 0.42 mmol) gave 25-7 as a colorless solid after chromatography (silica, ethanol/$NH_4OH$/$H_2O$, 9:0.5:0.5).

$^1$H NMR (300 MHz, $CD_3OD$) δ 7.99 (s, 1H), 7.84 (m, 2H), 7.73 (d, J=11 Hz, 2H), 7.55–7.25 (m, 8H), 7.08 (s, 1H), 6.93 (d, J=11 Hz, 2H), 5.22 (s, 2H), 4.23 (t, J=6 Hz, 2H), 3.90–3.50 (m, 3H), 3.04 (t, J=6 Hz, 2H).

4-[2-(Imidazol-4-ylethyloxy]benzoyl-2(S)-phenylsulfonylamino-β-alanine (25-8)

A mixture of 25-7 (94 mg, 0.17 mmol), 10% Pd/C (94 mg), and 4% formic acid/$CH_3OH$ (50 mL) was stirred under a hydrogen atmosphere at ambient temperature for 4 days. Filtration, concentration of the filtrate, and the flash chromatography (silica, 10:1:1 ethanol/$H_2O$/$NH_4OH$) gave 25-7 as a solid. TLC $R_f$=0.31 (silica, 10:1:1 ethanol/$NH_4OH$/$H_2O$);

$^1$H NMR (400 MHz, $CD_3OD$) δ 7.86 (m, 3H), 7.77 (d, J=11 Hz, 2H), 7.50 (m, 3H), 7.03 (s, 1H), 6.98 (d, J=11 Hz, 2H), 4.28 (t, J=6 Hz, 2H), 3.80–3.50 (m, 3H), 3.12 (t, J=11 Hz, 2H).

SCHEME 26

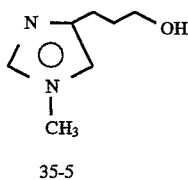

↓ 9-1, $Ph_3P$, DIAD, THF

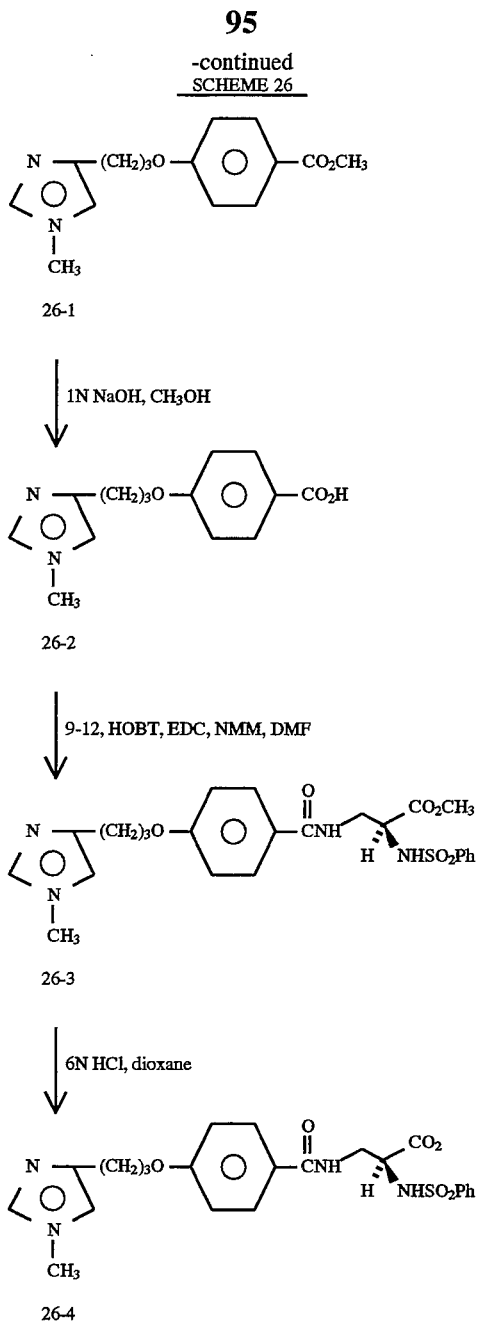

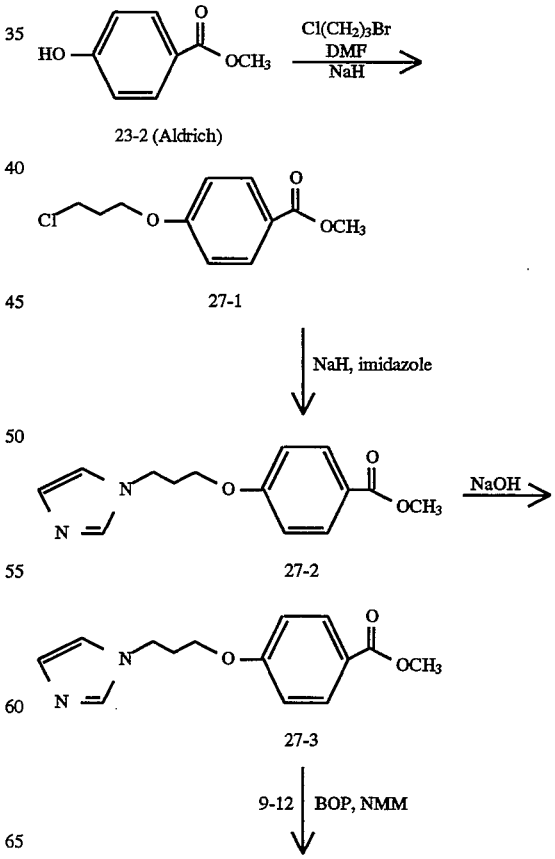

Utilizing the procedure for coupling 25-5 and 19-2a to furnish 25-6, 26-2 (310 mg, 1.2 mmol) was coupled to 9-12 (351 mg, 1.2 mmol) to afford 26-3 as a cream-colored solid after flash chromatography (silica, 95% (CHCl₃/NH₃)/CH₃OH); TLC $R_f$=0.21 (silica, 95% (CHCl₃/NH₃)/CH₃OH);

¹H NMR (300 MHz, CDCl₃) δ 7.82 (m, 2H), 7.69 (d, J=11 Hz, 2H), 7.50 (m, 3H), 7.36 (s, 1H), 7.02 (m, 1H), 6.84 (d, J=11 Hz, 2H), 6.62 (s, 1H), 4.13 (m, 1H), 4.00 (t, J=6 Hz, 2H), 3.85-3.60 (m, 2H), 3.62 (s, 3H), 3.57 (s, 3H), 2.72 (m, 2H), 2.13 (m, 2H).

4-[3-(1-Methylimidazoyl-4-yl)propyloxy]benzoyl-2(S)-phenylsulfonyl-amino-β-alanine (26-4)

A solution of 26-3 (560 mg, 1.1 mmol), dioxane (25 mL), and 1N HCl (25 mL) was stirred for 24 hours at ambient temperature. Concentration and then flash chromatography (silica, ethanol/NH₄OH)H₂O 9:0.5:0.5) gave 26-4 as a solid. TLC $R_f$=0.29 silica, 9:0.5:0.5 ethanol/-NH₄OH)H₂O.

¹H NMR (300 MHz, CD₃OD) δ 8.11 (s, 1H), 7.85 (m, 2H), 7.74 (d, J=11 Hz, 2H), 7.50 (m, 3H), 7.06 (s, 1H), 5.93 (d, J=11 Hz, 2H), 4.07 (t, J=6 Hz, 2H), 3.90–3.50 (m, 3H), 3.75 (s, 3H), 2.80 (m, 2H), 2.13 (m, 2H).

Methyl 4-[3-(1-Methylimidazoyl-4-yl)propyloxy]benzoate (26-1)

Utilizing the procedure for converting 25-3 to 25-4, 35-5 (743 mg, 4.9 mmol) was converted to 26-1 after flash chromatography (silica, 40% (CHCl₃/NH₃)/EtOAc). TLC $R_f$=0.15 (silica, 40% (CHCl₃/NH₃)/EtOAc);

¹H NMR (300 MHz, CDCl₃) δ 7.99 (d, J=11 Hz, 2H), 7.33 (s, 1H), 6.91 (d, J=11 Hz, 2H), 6.62 (s, 1H), 4.05 (t, J=6 Hz, 2H), 3.88 (s, 3H), 3.62 (s, 3H), 2.76 (t, J=6 Hz, 2H), 2.16 (m, 2H).

4-[3-(1-Methylimidazoyl-4-yl)propyloxy]benzoic acid (26-2)

Utilizing the procedure for converting 25-4 to 25-5, 26-1 (420 mg, 1.5 mmol) furnished 26-2 as a colorless solid.

¹H NMR (300 MHz, CD₃OD) δ 8.77 (s, 1H), 7.97 (d, J=11 Hz, 2H), 7.35 (s, 1H), 6.96 (d, J=11 Hz, 2H), 4.13 (t, J=6 Hz, 2H), 3.88 (s, 3H), 2.93 (m, 2H), 2.17 (m, 2H).

4-[3-(1-Methylimidazoyl-4-yl)propyloxy]benzoyl-2(S)-phenylsulfonylamino-β-alanine methyl ester (26-3)

-continued
SCHEME 27

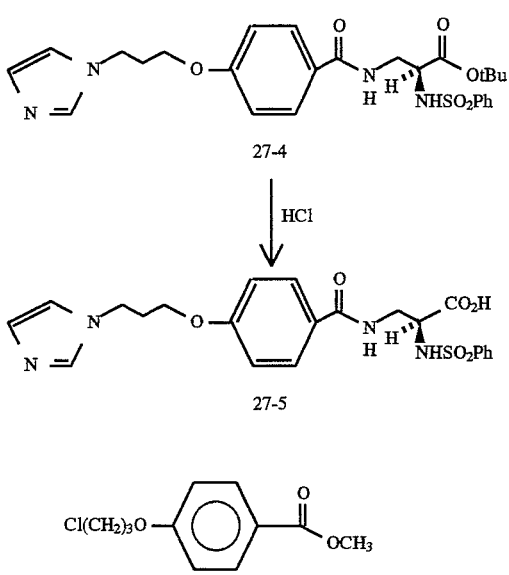

Methyl 4-[(3-chloropropyl)oxy]benzoate (27-1)

A solution of Methyl 4-hydroxy benzoic acid (23-2) (Aldrich) (4.56 g, 30 mmol) in DMF (100 mL) was treated with $Cs_2CO_3$ (14.67 g, 45 mmol) at room temperature. After 0.5 hours, 3-bromo-1-chloropropane (5.94 mL, 60 mmol) was added and the solution was stirred for 4 hours. The reaction mixture was filtered and concentrated to give 27-1 as a white solid. $R_f$ (10% EtOAc/hexanes) 0.36.

$^1$H NMR (400 MHz, $CDCl_3$) δ 8.0 (d, 2H), 6.9 (d, 2H), 4.17 (t, 2H), 3.88 (s, 3H), 3.75 (t, 2H), 2.26 (m, 2H).

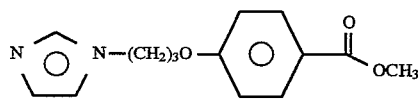

Methyl 4-[3-(1-Imidazolyl)propyloxy]benzoate (27-2)

A solution of imidazole (2.38 g, 34.6 mmol) in DMF (30 mL) was treated with NaH (1.38 g, 34.6 mmol, 60% dispersion) and the mixture was heated to 100° C. for 20 minutes. A solution of 27-1 (7.5 g 34.6 mmol) in 5 mL DMF was added and the reaction was heated (100° C.) for 5 hours. The solvent was removed in vacuo and the residue was dissolved in water and extracted with $CHCl_3$. The organic layers were washed with water, dried ($Na_2SO_4$), concentrated, and chromatographed using a gradient ($CHl_3 \rightarrow 3\%$ $CH_3OH/CHCl_3$). The compound was further purified by medium pressure HPLC to give 27-2 as a yellow oil. $R_f$ (3% $CH_3OH/CHCl_3$) 0.10.

$^1$H NMR (300 MHz, $CDCl_3$) δ 8.0 (d, 2H), 7.99 (s, 1H), 7.08 (s, 1H), 6.90 (m, 3H), 4.2 (t, 2H), 3.96 (t, 2H), 3.90 (s, 3H), 2.26 (m, 2H).

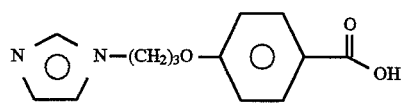

4-[3-(1-Imidazoly)propyloxy]benzoic acid (27-3)

A solution of 27-2 (5.0 g, 19.2 mmol) in EtOH (100 mL) was treated with 1N NaOH (20.2 mL) for 20 hours. The solution was concentrated and 27-3 was used without further purification. $R_f$ (9:1:1 $CHCl_3/CH_3OH/HOAc$) 0.27.

$^1$H NMR (400 MHz, DMSO) δ 7.82 (d, 2H), 7.62 (s, 1H), 7.20 (s, 1H), 6.88 (s, 1H), 6.83 (d, 2H), 4.14 (t, 2H), 3.90 (t, 2H), 2.18 (m, 2H).

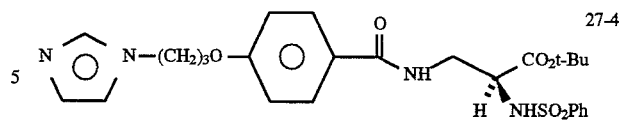

4-[3-(1-Imidazolyl)propyloxy]benzoyl-2(S)-phenylsulfonylamino-β-alanine t-butyl ester (27-4)

A solution of 27-3 (0.6 g, 2.44 mmol) in $CH_3CN$ (20 mL) was treated with 9-12 (0.74 g, 2.44 mmol), BOP reagent (1.08 g, 2.44 mmol) and N-methylmorpholine (1.2 mL, 11 mmol) at room temperature for 24 hours. The reaction was concentrated and chromatographed (5% $CH_3OH/CHCl_3$ saturated with $NH_3$) to give 27-4 as a colorless oil. $R_f$ (10% $CH_3OH/CHCl_3$ saturated with $NH_3$) 0.59.

$^1$H NMR (300 MHz, $CDCl_3$) δ 7.90 (d, 2H), 7.82 (d, 2H), 7.6 (m, 1H), 7.55 (m, 3H), 7.1 (s, 1H), 6.95 (m, 3H), 6.7 (m, 1H), 5.75 (m, 1H), 4.24 (t, 2H), 4.0 (t, 2H), 3.93 (m, 2H), 3.6 (m, 1H), 2.3 (m, 2H), 1.34 (s, 9H).

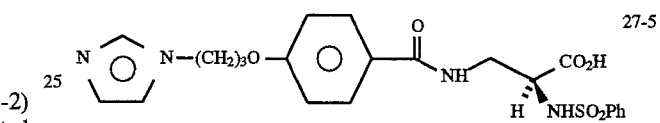

4-[3-(1-Imidazolyl)propyloxy]benzoyl-2(S)-phenylsulfonylamino-β-alanine (27-5)

A solution of 27-4 (1.2 g, 2.27 mmol) in EtOAc (15 mL) was cooled to −78° C. and saturated with HCl gas. This solution was warmed to 0° C. for 1.5 hours, degassed with argon and concentrated to give a colorless oil, which was chromatographed (10:0.5:0.5 $EtOH/H_2O/NH_4OH$) to give 27-5 as a white solid.

$^1$H NMR ($CD_3OD$) δ 8.32 (s, 1H), 7.84 (d, 2H), 7.78 (d, 2H), 7.52 (m, 1H), 7.46 (m, 3H), 7.28 (s, 1H), 6.94 (d, 2H), 4.38 (t, 2H), 4.06 (t, 2H), 3.93 (dd, 1H), 3.68 (dd, 1H), 3.52 (dd, 1H), 2.35 (m, 2H).

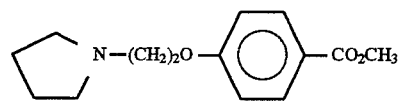

Methyl 4-(2-Pyrrolidinylethyloxy)benzoate (27-6)

Compound 23-2 (2 g, 11.8 mmol) and chloroethylpyrrolidine•HCl (Aldrich) (1.8 g, 11.8 mmol) were treated with NaH (0.94 g, 23.6 mmol) in DMF (30 mL) as described for 27-1 to give 27-6 as a clear oil. $R_f$ (10% $MeOH/CHCl_3$ saturated with $NH_3$) 0.4

$^1$H NMR (300 MHz, $CD_3OD$) δ 7.95 (d, 2H), 7.0 (d, 2H), 4.18 (t, 2H), 3.85 (s, 3H), 2.92 (t, 2H), 2.65 (m, 4H), 1.8 (m, 4H).

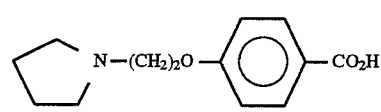

4-[2-(Pyrrolidinyl)ethyloxy]benzoic acid (27-7)

Compound 27-6 (1.5 g, 6.0 mmol) was treated with 6N HCl for 48 hours at room temperature and 60° C. for 2 hours. The solvent was removed to give 27-7 as a white solid.

$^1$H NMR (400 MHz, $D_2O$) δ 7.86 (d, 2H), 6.94 (d, 2H), 4.3 (m, 2H), 3.55 (m, 4H), 3.05 (m, 2H), 2.02 (m, 2H), 1.9 (m, 2H).

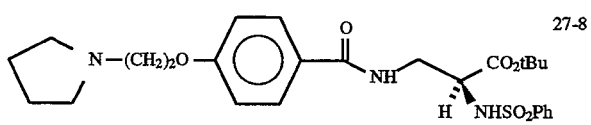

t-Butyl 4-[2-(Pyrrolidinyl)ethyloxy]benzoyl-2(S)-phenylsulfonylamino-β-alanine t-butyl ester (27-8)

27-7 (1.0 g, 3.0 mmol) and 9-12 (0.7 g, 3 mmol) were treated with BOP reagent (1.3 g, 3 mmol) and N-methylmorpholine (10 mL, 9.0 mmol) in $CH_3CN$ (15 mL) as described for 27-3 to give 27-8. $R_f$ (50% $EtOAc/CHCl_3$ saturated with $NH_3$) 0.29.

$^1H$ NMR (400 MHz, DMSO) δ 7.75 (m, 4H), 7.5 (m, 3H), 6.98 (d, 2H), 4.08 (t, 2H), 4.01 (dd, 1H), 3.52 (t, 2H), 3.42 (m, 1H), 3.38 (m, 1H), 2.78 (t, 2H), 2.5 (m, 4H), 2.05 (m, 4H), 1.2 (s, 9H).

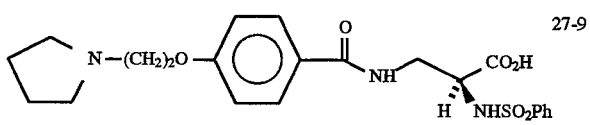

4-[2-(Pyrrolidinyl)ethyloxy]benzoyl-2(S)-phenylsulfonylamino-β-alanine (27-9)

A solution of 27-8 (1.0 g, 2.0 mmol) was dissolved in s EtOAc (7 mL) and treated with HCl gas as described for 27-5. The crude product was purified by preparative HPLC to give 27-9 as the TFA salt. $R_f$ (10:0.5:0.5 $EtOH/NH_4OH/H_2O$) 0.20.

$^1H$ NMR (400 MHz, $D_2O$) δ 7.62 (d, 2H), 7.44 (d, 2H), 7.3 (m, 3H), 6.9 (d, 2H), 4.28 (m, 2H), 4.06 (m, 1H), 3.65–3.55 (m, 5H), 3.3 (m, 1H), 3.08 (m, 2H), 2.05 (m, 2H), 1.9 (m, 2H).

SCHEME 28

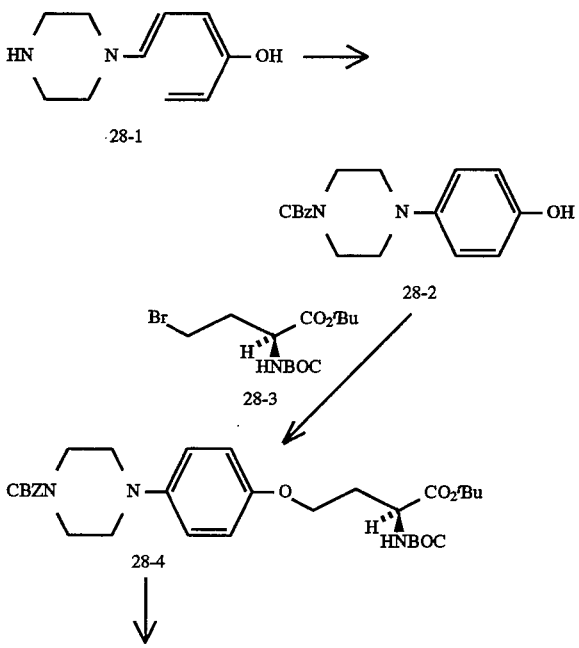

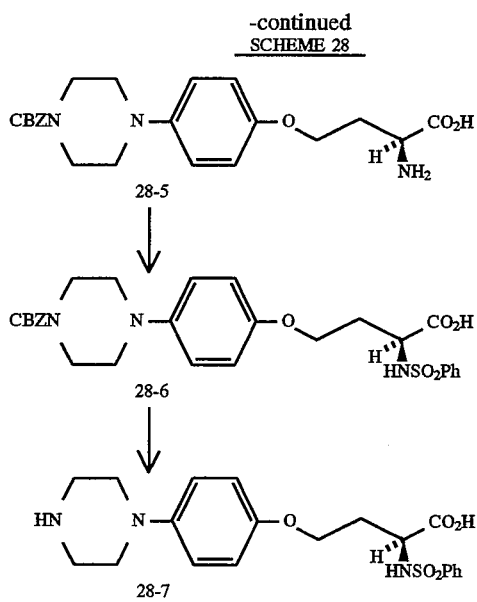

(N-Benzyloxycarbonyl-4-piperazinyl)phenol 28-2

4-Piperazinyl phenol (Schweizerhall, 5 g, 30.5 mmol) was dissolved in THF (150 mL), treated with diisopropylethylamine (12.2 mL, 70.0 mmol), and cooled to 0° C. Benzylchloroformate (4.4 mL, 30.5 mmol) was added and the reaction was allowed to warm to room temperature and stir overnight. The solution was diluted with EtOAc, washed with water and brine, dried over $MgSO_4$, filtered and evaporated to give a brown oil. Column chromatography ($SiO_2$, 40% EtOAc/hexanes) gave 28-2 as a white solid. $R_f$ (40% EtoAc/hexanes) 0.34.

1H NMR (400 MHz, $CDCl_3$) δ 7.4–7.3 (m, 5H), 6.8 (d, 2H), 7.75 (d, 2H), 5.1 (s, 2H), 3.65 (m, 4H), 3.0 (m, 4H).

t-Butyl 2-(S)(t-Butoxycarbonylamino)-4-[4-(N-benzyloxycarbonyl-piperazinyl)phenoxy]butanoate (28-4)

A solution of NaH (2.5 g, 60% dispersion in mineral oil, 1.5 mmol) in DMF (5 mL) was treated with 28-2, (220 mg, 0.7 mmol) and stirred for 10 minutes. A solution of 28-3 (JACS, 1990, 112, 760) (0.2 g, 0.59 mmol) in DMF (2 mL) is added dropwise over 5 minutes. The dark red solution was stirred for 1 hour, then diluted with EtOAc, washed with 10% $KHSO_4$ and brine, dried over $MgSO_4$, filtered and evaporated to yield a tan oil. Coltann chromatography ($SiO_2$, 30% EtOAc/hexanes) gave 28-4 as a colorless oil. $R_f$ (30% EtOAc/hexanes) 0.3.

$^1H$ NMR (400 MHz, $CDCl_3$) δ 7.4–7.3 (m, 5H), 6.86 (d, 2H), 6.81 (d, 2H), 5.22 (bs, 1H), 5.15 (s, 2H), 4.34 (m, 1H), 3.95 (m, 2H), 3.64 (m, 4H), 3.0 (m, 4H), 2.26 (m, 1H), 2.14 (m, 1H), 1.46 (s, 9H), 1.43 (s, 9H).

2-(S)-Amino-4-[4-(N-benzyloxycarbonyl piperazinyl)phenoxy]butanoic acid (28-5)

A solution of 28-4 (1.0 g, 1.8 mmol) in 10 mL EtOAc was cooled to –40° C. and saturated with HCl gas. The solution was warmed to 0° C., then concentrated to give 28-5 as a tan solid. $R_f$ (10:1:1 $EtOH/H_2O/NH_4OH$) 0.18.

$^1H$ NMR (400 MHz, $CD_3OD$) δ 7.6 (d, 2H), 7.4-7.3 (m, 5H), 7.13 (d, 2H), 5.15 (s, 2H), 4.2 (m, 2H), 3.95 (bs, 4H), 3.6 (m, 4H), 2.4 (m, 2H).

2(S)-(Benzenesulfonylamino)-4-[4-(N-benzyloxycarbonyl piperazinyl)-phenoxylbutanoic acid (28-6)

A solution of 28-5 (0.97 g, 2.2 mmol) in $H_2O$ (26 mL) was cooled to 0° C. and treated with 1N NaOH (2.6 mL) and dioxanne (13 mL). The solution was treated simultaneously with benzenesulfonyl chloride (0.56 mL in 1.5 mL dioxane, 4.4 mmol) and 1N NaOH so that the pH of the solution remained >10. The reaction was stirred for 1 hour at 0° C., then treated in a similar manner with another portion of benzene sulfonyl chloride, and stirred for 1 hour. The solution was diluted with 10% KHSO$_4$ and washed with EtOAc. The organic layers were dried (brine, MgSO$_4$), filtered and evaporated to give a tan oil. Column chromatography (9:0.5:0.5 CH$_2$Cl$_2$/MeOH/HOAc) gave 28-6 as a white solid. R$_f$ (9:0.5:0.5 CH$_2$Cl$_2$/MeOH/HOAc) 0.26.

$^1$H NMR (400 MHz, CD$_3$OD) δ 7.8 (d, 2H), 7.42–7.25 (m, 8H), 6.9 (d, 2H), 6.7 (d, 2H), 5.12 (s, 2H), 4.03 (dd, 1H), 3.85 (m, 2H), 3.67 (bs, 4H), 3.0 (4H), 2.18 (m, 1H), 1.95 (m, 1H).

2(S)-Phenylsulfonylamino-4-(4-piperazinylphenoxy)butanoic acid (28-7)

Compound 28-6 (0.4 g, 0.7 mmol) was treated with 29% HBr/HOAc for 25 minutes, then concentrated to give a yellow oil. Column chromatography (10:0.5:0.5 EtOH/NH$_4$OH/H$_2$O) gave pure 28-7. R$_f$ (10:0.5:0.5 EtOH/H$_2$O/NH$_4$OH) 0.17.

$^1$H NMR (400 MHz, D$_2$O) δ 7.66 (d, 2H), 7.23 (m, 3H), 7.19 (d, 2H), 6.74 (d, 2H), 4.02 (m, 1H), 3.8 (m, 1H), 3.7 (m, 1H), 3.6 (m, 4H), 3.5 (m, 4H), 2.2–1.8 (m, 2H).

4-(N-methyl piperazinyl)phenol (29-3)

In separate dropping funnels, 29-1 (5.8 g, 30 mmol) in 100 mL acetone and 29-2 (3.27 g, 30 mmol) in 100 mL acetone were added over a period of 1.5 hours to a reaction vessel containing 160 mL H$_2$O and 120 mL acetone at reflux 30 minutes after addition was completed the acetone was removed in vacuo and the aqueous phase was basified with bicarbonate, saturated with NaCl and extracted with EtOAc. The organic layer was evaporated to give a brown-orange solid. Column chromatography (SiO$_2$, 15% CH$_3$OH/CHCl$_3$) gave 29-3 as a yellow solid. R$_f$ (20% CH$_3$OH/CHCl$_3$) 0.38.

$^1$H NMR (300 MHz, CDCl$_3$) δ 6.8 (d, 2H), 6.7 (d, 2H), 3.1 (m, 4H), 2.6 (m, 4H), 2.3 (s, 3H).

t-Butyl 2(S)-t-Butyloxycarbonylamino-4-[4-N-methylpiperazinyl)-phenoxy]butanoate (29-4)

To a suspension of NaH (0.09 g, 3.75 mmol) in DMF (8 mL) was added 29-3 (0.3 g, 1.65 mmol). After 10 minutes of stirring, 28-3 (0.5 g, 1.5 mmol) was added and the reaction was stirred overnight. The solution was diluted with EtOAc, washed with 10% KHSO$_4$ and brine, dried (MgSO$_4$) filtered and evaporated. Column chromatography (SiO$_2$, 5% CH$_3$OH/EtOAc) gave 29-4 as a white solid. R$_f$ (10% CH$_3$OH/EtOAc) 0.43.

SCHEME 29

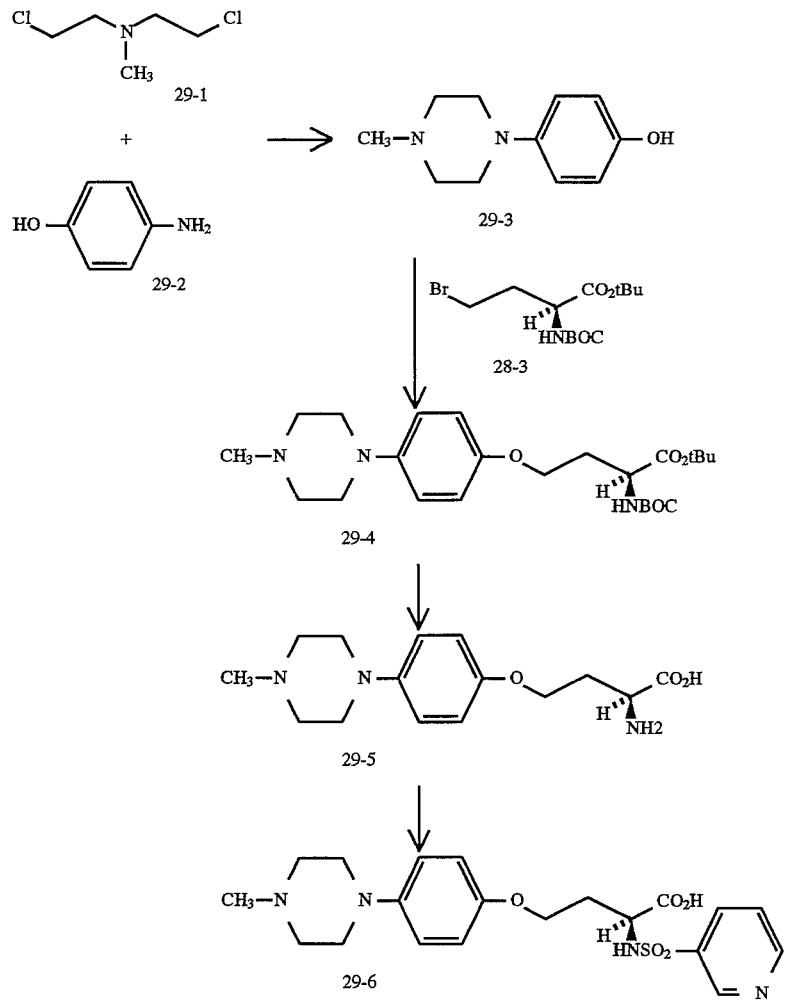

¹H NMR (400 MHz, CD₃OD) δ 6.94 (d, 2H), 6.85 (d, 2H), 4.22 (dd, 1H), 3.98 (m, 2H), 3.1 (m, 4H), 2.66 (t, 4H), 2.37 (s, 3H), 2.22 (m, 1H), 2.0 (m, 1H), 1.46 (s, 9H), 1.41 (s, 9H).

2(S)-Amino-3-[4-(N-methylpiperazinyl)phenoxy]butanoic acid (29-5)

A solution of 29-4 (0.06 g, 0.12 mmol) in EtOAc (3 mL) was cooled to −40° C. and saturated with HCl gas. The solution was warmed to 0° C., then concentrated to yield 29-5 as an off-white solid. $R_f$ (10:0.1:0.1) EtOH/NH₄OH/H₂O) 0.42.

¹H NMR (300 MHz, CDCl₃) δ 6.99 (d, 2H), 6.85 (d, 2H), 4.1 (m, 3H), 3.55 (m, 4H), 3.0 (m, 2H), 2.9 (s, 3H), 2.3 (m, 2H).

2(S)-3-Pyridylsulfonylamino-4-[4-(N-methylpiperazinyl)-phenoxy]butanoic acid (29-6)

A solution of 29-5 (0.05 g, 0.15 mmol) in H₂O (4 mL) was cooled to 0° C. and treated with 1N NaOH (0.3 mL) and dioxane (2 mL). 3-pyridylsulfonyl chloride (JOC, 1989, 54, 389) (0.03 g, 0.15 mmol) was added, along with enough 1N NaOH to keep the pH of the reaction greater than 10. The reaction was concentrated and chromatographed (SiO₂, 10:0.1:0.1 EtOH/H₂O/NH₄OH) to give 29-6 as an off-white solid. $R_f$ (10:0.1:0.1) EtOH/H₂O/NH₄OH) 0.79.

¹H NMR (400 MHz, CD₃OD) δ 8.8 (s, 1H), 8.5 (d, 1H), 8.1 (d, 1H), 7.28 (m, 1H), 6.85 (d, 2H), 6.7 (d, 2H), 3.85–3.8 (m, 3H), 2.8 (s, 3H), 2.18 (m, 1H), 1.85 (m, 1H).

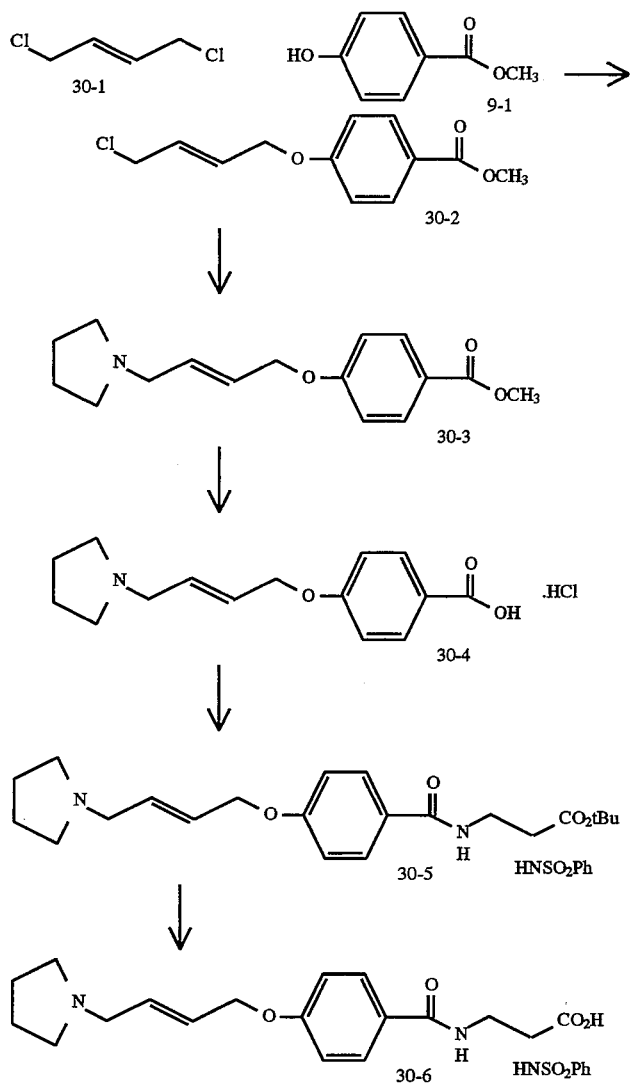

SCHEME 30

Methyl 4(4-chlorobut-2-enyloxy)benzoate (30-2)

A solution of 9-1 (1.2 g, 8 mmol) and 1,4 dichloro 2-butene (1.6 mL, 17 mmol) (30-1) (Aldrich) in DMF (30 mL) was treated with Cs₂CO₃ (3.9 g, 12 mmol) for 24 h. The solvent was removed in vacuo and the residue chromatographed (10% EtOAc/Hexanes) to give 30-2 as a white solid. $R_f$ (20% acetone/hexane) 0.42.

¹H NMR (300 MHz, CDCl₃) δ 8.1 (d, 2H), 7.0 (d, 2H), 6.1 (s, 2H), 4.7 (s, 2H), 4.2 (m, 2H), 3.98 (s, 3H).

Methyl 4-[(4-Pyrrolidinyl-but-2-enyl)oxy)]benzoate (30-3)

A solution of 30-2 (1.3 g, 5.36 mmol) in DMF (15 mL) was treated with pyrrolidine (2.4 mL, 29 mmol) and heated at 80° C. for 78 h. The solvent was removed in vacuo and the residue was absorbed onto SiO₂ and chromatographed (SiO₂, 0–7% CH₃OH in CH₂Cl₂ to give 30-3 as a yellow oil. $R_f$ (10% CH₃OH/CH₂Cl₂) 0.24.

¹H NMR (300 MHz, CDCl₃) δ 8.0 (d, 2H), 6.9 (d, 2H), 6.0 (m, 2H), 4.6 (d, 2H), 3.85 (s, 3H), 3.28 (d, 2H), 2.7 (m, 4H), 1.85 (m, 4H).

4-[(4-Pyrrolidinylbut-2-enyl)oxy]benzoic acid (30-4)

A solution of 30-3 (1.14 g, 4.14 mmol) in 6 N HCl (30 mL) was heated at 60° C. for 24 h. The solution was concentrated and the residue was chromatographed (SiO₂, 9:1:1 EtOH/H₂O/NH₄OH) to give a dark yellow oil. The HCl salt was prepared by dissolving the oil in CH₂Cl₂ and adding 1M HCl/Et₂O. The solvents were removed and the residue washed with Et₂O to give 30-4 as an off-white solid. R$_f$ (9:1:1 EtOH/H₂O/NH₄OH) 0.2.

4-[(4-Pyrrolidinylbut-2-enyl)oxy]benzoyl-2(S)-phenylsulfonylamino-β-alanine t-butyl ester (30-5)

A suspension of 30-4 (0.77 g, 2.6 mmol) in DMF (7 mL) was treated with N-methyl morpholine (1.5 mL, 14 mmol), CDI (0.5 g, 3.1 mmol) and 19-2a (1.0 g, 3.2 mmol). Concentration and chromatography (SiO₂, 5% CH₃OH/CH₂Cl₂), followed by separation by preparative HPLC (reverse phase) gave 30-5 as the TFA salt. R$_f$ (10% CH₃OH/CH₂Cl₂) 0.19.

4-[(4-Pyrrolidinylbut-2-enyl)oxy]benzoyl-2(S)-phenylsulfonylamino-β-alanine (30-6)

The compound 30-5 (0.22 g, 0.43 mmol) was treated with 6N HCl (20 mL) for 24 h at room temperature and 1.5 h at 60° C. Concentration of the solution and chromatography of the residue (SiO₂, 9:1:1 EtOH, H₂O, NH₄OH) gave 30-6 as a white solid. R$_f$ (9:1:1 EtOH/H₂O/NH₄OH) 0.69.

¹H NMR (300 MHz, D₂O) δ 7.72 (d, 2H), 7.55 (d, 2H), 7.5 (m, 3H), 7.0 (d, 2H), 6.2 (m, 1H), 5.9 (m, 1H), 3.85 (dd, 1H), 3.8 (d, 2H), 3.6 (m, 3H), 3.45 (m, 2H), 3.38 (dd, 1H), 3.0 (m, 2H), 2.0 (m, 4H).

SCHEME 31

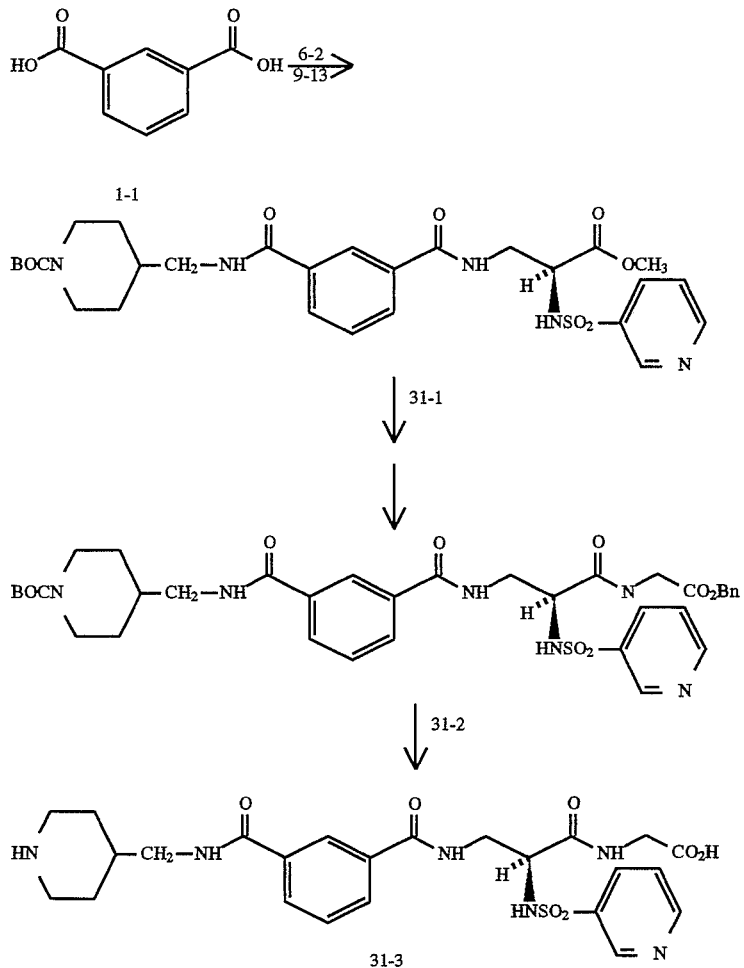

3-[(N-Boc-Piperidin-4-ylmethyl)aminocarbonyl]benzoyl-2(S)-3-pyridylsulfonylamino-β-alanine methyl ester (31-1)

Treatment of 1-1 with CDI, 6-2 and 9-13 as described for 1-2 gave 31-1 after column chromatography (60% acetone/hexanes).

¹H NMR (300 MHz, CDCl₃) δ 9.0 (s, 1H), 8.64 (d, 1H), 8.14 (s, 1H), 8.07 (d, 1H), 7.9 (d, 1H), 7.8 (d, 2H), 7.4-7.3 (m, 3H), 4.33 (m, 1H), 4.1-4.0 (bd, 2H), 3.9-3.65 (m, 2H), 3.57 (s, 3H), 3.2 (bs, 2H), 2.6 (m, 2H), 1.8-1.6 (m, 3H), 1.43 (s, 9H), 1.2-1.0 (m, 2H).

3-[(N-Boc-Piperidin-4-ylmethyl)aminocarbonyl]benzoyl-2(S)-3-pyridylsulfonylamino-β-alanyl-glycine benzyl ester (31-2)

A solution of 31-1 (0.75 g, 1.5 mmol) in 1:1:1 THF/MeOH/H₂O (15 mL) was treated with LiOH•H₂O (0.37 g, 8.8 mmol). After 45 min. the solution was concentrated, diluted with water, washed with EtOAc. The aqueous layer was acidified to pH 2–3 with 10% KHSO₄ and extracted with EtOAc. The organic layer was dried ($Na_2SO_4$), filtered and evaporated to give an acid which was dissolved in acetonitrile (3 mL) and treated with glycine benzyl ester•HCl (0.1 g, 0.5 mmol), N-methylmorpholine (0.11 mL, 0.98 mmol), and BOP reagent (0.26 g, 0.58 mmol) for 24 h. The solution was concentrated, dissolved in water and EtOAc and the layers separated. The organic layer was dried ($Na_2SO_4$), filtered and evaporated. Column chromatography ($SiO_2$, 70% acetone/hexanes) gave 31-2 as a white solid.

$^1$H NMR (300 MHz, $CDCl_3$+$CD_3OD$) δ 8.98 (s, 1H), 8.43 (d, 1H), 8.1 (d, 1H), 7.95 (m, 2H), 7.78 (d, 1H), 7.4–7.3 (m, 5H), 7.2 (m, 2H), 5.1 (s, 2H), 4.18 (dd, 1H), 4.05 (m, 2H), 3.7 (dd, 1H), 3.55 (dd, 1H), 3.3 (m, 2H), 1.8–1.7 (m, 3H), 1.43 (s, 9H), 1.15 (m, 2H).

3-[(Piperidin-4-ylmethyl)aminocarbonyl]benzoyl-2(S)-3-pyridyl-sulfonylamino-β-alanyl-glycine (31-3)

Compound 31-2 (0.12 g) was treated with 6N HCl for 24 h. The solution was concentrated and chromatographed ($SiO_2$, 9:1:1 EtOH/$H_2O$/$NH_4OH$) to give 31-3 as a white solid.

$^1$H NMR (300 MHz, $D_2O$) δ 8.84 (s, 1H), 8.3 (m, 1H), 8.19 (d, 1H), 7.9 (m, 2H), 7.7 (d, 1H), 7.58 (t, 1H), 7.35 (m, 1H), 4.28 (dd, 1H), 3.78 (s, 2H), 3.5–3.35 (m, 6H), 3.0 (t, 2H), 2.0 (m, 3H), 1.5 (m, 2H).

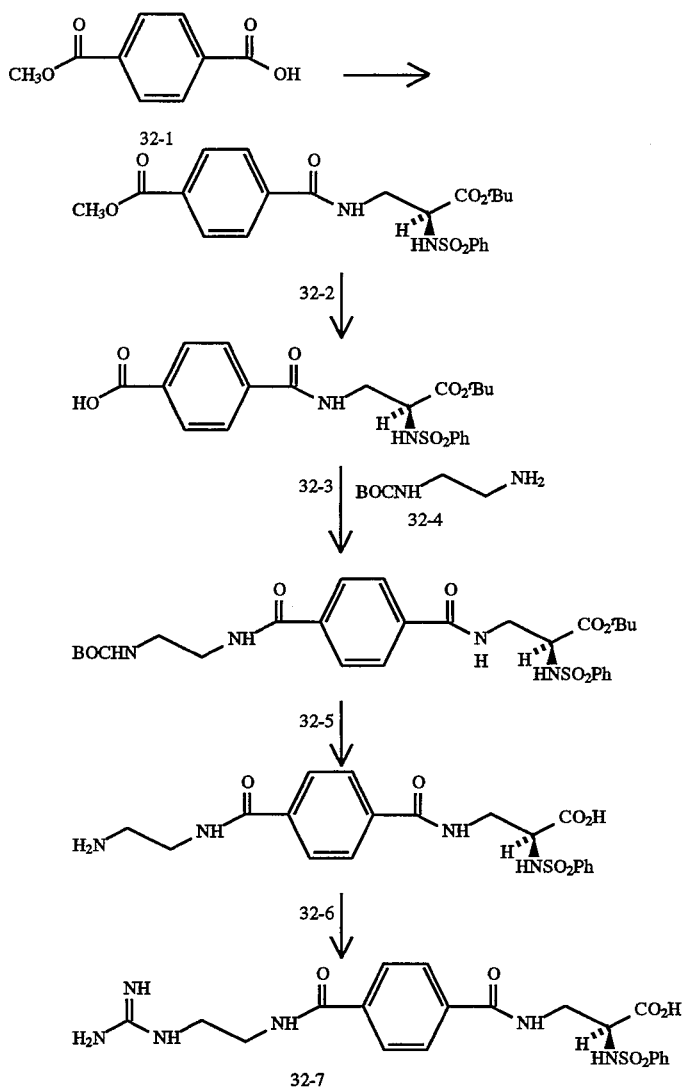

SCHEME 32

4-(Methyloxycarbonyl)benzoyl-2(S)-phenylsulfonylamino-β-alanine t-butyl ester (32-2)

A slurry of mono-methyl terephthalic acid (32-1, Aldrich) (0.25 g, 1.4 mmol) and 19-2a (0.5 g, 1.4 mmol) in acetonitrile (7 mL) was treated with N-methyl morpholine (0.31 mL, 2.8 mmol) and BOP reagent (0.62 g, 1.4 mmol) for 24 h. The solution was diluted with EtOAc, washed with $H_2O$, 10% $KHSO_4$, saturated $NaHCO_3$ and brine. The organic layer was dried over $MgSO_4$, filtered and evaporated to give a tan solid. Column chromatography (40% EtOAc/Hexanes) gave 32-2 as a white solid.

$^1$H NMR (400 MHz, $CDCl_3$) δ 8.1 (d, 2H), 7.8 (m, 4H), 7.59 (m, 1H), 7.50 (m, 2H), 6.8 (m, 1H), 5.6 (d, 1H), 3.98–3.9 (m, 2H), 3.95 (s, 3H), 3.55 (m, 1H), 1.29 (s, 9H).

4-(Carboxyl)benzoyl-2(S)-phenylsulfonylamino-β-alanine t-butyl ester (32-3)

A solution of 32-2 (0.58 g, 1.25 mmol) in 1:1:1 THF/MeOH/$H_2O$ is treated with LiOH (0.1, 1.25 mmol) for 2 h.

The reaction was diluted with 10% KHSO₄ and extracted with EtOAc. The organic layer was washed with H₂O, brine, dried over MgSO₄, filtered and evaporated to give 32-3 as a white solid.

$^1$H NMR (CD₃OD, 400 MHz) δ 8.09 (d, 2H), 7.85 (m, 3H), 7.5 (m, 4H), 4.13 (dd, 1H), 3.7 (m, 1H), 3.52 (m, 1H), 1.23 (s, 9H).

(1-t-Butoxycarbonylamino-2-amino)ethane (32-4)

A solution of ethylenediamine (Aldrich) 18 g, 0.3 mol) in CHCl₃ (300 mL) was treated dropwise with a solution of BOC anhydride (13.1 g, 0.06 mole) in CHCl₃ (100 mL) over 1 h, then stirred overnight. The reaction was filtered and the filtrate concentrated to give 32-4 as a viscous, colorless oil.

$^1$H NMR (300 MHz, CCDl₃) δ 4.9 (bs, 1H), 3.15 (m, 2H), 2.28 (m, 2H), 1.43 (s, 9H), 1.1 (bs, 2H).

4-[2-(N-Boc-Amino)ethylaminocarbonyl]benzoyl-2(S)-phenylsulfonyl-amino-β-alanine t-butyl ester (32-5)

A solution of 32-3 (0.5 g, 1.1 mmol) and 32-4 (0.26 g, 1.67 mmol) in acetonitrile (8 mL) is treated with N-methylmorpholine (0.18 mL, 1.67 mmol) and BOP reagent (0.74 g, 1.67 mmol) for 24 h. The solution is diluted with EtOAc, washed with H₂O, 10% KHSO₄, sat. NaHCO₃, brine, dried over MgSO₄, filtered and evaporated. Column chromatography (80% EtOAc/Hexanes) gave 32-5 as a white solid. R_f (80% EtOAc/Hexanes) 0.22.

$^1$H NMR (400 MHz, CDCl₃) δ 7.7–7.6 (m, 6H), 7.5 (m, 1H), 7.55 (m, 1H), 7.45 (m, 2H), 7.35 (m, 1H), 5.2 (m, 1H), 4.0 (dd, 1H), 3.8 (m, 1H), 3.67 (m, 1H), 3.52 (m, 2H), 3.4–3.3 (m, 2H), 1.42 (s, 9H), 1.27 (s, 9H).

4-[(2-Aminoethyl)aminocarbonyl]benzoyl-2(S)-phenylsulfonylamino-β-alanine (32-6)

A slurry of 32-5 (0.62 g, 1.05 mmol) in EtOAc (15 mL) was cooled to –40° C. and saturated with HCl gas. The reaction was warmed to 0° C., then concentrated to yield 32-6 as a white solid.

$^1$H NMR (400 MHz, CD₃OD) δ 7.9–7.6 (m, 6H), 7.6–7.4 (m, 4H), 4.21 (dd, 1H), 3.75 (dd, 1H), 3.67 (m, 2H), 3.5 (m, 1H), 3.2 (m, 2H).

4-[(2-Guanidinoethyl)aminocarbonyl]benzoyl-2(S)-phenylsulfonyl-amino-β-alanine (32-7)

A solution of 32-6 (0.56 g, 1.2 mmol) in 1:1 DMF/H₂O (8 mL) was treated with diisopropylethylamine (0.63 mL, 3.6 mmol) and N-amidinoimidazole (Fluka, (0.26 g, 1.8 mmol) and heated to 40° C. for 4.5 h. Column chromatography (10:0.2:0.2 EtOH/H₂O/NH₄OH, followed by 10:1:1 EtOH/H₂O/NH₄OH) gave 32-7. R_f (10:1:1 EtOH/H₂O/NH₄OH) 0.10.

$^1$H NMR (400 MHz, DMSO) a 8.8 (m, 2H), 8.4 (s, 1H), 7.91 (d, 2H), 7.78 (d, 2H), 7.75 (d, 2H), 7.5 (m, 7H), 7.0 (bs, 1H), 3.45–3.2 (m, 7H).

SCHEME 33

In order to prepare [3-(Azetidinyl)ethyloxy]phenyl-carbonyl-2(S)-phenylsulfonylamino-β-alanine,

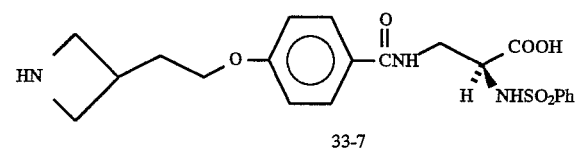

33-7 a procedure similar to the procedure followed in Scheme 9 was used, substituting 1-4 with N-BOC-Azetidin-3-ylethyl iodide (33-6).

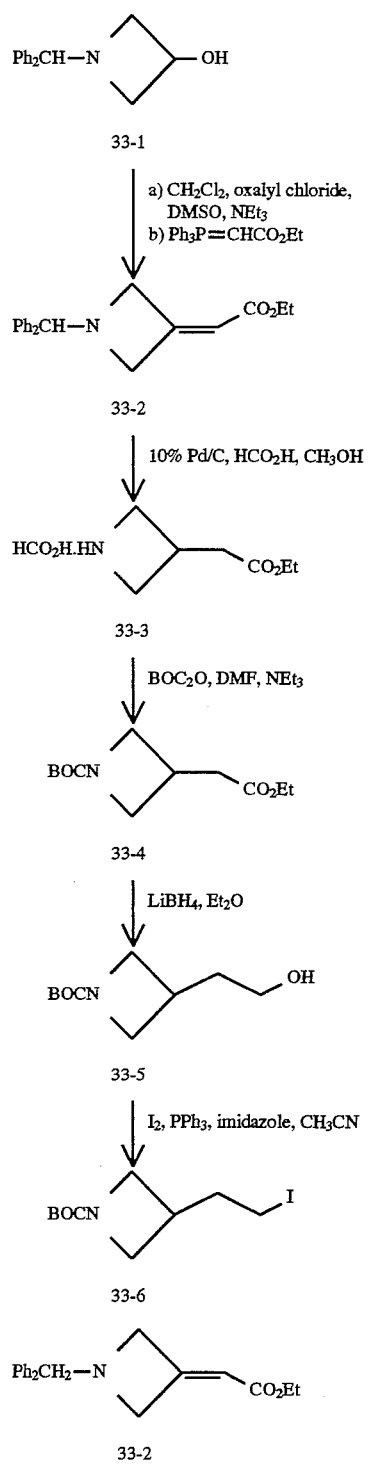

N-Diphenylmethyl-3-(carboethoxymethylidine)-3-azetidine (33 -2)

To a solution of oxalyl chloride (0.10 mL, 1.1 mmol), in CH₂Cl₂ (4.7 mL) at –78° C. was added DMSO (0.12 mL, 1.7 mmol) dropwise. After gas evolution subsided (~5 min), a solution of 33-1 (for preparation see; JOC, 37, 3953, 1972 A. G. Anderson, R. Lok) (0.20 g, 0.84 mmol) in CH₂Cl₂ (1.5 mL) was added. After 30 min., NEt₃ (0.40 mL, 2.8 mmol) was added and after 10 min. the cooling bath removed. After 20 min. TLC analysis indicated no starting material remained. The ylide (0.32 g, 0.92 mmol) was then added and the reaction stirred for 20 h. The reaction mixture was diluted with pet. ether and then washed with H$_2$O, 5% KHSO$_4$, and brine, dried (MgSO$_4$), and concentrated. Flash chromatography (silica, (15% EtOAc/hex) gave 33-2 (0.14 g) as a colorless oil. R$_f$ 0.43 (silica, 15% EtOAc/hexanes).

$^1$H NMR (300 MHz, CDCl$_3$) δ 7.50–7.10 (m, 10H), 5.65 (m, 1H), 4.52 (s, 1H), 4.16 (m, 2H), 4.14 (q, J=7 Hz, 2H), 3.89 (m, 2H), 1.22 (t, J=7 Hz, 3H).

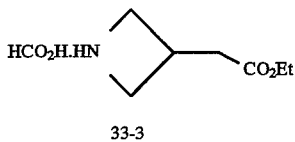

33-3

Ethyl Azetidin-3-ylacetate-formate (33-3)

A mixture of 33-2 (3.2 g, 10.3 mmol), 4.4% HCO$_2$H/ CH$_3$OH (317 mL), and 10% Pd/C (0.63 g) was stirred under a hydrogen atmosphere (1 atm) at ambient temperature. After stirring over the weekend the reaction mixture was filtered through a celite pad and the filtrate concentrated to give 33-3 as a colorless oil as used directly for the next reaction.

$^1$H NMR (300 MHz, CDCl$_3$) δ 9.90 (bs, 2H), 8.37 (s, 2H), 4.19 (m, 2H), 4.17 (q, J=7 Hz, 2H), 3.89 (m, 2H), 3.26 (m, 1H), 2.72 (d, J=8 Hz, 2H), 1.26 (t, J=7 Hz, 3H).

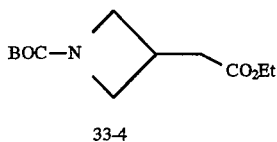

33-4

Ethyl N-BOC-azetidin-3-ylacetate (33-4)

A stirred solution of 33-3 (10.3 mmol), DMF (50 mL), and NEt$_3$ (5.0 mL, 36.0 mmol) at 0° C. was treated with BOC20 (2.5 g, 11.3 mmol) followed by removal of the cooling bath. After 20 h, the reaction mixture was diluted with EtOAc and then washed with H$_2$O, 5% KHSO$_4$, sat. NaHCO$_3$, and brine, dried (MgSO$_4$), and concentrated. Flash chromatography (silica, 30% EtOAc/hexanes) gave 33-4 (1.0 g) as a colorless oil. R$_f$ 0.44 (silica, 30% EtOAc/hexanes).

$^1$H NMR (300 MHz, CDCl$_3$) δ 4.13 (q, J=7 Hz, 2H), 4.01 (m, 2H), 3.60 (dd, J=9, 6 Hz, 1H), 2.88 (m, 1H), 2.61 (d, J=8 Hz, 2H), 1.44 (s, 9H) 1.25 (t, J=7 Hz, 3H).

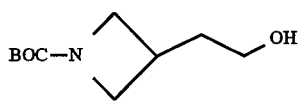

33-5

N-BOC-Azetidin-3-ylethanol (33-5)

A stirred solution of 33-4 (0.96 g, 3.9 mmol) in ether (20 mL) at ambient temperature was treated with LiBH$_4$ (0.34 g, 15.8 mmol) then heated to 55° C. After 45 min the cooled reaction was quenched with 5% KHSO$_4$ (10 mL) and then diluted with EtOAc. The organic phase was washed with 5% KHSO$_4$ and brine, dried (MgSO$_4$), and concentrated to give 33-5 (0.79 g) as a colorless oil. R$_f$ 0.46 (silica, EtOAc).

$^1$H NMR (300 MHz, CDCl$_3$) δ 4.04 (m, 2H), 3.70–3.50 (m, 4H), 2.63 (m, 1H), 1.83 (m, 2H), 1.44 (s, 9H).

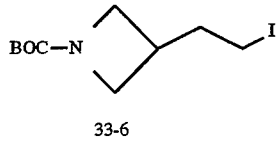

33-6

N-BOC-Azetidin-3-ylethyl iodide (33-6)

A stirred solution of 33-5 (0.78 g, 3.8 mmol), PPh$_3$ (1.1 g, 4.3 mmol), imidazole (0.40 g, 5.8 mmol), and CH$_3$CN (20 mL) at 0° C. was treated with iodine (1.0 g, 4.3 mmol). After 15 min the cooling bath was removed and stirring continued for 5 h. The reaction mixture was then diluted with H$_2$O and extracted with hexanes (5×25 mL then 4×50 mL). The combined extracts were dried (MgSO$_4$) and concentrated. Flash chromatography (silica, 20% EtOAc/hexanes) gave 33-6 (0.99 g) as a colorless oil. R$_f$ 0.44 (silica, 20% EtOAc/hexanes).

$^1$H NMR (400 MHz, CDCl$_3$) δ 4.04 (t, J=7 Hz, 2H), 3.57 (dd, 2H), 3.10 (t, 2H), 2.64 (m, 1H), 2.16 (q, 2H), 1.43 (s, 9H).

Substituting 33-6 for 1-4 in Scheme 9, 33-7 is formed.

SCHEME 34

In order to prepare 4-[3-(Azetidin-3-yl)propyloxy] benzoyl-2(S)-phenylsulfonylamino-β-alanine

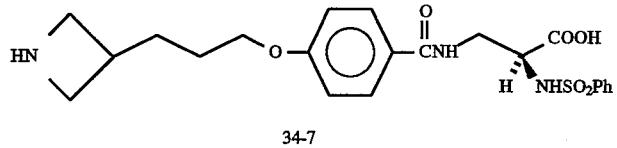

34-7 a procedure similar to the procedure followed in Scheme 33 may be used, substituting 33-5 with 3-(N-BOC-Azetidin-3-yl)propanol (34-6).

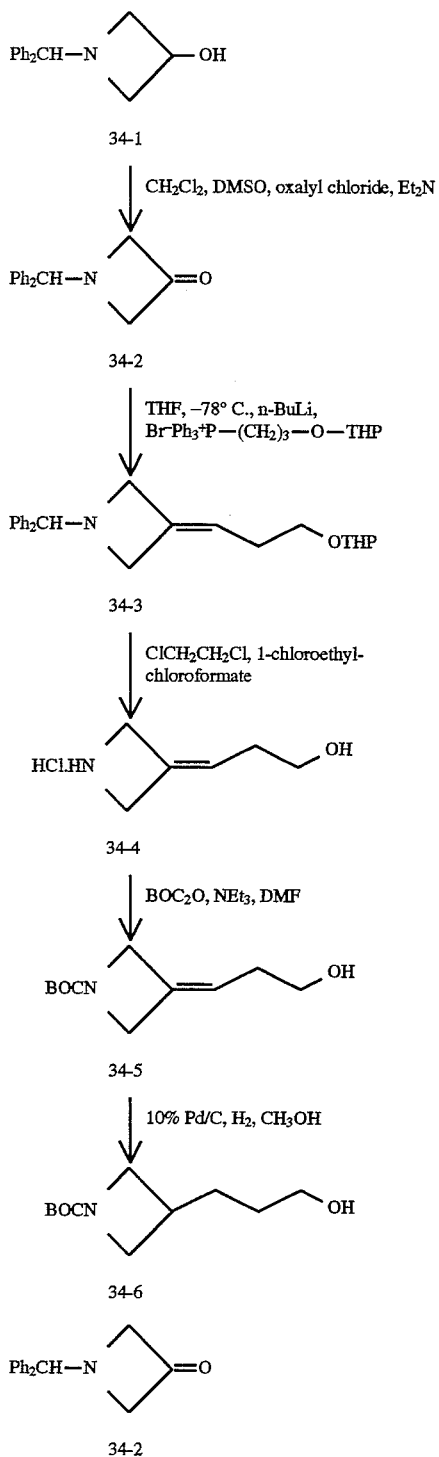

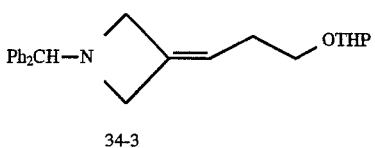

2-[(N-Diphenylmethyl-azetidin-3-yl)methylidine]ethyloxy-tetrahydropyran ether (34-3)

A mixture of the phosphonium salt (for preparation see; Schow, S. R., McMorris, T. C., JOC, 44, 3760, 1979) (32.5 g, 66 mmol) in THF (300 mL) at −78° C. was treated with n-BuLi (44.6 mL, 71 mmol, 1.6 M/hexanes) dropwise then stirred for 1.0 h. The ketone 34-2 (15.4 g, 65 mmol) was then added followed by removal of the cooling bath. After 20 h, the reaction mixture was diluted with EtOAc then washed with H$_2$O, and brine, dried (MgSO$_4$), and concentrated. Flash chromatography (silica, 10% EtOAc/hexanes) gave 34-3 (5.8 g) as an oil. R$_f$ 0.50 (silica, 20% EtOAc/hexanes). $^1$H NMR (400 MHz, CDCl$_3$) 7.50–7.20 (m, 10H), 5.24 (bs, 1H), 4.56 (m, 1H), 4.48 (bs, 1H), 3.90–3.65 (m, 6H), 3.48 (m, 1H), 3.37 (m, 1H), 2.15 (m, 2H), 1.85–1.45 (m, 6H).

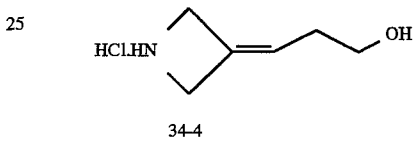

2-[(3-Dehydroazetidin-3-yl)methylene]ethanol (34-4)

To a stirred solution of 34-3 (2.4 g, 6.63 mmol) in CH$_2$Cl$_2$ (66 mL) at 0° C. was added 1-chloroethyl chloroformate (0.73 mL, 6.65 mmol) followed by refluxing for 4.0 h. The reaction mixture was concentrated and the residue dissolved in CH$_3$OH (66 mL) and refluxed for 1 h. Concentration gave crude 34-4 as an orange oil. R$_f$ 0.18 (silica, 4:1:1 CH$_2$Cl$_2$/CH$_3$OH/AcOH).

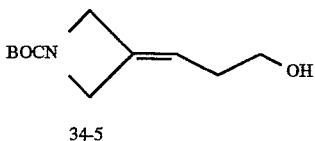

2-[(N-BOC-3-Dehydroazetidin-3-yl)methylene]ethanol (34-5)

A solution of 34-4 (2.4 g, 6.63 mmol), DMF (66 mL), and NEt$_3$ (1.1 mL, 8.0 mmol) at ambient temperature was treated with BOC$_2$O (1.7 g, 8.0 eq). After 1.0 h, the reaction mixture was diluted with EtOAc and then washed with 10% KHSO$_4$, H$_2$O and brine, dried (MgSO$_4$), and concentrated. Flash chromatography (silica, 60% EtOAc/hexanes) gave 34-5 (560 mg). R$_f$ 0.51 (silica, EtOAc).

$^1$H NMR (300 MHz, CDCl$_3$) δ 5.33 (m, 1H), 4.47 (m, 4H), 3.65 (m, 2H), 2.19 (m, 2H), 1.44 (s, 9H).

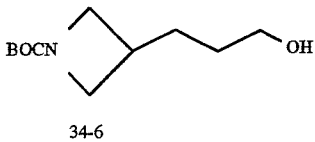

3-(N-BOC-Azetidin-3-yl)propanol (34-6)

A mixture of 34-5 (560 mg, 2.62 mmol), CH$_3$OH (26 mL), and 10% Pd/C (112 mg) was stirred under a hydrogen N-Diphenylmethyl-azetidin-3-one (34-2)

To a stirred solution of oxalyl chloride (8.7 mL) in CH$_2$Cl$_2$ (400 mL) at −78° C. was added DMSO (10.3 mL, 0.13 mol) dropwise. After gas evolution subsided, the alcohol 34-1 (17.5 g, 73 mmol) in CH$_2$Cl$_2$ (200 mL) was added. After 15 min, the white suspension was treated dropwise with NEt$_3$ (51.4 mL, 0.36 mol). After addition was complete, the cooling bath was removed and stirring was continued for 2 h. The reaction mixture was diluted with CH$_2$Cl$_2$ and then washed with H$_2$O and brine, dried (MgSO$_4$) and 34-2 conc. to a yellow oil. R$_f$ 0.63 (silica, 30% EtOAc/hexanes). $^1$H NMR (400 MHz, CDCl$_3$) δ 7.50–7.20 (m, 10H), 4.59 (s, 1H), 4.00 (s, 4H).

atmosphere (1 atm) at ambient temperature. After 20 h, the reaction mixture was filtered through a celite pad and the filtrate concentrated to give 34-6 (529 mg) as a yellow oil. $R_f$ 0.38 (silica, EtOAc).

$^1$H NMR (400 MHz, CDCl$_3$) δ 3.99 (t, 2H), 3.64 (t, 2H), 3.53 (dd, 2H), 2.50 (m, 1H), 1.70–1.50 (m, 2H), 1.45 (s, 9H).

Substituting 34-6 for 33-5 in Scheme 33, 34-7 is formed.

H$_2$O and the layers were separated. The water layer was basified to pH 11 with saturated NaHCO$_3$ and extracted with EtOAc and CH$_2$Cl$_2$. The organic layers were combined and evaporated. The residue was chromatographed (5% CH$_3$OH/ CHCl$_3$ saturated with NH$_3$) to give 35-3 as a white solid.

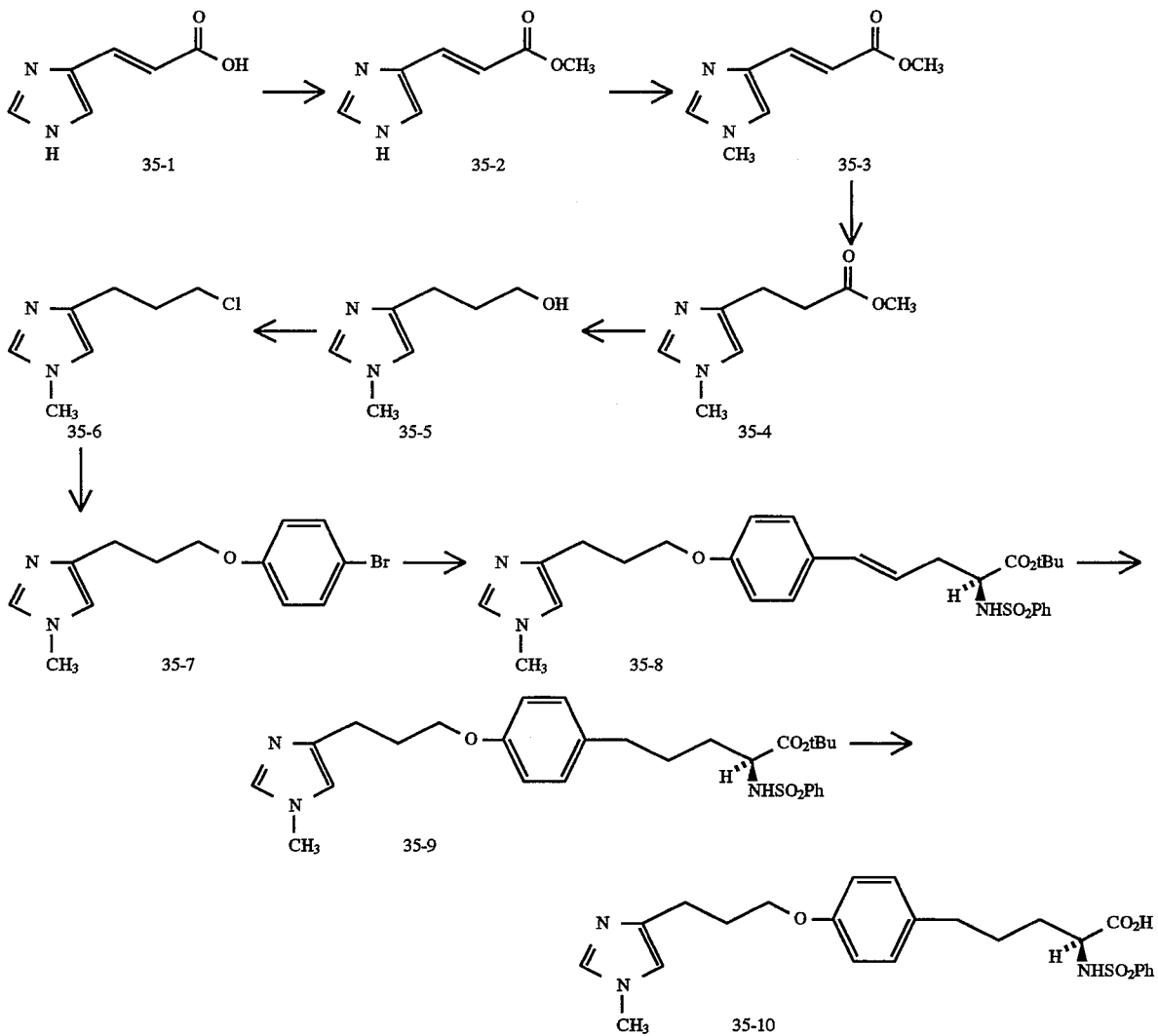

SCHEME 35

Methyl 3-(Imidazol-4-yl)-2-propenoate hydrochloride (35-2)

A slurry of uraconic acid (35-1) (Aldrich) 22.6 g, 16.5 mmol) in CH$_3$OH (200 mL) was saturated with HCl gas and allowed to stir overnight. The slurry was concentrated to give 35-2 as a white solid.

$R_f$ (5% CH$_3$OH/EtOAc) 0.676.

$^1$H NMR (400 MHz, CD$_3$OD) δ 9.03 (s, 1 H), 7.9 (s, 1H), 7.59 (d, 1H), 6.71 (d, 1H), 3.78 (s, 3H).

Methyl 3-(1-Methylimidazol-4-yl)-2-propenoate (35-3)

NaH (0.85 g of a 60% dispersion in oil, 21.2 mmol) was placed in a flask, suspended in hexanes, and allowed to settle. The hexanes was decanted and DMF (50 mL) was added, followed by 35-2 (2 g, 10.6 mmol). After 10 minutes methyl iodide (0.79 mL, 12.7 mmol) was added. After stirring for 24 hr the solution was diluted with EtOAc and $R_f$ (50% acetone/hexanes) 0.22

$^1$H NMR (400 MHz, CD$_3$OD) δ 7.63 (s, 1H), 7.5 (d, 1H), 7.39 (s, 1H), 6.41 (d, 1H), 3.72 (s, 3H), 3.71 (s, 3H).

Methyl 3-(1-Methylimidazol-4-yl) propanoate (35-4)

A solution of 35-3 (3.8 g, 24.7 mmol) in CH$_3$OH (75 mL) was flushed with argon and 10% Pd/Carbon (0.8 g as a slurry in CH$_3$OH) was added. The reaction was placed under hydrogen (balloon pressure) and stirred for 24 hr. The slurry was filtered and the filter cake (Solka-Floc) was washed with CH$_3$OH. The filtrate was concentrated and the residue was dissolved in EtOAc, washed with saturated NaHCO$_3$, dried (Na2SO$_4$) filtered and evaporated. Chromatography (SiO$_2$, 60% acetone/hexanes) gave 35-4 as a yellow oil.

$R_f$ (50% acetone/hexanes) 0.19.

$^1$H NMR (300 MHz, CDCl$_3$) δ 7.31 (s, 1H), 6.63 (2, 1H), 3.67 (s, 3H), 3.62 (s, 3H), 32.88 (t, 2H), 2.67 (t, 2H).

3-(1-Methylimidazol-4-yl)propan-1-ol (35-5)

A solution of 35-4 (1.5 g, 8.9 mmol) in THF (30 mL) was treated with lithium aluminum hydride (1M in THF, 5.5 mL, 55 mmol). After 1.5 hr the reaction is quenched with sodium/potassium tartrate solution and extracted with EtOAc. The aqueous layer was concentrated to dryness and the residue was triturated with EtOAc, then with $CH_2Cl_2$, then with 10:1 $CHCl_3/CH_3OH$. The organic extracts were all combined and concentrated to give 35-5.

$R_f$ (10% $CH_3OH/CHCl_3$) 0.33

$^1$H NMR (400 MHz, $CD_3OD$) δ 7.46 (s, 1H), 6.79 (s, 1H), 3.64 (s, 3H), 3.56 (t, 2H), 2.57 (t, 2H), 1.81 (m, 2H).

1-Chloro-3-(1-methylimidazol-4-yl)propane (35-6)

Compound 35-5 (0.8 g, 6.45 mmol) was added portionwise to thionyl chloride (2.5 mL) with stirring. After 4 hr the reaction was concentrated and the residue was chromatographed ($SiO_2$, 10% $CH_3OH/EtOAc$) to give 35-6.

$R_f$ (10% $CH_3OH/EtOAc$) 0.35

$^1$H NMR (400 MHz, $CD_3OD$) δ 8.78 (s, 1H), 7.37 (s, 1H), 3.88 (s, 3H), 3.61 (t, 2H), 2.85 (t, 2H), 2.11 (m, 2H).

1-Bromo-4-[3-(1-methylimidazol-4-yl)propyloxy]benzene (35-7)

A solution of 4-hydroxy bromo-benzene (0.25 g, 1.4 mmol) in DMF (5 mL) was treated with NaH (0.056 g, 1.4 mmol, 60% dispersion in oil). After 15 minutes 35-6 (0.05 g, 0.35 mmol) was diluted with $H_2O$, concentrated, and the residue chromatographed ($SiO_2$, 10% $CH_3OH/EtOAc$) to give 35-7.

$R_f$ (10% $CH_3OH/EtOAc$) 0.25

$^1$H NMR (400 MHz, $CD_3OD$) δ 7.45 (s, 1H), 7.33 (d, 2H), 6.8 (m, 3H), 3.92 (t, 2H), 3.62 (s, 3H), 2.67 (t, 2H), 2.03 (m, 2H).

t-Butyl 2(S)-Phenylsulfonylamino-5-[4-(3-(1-methylimidazol-4-yl)-propyloxy)phenyl]pent-4-enoate (35-8)

A solution of 35-7 (0.2 g, 0.68 mmol) in $CH_3CN$ (5 mL) was treated with 35-11 (0.25 g, 0.8 mmol), triethylamine (0.19 mL, 1.3 mmol), Pd (OAc)2 (0.015 g, 0.068 mmol) and triorthotolyl phosphine (0.125 g, 0.41 mmol) heated to 110° C. for 20 hr. The solution was concentrated and the residue was chromatographed (10% $CH_3OH/EtoAc$) give 35-8 as an off-whim solid.

$R_f$ (10% $CH_3OH/EtOAc$) 0.24

$^1$H NMR (400 MHz, $CD_3OD$) δ 8.72 (s, 1H), 7.81 (d, 2H), 7.55 (m, 1H), 7.49 (t, 2H), 7.32 (s, 1H), 7.21 (d, 2H), 6.8 (d, 2H), 6.42 (d, 1H), 5.92 (m, 1H), 4.02 (t, 2H), 3.86 (s, 3H), 2.88 (t, 2H), 2.5 (m, 2H), 1.2 (s, 9H).

t-Butyl 2(S)-Phenylsulfonylamino-5-[4-(3-(1-methylimidazol-4-yl)-propyloxy)phenyl]pentanoate (35-9)

A solution of 35-8 (0.07 g, 0.146 mmol) in $CH_3OH$ (1 mL) was treated with 10% Pd/carbon (0.017 g) and placed under hydrogen (balloon). After 20 hr the solution was filtered and concentrated. The residue was purified by preparative HPLC (reverse phase, 95:5→50:50 water/acetonitrile) to give 35-9.

$R_f$ (10% $CH_3OH/EtOAc$) 0.19

$^1$H NMR (400 MHz, $D_2O$) δ 8.32 (s, 1H), 7.68 (d, 2H), 7.53 (m, 1H), 7.45 (t, 2H), 6.98 (d, 2H), 6.73 (d, 2H), 3.94 (t, 2H), 3.64 (s, 3H), 3.6 (m, 1H), 2.71 (t, 2H), 2.38 (m, 2H), 1.95 (m, 2H), 1.4 (m, 2H), 1.08 (s, 9H).

2(S)-Phenylsulfonylamino-5-[4-(3-(1-methylimidazol-4-yl)propyloxy)-phenyl]pentanoic acid (35-10)

A solution of 35-9 (0.055 g, 0.127 mmol) in EtOAc (1 mL) was cooled to −78° C., and saturated with HCl gas. The reaction was warmed to 0° C. for ½ hr, then concentrated and the residue chromatographed (20:1:1 $EtOH/NH_4OH/H_2O$) to give 35-10 as a white solid.

$R_f$ (10:1:1 $EtOH/NH_4OH/H_2O$) 0.78

$^1$H NMR (400 MHz, $D_2O$) δ 8.23 (s, 1H), 7.71 (d, 2H), 7.52 (m, 1H), 7.44 (t, 2H), 6.96 (m, 3H), 6.73 (d, 2H), 3.96 (t, 2H), 3.64 (s, 3H), 3.6–3.55 (m, 3H), 2.73 (t, 2H), 2.3 (t, 2H), 1.99 (m, 2H), 1.5-1.3 (m, 3H).

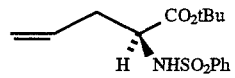

35-11 tert-Butyl 2(S)-Phenylsulfonylaminopent-4-enoate (35-11)

This compound was prepared using the procedure described for 36-4, using phenylsulfonyl chloride as the sulfonylating agent.

SCHEME 36

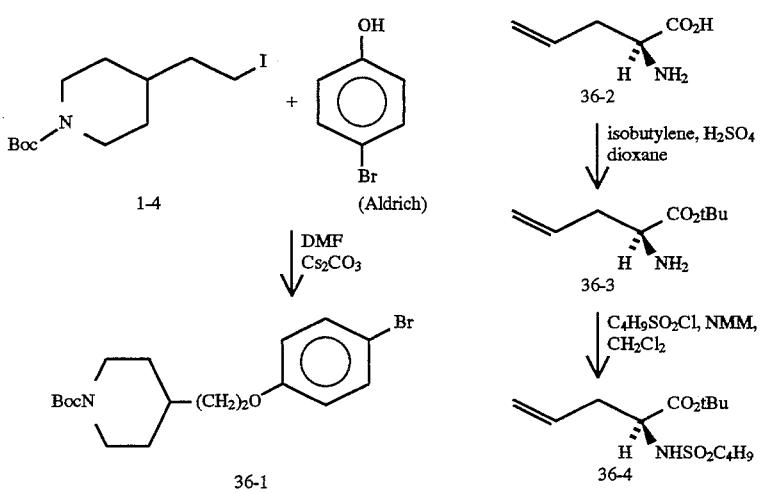

-continued
SCHEME 36

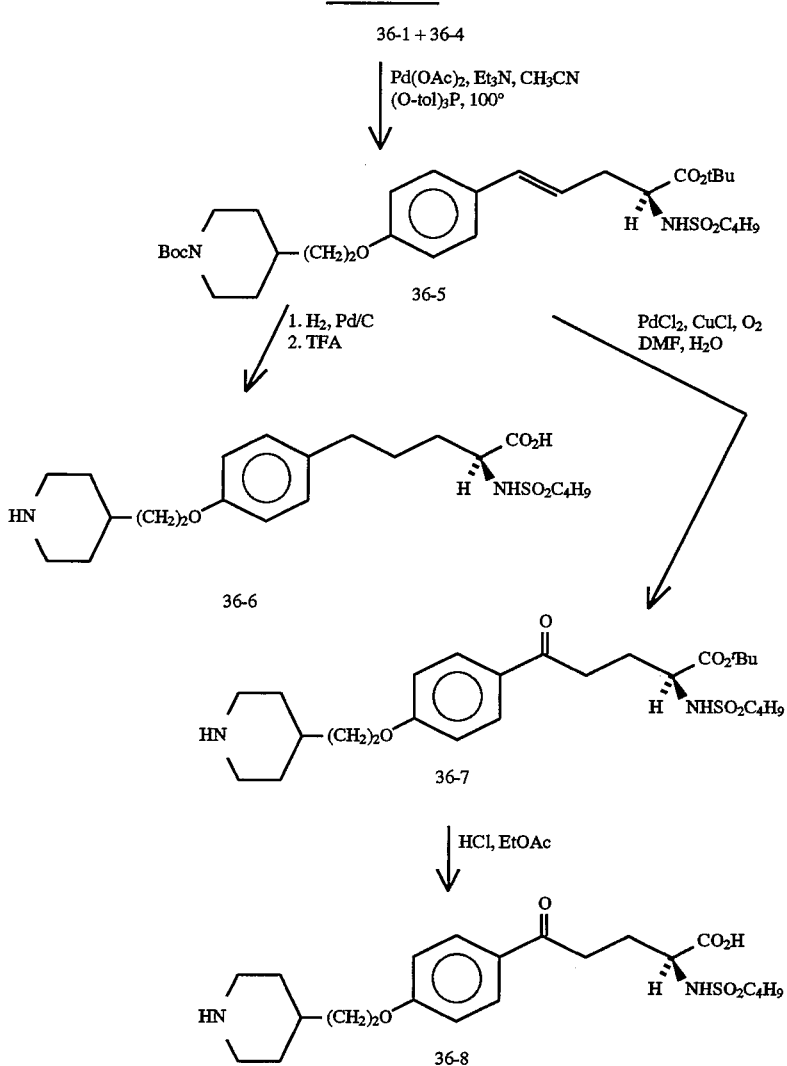

¹-Bromo-4-[2-(N-Boc-piperidin-4-yl)ethyloxy]benzene (36-1)

A mixture of 1-4 (6.45 g, 19.0 mmol), 4-bromophenol (3.29 g, 19 mmol), and $Cs_2CO_3$ (3.10 g, 9.5 mmol) in 50 mL of DMF was stirred at room temperature for 18 hr. The solution was then diluted with 200 mL ethyl acetate and washed with $H_2O$ (4×100 mL), then dried over $Na_2SO_4$, filtered and concentrated. Flash chromatography (silica, 30% EtOAc/hexanes) gave 36-1 as a white solid.

TLC $R_f$=0.45 (silica, 30% EtOAc/hexanes)

¹H NMR (300 MHz, $CDCl_3$) δ 7.34 (d, J=10 Hz, 2HO, 6.78 (d, J=10 Hz, 2H); 4.18 (bn, d, 2H)p 3.97 (t, J=6 Hz, 2H); 2.73 (bnM, 2H), 1.76 (m, 6H), 1.48 (s, 9H), 1.08 (m, 2H).

tert-Butyl 2(S)-Aminopent-4-enoate (36-3)

Liquid isobutylene (100 mL) was slowly added to 36-2 (4.0 g, 34.7 mmol) in a mixture of dioxane (100 ml) and concentrated sulfuric acid (1.5 mL) in a 500 mL pressure bottle. The bottle was sealed and the contents stirred at room temperature for 48 hr. The solution was poured into an ice-cold mixture of ethyl acetate (120 mL) and 1N NaOH (120 mL). The organic layer was removed and the basic aqueous layer extracted with ethyl acetate (2×100 mL). The pooled organic extracts were dried over $Na_2SO_4$ and evaporated to give 36-3 as a colorless oil.

¹H NMR (300 MHz, $CDCl_3$) δ 5.75 (m, 1H), 5.19 (d, J=7.5 Hz, 1H), 5.13 (s, 1H), 3.45 (m, 1H), 2.58–2.32 (m, 2H), 1.65 (br, s, 1H), 1.41 (s, 9H).

tert-Butyl 2(S)-n-Butylsulfonylaminopent-4-enoate (36-4)

A mixture of 36-3 (809 mg, 4.73 mmol) and N-methylmorpholine (0.60 ml, 5.46 mmol) in $CH_2Cl_2$ (15 mL) was cooled to 0° C. under Argon. N-Butyl sulfonyl chloride (0.66 mL, 5.10 mmol) was added and the mixture was allowed to warm to room temperature and stirred for 12 hr. The solution was washed with 10% citric acid $H_2O$, sat. $NaHCO_3$ and brine (10 mL each) then dried over $Na_2SO_4$ filtered and concentrated to give 36-4 as a straw-colored oil.

¹H NMR (300 MHz, $CDCl_3$) δ 5.73 (m, 1H), 5.19 (d, J=7.5 Hz, 1H), 5.13 (s, 1H), 4.93 (d, J=6.8 Hz, 1H), 4.15 (m, 1H), 3.01 (t, J=6.3 Hz, 2H), 2.52 (m, 2H), 1.82 (m, 2H), 1.41 (s, 9H), 0.96 (t, 3H).

tert-Butyl 2(S)-n-Butylsulfonylamino-5-[4-(2-N-Boc-piperidin-4-yl)-ethyloxyphenyl]pent-4-enoate (36-5)

A mixture of 36-4 (402 mg, 1.05 mmol), 36-1 (361 mg, 1.18 mmol), palladium (11) acetate (24.0 mg, 0.10 mmol), triethylamine (0.29 ml, 1.99 mmol), tri-o-tolylphosphine (91 mg, 0.33 mmol), and $CH_3CN$ (5 ml) was placed in a sealed tube and heated at 100° for 18 hr. The solvent was evaporated and the residue subjected to flash chromatography (silica, 30% EtOAc/hexanes) to give 36-5 as a pale yellow oil.

$^1$H NMR (300 MHz, CDCl$_3$) δ 7.25 (d, J=11 Hz, 2H), 6.85 (d, J=11 Hz, 2H), 6.41 (d, J=13 Hz, 1 H), 5.95 (m, 1H), 4.93 (d, J=6 Hz, 1H), 4.2–3.95 (m, 6H), 2.98 (m, 2H), 2.81 (m, 4H), 1.81 (m, 7H), 1.50 (s, 9H), 1.43 (s, 9H), 1.12 (m, 2H), 0.95 (m, 3H).

2(S)-n-Butylsulfonylamino-5 [4-(2-N-Boc-piperidin-4-yl)ethyloxy-phenyl]pentanoic acid (36-6)

A solution of 36-5 (184 mg, 0.30 mmol) in 50 mL CH$_3$OH was treated with 24 mg of 10% Pd on C and hydrogenated on a Parr apparatus at 40 psi for 12 hr. The catalyst was removed by filtration through a bed of celite and the solution concentrated to give a colorless oil. This material was dissolved in 5 mL CH$_2$Cl$_2$, cooled to 0° C. and treated with TFA (2 mL). After stirring for 3 hr, the solvent was removed and the residue purified by reverse phase chromatography giving 36-6 as a white solid, following lyophylization.

$^1$H NMR (300 MHz, D$_2$O) δ 7.08 (d, J=11 Hz, 2H), 6.81 (d, J=11 Hz, 2H), 3.98 (m, 4H), 3.47 (d, J=12 Hz, 2H), 3.01 (m, 2H), 2.85–2.61 (m, 6H), 1.8–1.6 (m, 7H), 1.15 (m, 2H), 0.96 (m, 3H).

tert-Butyl 2(S)-n-Butylsulfonylamino-5-[4-(2-N-Boc-piperidin-4-yl)-ethyloxyphenyl]-5-oxopentanoate (36-7)

Oxygen was bubbled into a mixture of CuCl (10 mg, 0.11 mmol), PdCl$_2$ (6.0 mg, 0.03 mmol), and 5 ml of DMF which contained 10% H$_2$O. After 0.5 hr,. a solution of 36-5 in aqueous DMF (1.5 ml) was added and the mixture stirred under an O$_2$ atmosphere for 12 hr. The reaction was quenched by the addition of 10% KHSO$_4$ (3 ml) and extracted with CH$_2$Cl$_2$ (2×20 ml). The pooled CH$_2$Cl$_2$ extracts were dried (MgSO$_4$) concentrated and chromatographed (silica, 50% EtOAc/hexanes) to give 36-7 as a colorless glass. FAB MS, 611 (M+1).

$^1$H NMR (300 MHz, CDCl$_3$) δ 7.95 (d, J=11 Hz, 2H), 6.95 (d, J=11 Hz, 2H), 5.13 (d, J=7 Hz, 1H), 4.15 (m, 5H), 3.20 (m, 2H), 2.98 (m, 2H), 2.71 (m, 2H), 2.28 (m, 1H), 1.98 (m, 1H), 1.81 (m, 5H), 1.52 (s, 9H), 1.48 (s, 9H), 1.23 (m, 2H), 0.98 (m, 3H).

2 (S)-n-Butylsulfonylamino-5-[4-2-piperidin-4-yl)ethyloxyphenyl]-5-9xopentanoic acid (36-8)

A solution of 36-7 (64 mg, 0.105 mmol) in 10 ml EtOAc was cooled to −10° C. and HCl gas introduced for 10 min. After stirring at −10° C. for 2 hr the solution was evaporated and the residue purified by reverse phase chromatography (C18 column, 0.1% TFA/CH$_3$CN gradient) to give 36-8 as a white powder, following lyopholization.

$^1$H NMR (300 MHz, D$_{2O}$) 7.78 (d, J=11 Hz, 2H), 6.85 (d, J=11 Hz, 2H), 4.08 (m, 2H), 3.85 (m, 1H), 3.26 (d, J=13.8 Hz, 2H), 3.01–2.8 (m, 6H), 2.08 (m, 2H), 1.80 (d, J=14 Hz, 2H), 1.68 (m, 1H), 1.60 (m, 2H), 1.46 (m, 2H), 1.35 (m, 2H), 1.08 (m, 2H), 0.81 (m, 3H).

Therapeutic Treatment

Compounds of the invention may be used for inhibiting integrin protein-complex function relating to cell attachment activity. They may be administered to patients where inhibition of human or mammalian platelet aggregation or adhesion is desired. Thus, they may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

These compounds may be administered by any convenient means which will result in its delivery into the blood stream in substantial amount including continuous intravenous or bolus injection or oral methods. Compositions of the invention include compounds of the invention and pharmaceutically acceptable carriers, e.g. saline, at a pH level of for example 7.4, suitable for achieving inhibition of platelet aggregation. They may also be used in combination with anticoagulants such as heparin or warfarin. Intravenous or oral administration are presently contemplated as the preferred administration routes.

In one exemplary application, a suitable amount of compound is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.01–30 uM, preferably between about 0.03–3 uM. When this amount is achieved, an infusion of between about 0.1–100 µg per kilo per min., preferably between about 1–20 µg per kilo per min., most preferably 1–10 µg per kilo per min. is maintained to inhibit platelet aggregation. Advantageously, compounds of the present invention may be administered in divided doses of two, three, or four times daily. Should the patient need to undergo bypass surgery, administration may be stopped immediately and will not cause complications during surgery that would be caused by other materials such as aspirin or monoclonal antibodies.

Furthermore, preferred compounds for the present invention can be adminstered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather that intermittant throughout the dosage regime.

Oral dosages of the present invention, when used for the indicated effects, will range between about 0.01 mg per kg of body weight per day (mg/kg/day) to about 500 mg/kg/day and preferably 1.0–400 mg/kg/day and most preferably 1–300 mg/kg/day. The present invention also includes a pharmaceutical compostion comprising compounds of the present invention and tissue type plasminogen activitor or streptokinase. The invention also includes a method for promoting thrombolysis and preventing reocclusion in a patient which comprises administering to the patient an effective amount of compositions of the invention.

The present invention may be embodied in other specific forms without departing from the spirt or essential attributes thereof. Thus, the specific examples described above should not be interpreted as limiting the scope of the present invention.

Using the methods previously described, the following preferred compounds were prepared and evaluated:

| Compound | IC$_{50}$ (µM) Inhibition of Platelet Aggregation |
|---|---|
| HN-piperidinyl-(CH$_2$)$_2$NHC(O)-[pyridine-2,4-diyl]-C(O)NH-CH$_2$CH$_2$-CO$_2$H | 1.6 |
| HN-piperidinyl-(CH$_2$)$_2$NHC(O)-[pyridine-2,4-diyl]-C(O)NH-CH$_2$CH$_2$-CO$_2$H (isomer) | 1.1 |
| HN-piperidinyl-(CH$_2$)$_2$NHC(O)-[pyridine-3,5-diyl]-C(O)NH-CH(CO$_2$H)(CH$_2$NHSO$_2$Bu) | 0.11 |
| HN-piperidinyl-(CH$_2$)$_2$NHC(O)-[2-methylphenyl-diyl]-C(O)NH-CH$_2$CH$_2$-CO$_2$H | 0.45 |
| HN-piperidinyl-(CH$_2$)$_2$NHC(O)-[2-methylphenyl-diyl]-C(O)NH-CH(CO$_2$H)(CH$_2$NHSO$_2$Bu) | 0.15 |
| HN-piperidinyl-(CH$_2$)$_2$-N(CH$_3$)C(O)-[phenyl-1,3-diyl]-C(O)NH-CH(CO$_2$H)(CH$_2$NHSO$_2$Bu) | 0.023 |
| HN-piperidinyl-CH$_2$NHC(O)-[phenyl-1,4-diyl]-C(O)NH-CH(CO$_2$H)(CH$_2$NHSO$_2$Bu) | 0.14 |
| HN-piperidinyl-(CH$_2$)$_2$NHC(O)-[phenyl-1,4-diyl]-C(O)NH-CH(CO$_2$H)(CH$_2$NHSO$_2$Bu) | 0.020 |
| HN-piperidinyl-(CH$_2$)$_2$NHC(O)-[phenyl-1,4-diyl]-C(O)NH-CH(CO$_2$H)(CH$_2$NHSO$_2$-3-pyridyl) | 0.017 |
| HN-piperidinyl-(CH$_2$)$_3$NHC(O)-[phenyl-1,4-diyl]-C(O)NH-CH(CO$_2$H)(CH$_2$NHSO$_2$-3-pyridyl) | 0.052 |

| Compound | IC$_{50}$ (μM) Inhibition of Platelet Aggregation |
|---|---|
| (structure) | 0.15 |
| (structure) | 0.009 |
| (structure) | 0.019 |
| (structure) | 0.017 |
| (structure) | 0.01 |
| (structure) | 0.009 |
| (structure) | 0.056 |
| (structure) | 0.023 |

While the invention has been described and illustrated in reference to certain preferred embodiments thereof, those skilled in the art will appreciate that various changes, modification and substitutions can be made therein without departing from the spirt and the scope of the invention. For example, effective dosages other than the preferred doses as set fourth hereinabove may be applicable as a consequence of variations in the responsiveness of the mammal being treating for severity of clotting disorders or emboli, or for other indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be limited only by the scope of the claims which follow and that such claims be intepreted as broadly as is reasonable.

What is claimed is:

1. A compound of the formula

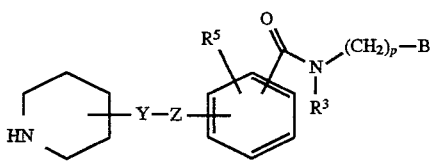

or its pharmaceutically acceptable salt thereof, where Y, when present, is $C_{0-8}$ alkylene,
$C_{0-8}$ alkylene-$NR^3$-CO-$C_{0-8}$ alkylene,
$C_{0-8}$ alkylene-$CONR^3$-$C_{0-8}$ alkylene,
$C_{0-8}$ alkylene-O-$C_{0-8}$ alkylene,
$C_{0-8}$ alkylene-$SO_n$-$C_{0-8}$ alkylene,
$(CH_2)_{0-6}$-$NR^3$-$(CH_2)_{0-6}$,
$C_{0-8}$ alkylene-$SO_2$-$NR^3$-$C_{0-8}$ alkylene-,
$C_{0-8}$ alkylene-CO-$C_{0-8}$ alkylene, or $C_{0-8}$ alkylene-CH(OH)-$C_{0-8}$-alkylene
where n is an integer from 0–2,
Z, when present, is
$(CH_2)m$, $(CH_2)_mO(CH_2)_k$, $(CH_2)_mNR^3(CH_2)_k$,

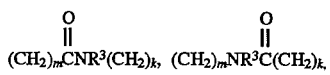

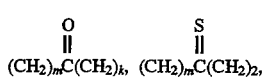

$(CH_2)_mSO_2(CH_2)_k$
$(CH_2)_mS(CH_2)_k$, $(CH_2)_mSO(CH_2)_k$,
$(CH_2)_mSO_2NR^3(CH_2)_k$, $(CH_2)_mNR^3SO_2(CH_2)_k$,
$(CH_2)C=C(CH_2)_k$, and
$(CH_2)_mCH(OH)(CH_2)_k$
where m and k are integers independently chosen from 0–6;
$R^5$ is
hydrogen,
$C_{1-6}$ alkyl, or
halogen;
$R^3$ is
hydrogen,
$C_{1-10}$ alkyl,
$C_{3-8}$ cycloalkyl,
aryl $C_{0-8}$ alkylene-,
amino $C_{0-8}$ alkylene-,
$C_{1-3}$ acylamino $C_{0-8}$ alkylene-,
$C_{1-6}$ alkylamino $C_{0-8}$ alkylene-,
$C_{1-6}$ dialkylamino $C_{0-8}$ alkylene-,
$C_{1-4}$ alkoxy $C_{0-6}$ alkylene-,
carboxy $C_{0-6}$ alkylene-,
$C_{1-3}$ alkoxycarbonyl $C_{0-6}$ alkylene-,
carboxy $C_{0-6}$ alkyleneoxy-, or
hydroxy $C_{0-6}$ alkylene-;
p is an integer from 0–6;
B is

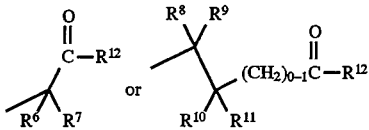

wherein $R^6$, $R^7$, $R^8$, $R^9$, $R^{10}$, and $R^{11}$ are independently chosen from:
hydrogen, fluoride, hydroxy $C_{1-6}$ alkylene-,
carboxy $C_{0-6}$ alkylene-,
$C_{1-8}$ alkyl, hydroxyl, $C_{1-6}$ alkyloxy,
aryl $C_{0-6}$alkyleneoxy-,
$C_{3-8}$ cycloalkyl,
aryl $C_{0-6}$ alkylene-, $C_{1-6}$ alkylcarbonyloxy-,
$C_{0-6}$ alkylamino $C_{0-6}$ alkylene-,
aryl $C_{0-6}$ alkyleneamino $C_{0-6}$alkylene-,
$C_{0-6}$ dialkylamino $C_{0-6}$ alkylene-,
$C_{0-6}$ alkylaminocarbonyloxy,
aryl $C_{0-6}$ alkyleneaminocarbonyloxy-,
$C_{1-8}$ alkylsulfonylamino $C_{0-6}$ alkylene-,
aryl $C_{0-6}$ alkylenesulfonylamino $C_{0-6}$ alkylene-,
$C_{1-8}$ alkyloxycarbonylamino $C_{0-8}$ alkylene-,
aryl $C_{0-8}$ alkyleneoxycarbonylamino $C_{0-8}$ alkylene-,
$C_{1-8}$ alkylcarbonylamino $C_{0-6}$ alkylene-,
aryl $C_{0-6}$ alkylenecarbonylamino $C_{0-6}$ alkylene-,
$C_{0-8}$ alkylaminocarbonylamino $C_{0-6}$ alkylene-,
aryl $C_{0-8}$ alkyleneaminocarbonylamino $C_{0-6}$ alkylene-,
$C_{0-8}$ alkylaminosulfonylamino $C_{0-6}$ alkylene-,
aryl $C_{0-8}$ alkyleneaminosulfonylamino $C_{0-6}$ alkylene-,
$C_{1-6}$ alkylsulfonyl $C_{0-6}$ alkylene-,
aryl $C_{0-6}$ alkylenesulfonyl $C_{0-6}$ alkylene-,
$C_{1-6}$ alkylcarbonyl $C_{0-6}$ alkylene-,
aryl $C_{0-6}$ alkylenecarbonyl $C_{0-6}$ alkylene-,
$C_{0-8}$alkylaminocarbonyl $C_{0-8}$ alkylene-,
aryl $C_{0-8}$ alkyleneaminocarbonyl $C_{0-8}$ alkylene-,
$C_{0-8}$ alkylaminosulfonyl $C_{0-8}$ alkylene-, and
aryl $C_{0-8}$ alkyleneaminosulfonyl $C_{0-8}$ alkylene-,
wherein groups may be unsubstituted or substituted with one or more sustituents selected from $R^1$ and $R^2$ which are independently selected from the group consisting of
hydrogen,
$C_{1-10}$ alkyl,
$C_{3-8}$ cycloalkyl,
aryl $C_{0-8}$ alkylene-,
amino $C_{0-8}$ alkylene-,
$C_{1-3}$ acylamino $C_{0-8}$ alkylene-,
$C_{1-6}$ alkylamino $C_{0-8}$ alkylene-,
$C_{1-6}$ dialkylamino $C_{0-8}$ alkylene-,
$C_{1-4}$ alkoxy $C_{0-6}$ alkylene-,
carboxy $C_{0-6}$ alkylene-,
$C_{1-3}$ alkoxycarbonyl $C_{0-6}$ alkylene-,
carboxy $C_{0-6}$ alkyloxy-, or
hydroxy $C_{0-6}$ alkylene-;
and wherein $R^{12}$ is chosen from:
hydroxy,
$C_{1-8}$ alkyloxy-,
aryl $C_{0-6}$ alkyleneoxy-,
$C_{1-8}$ alkylcarbonyloxy $C_{1-4}$ alkyleneoxy-,
aryl $C_{1-8}$ alkylenecarbonyloxy $C_{1-4}$ alkyleneoxy-, and
an L- or D-amino acid joined by an amide linkage and wherein the carboxylic acid moiety of said amino acid is as the free acid or is esterified by $C_{1-6}$ alkyl.

2. The compound of claim 1 having the formula

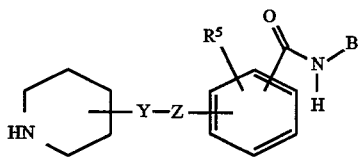

or its pharmaceutically acceptable salt thereof, where
Y is
$C_{1-3}$ alkylene,
$C_{0-8}$ alkylene-O-$C_{0-8}$ alkylene,
Z, when present, is $(CH_2)_m$, $(CH_2)_mO(CH_2)_k$, $(CH_2)_mNR^3(CH_2)_k$,

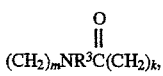

$(CH_2)_mNR^3SO_2(CH_2)_k$, where m and k are integers independently chosen from 0–6;

$R^3$ is hydrogen, $C_{1-10}$ alkyl, aryl $C_{0-8}$ alkylene-;

$R^5$ is hydrogen, or $C_{1-6}$ alkyl;

B is

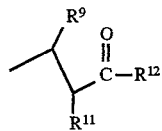

wherein $R^9$ and $R^{11}$ are independently chosen from:

hydrogen, fluoride, hydroxy, aryl $C_{0-6}$ alkylene-, $C_{1-8}$ alkylsulfonylamino $C_{0-6}$ alkylene-, aryl $C_{0-6}$ alkylenesulfonylamino $C_{0-6}$ alkylene-, $C_{1-8}$ alkylcarbonylamino $C_{0-6}$ alkylene-;

and wherein $R^{12}$ is chosen from:

hydroxy, and an L- or D-amino acid joined by an amide linkage and wherein the carboxylic acid moiety of said amino acid is as the free acid or is esterified by $C_{1-6}$ alkyl.

3. The compound of claim 2 selected from the group consisting of:

N-2-(4-Piperidinylethyl)-N'-(2-carboxyethyl)]-1,3-benzenedicarboxamide;

N-2-(4-Piperidinylethyl)-N'-[3-(2-fluoro)propanoic-acid]-1,3-benzene-dicarboxamide;

{N-2-(4-Piperidinylethyl)-N'-3-[3(R)-phenethylpropanoic acid]}-1,3-benzenedicarboxamide;

{N-[2-(4-Piperidinylethyl)]-N'-3-[3(R)-indolylethylpropanoic acid]}-1,3-benzenedicarboxamide;

N-(4-Piperidinylmethyl)-N'-3-[2(S)-n-butylsulfonylaminopropionic acid]-1,3-benzenedicarboxamide;

N-(4 -Piperidinylmethyl)-N'-(2-carboxyethyl)-1,3-benzenedicarboxamide;

N-2-(4-Piperidinyl)ethyl-N'-(2-carboxyethyl)-2-methyl-1,3-benzene-dicarboxamide;

3-[(4-Piperidinyl)methyl oxy]-N-(2-carboxyethyl) phenylacetamide;

4-(Piperidin-4-yl)phenyl-3-propionyl-[2(S)-n-butylsulfonylamino]-β-alanine;

3 -[3 -(Piperidin-4-ylmethyl)phenyl]propionyl-β-alanine;

{N-2-(4-Piperidinylethyl)-N'-3-[2(S)-n-butylsulfonylaminopropanoic acid]}-1,3-benzenedicarboxamide;

N-2-(4-Piperidinyl)ethyl-N'-3-[2(S)-n-butylsulfonylaminopropionic acid]-2-methyl- 1,3-benzenedicarboxamide;

{N-[2-(4-Piperidinyl)ethyl]-N-(phenethyl)}-N'-(2-carboxyethyl)-1,3-benzenedicarboxamide;

N-[2-(4-Piperidinyl)ethyl-N-propyl]-N'-(2-carboxyethyl)-1,3-benzene-dicarboxamide;

N-2-(4-Piperidinyl)ethyl-N'-[3-(2(S)-hexanoylaminopropionic acid)]-1,3-benzenedicarboxamide;

[N-2-(4-Piperidinyl)ethyl]-N'-[3-2(S)-thien-2-yl-sulfonylamino-propionic acid]- 1,3-benzenedicarboxamide;

3-[(2-Carboxyethyl)aminosulfonyl]-N-[2-(4-piperidinylethyl)]-benzamide;

3-[2-(4-Piperidinyl)ethylaminosulfonyl]-N-[(2-carboxyethyl)]-benzamide;

3-[(4-Piperidinyl)methylaminosulfonyl]-N-[(2-carboxyethyl)]-benzamide;

N-2-(4-Piperidinylethyl)-N'-3-(2-benzylpropionic acid)-1,3-benzenedicarboxamide;

3-(4-Carboxybutanoyl)-N-(4-piperidinylmethyl) benzenecarboxamide;

3 -(5-Carboxypentanoyl)-N-(4-piperidinylmethyl) benzenecarboxamide;

4-(Piperidin-4-yl)phenyl-3 -propionyl-β-alanine;

3-Chloro-4-[2-(Piperidin-4-yl)ethyloxy]phenylcarbonyl-2 (S)-phenylsulfonylamino-β-alanine;

4-[3-(Piperidin-3-yl)propyloxy]-N-[3-(2(S)-butylsulfonylamino)-propionic acid]benzamide;

4-[2-(Piperidin-4-yl)ethyloxy]phenylcarboxyl-2-(S)-hydroxy-β-alanine;

4-[3-(Piperidin-4-yl)propyl]benzoyl-2(S)-phenylsulfonylamino-β-alanine;

4-[2-(Piperidin-4-yl)oxyethyloxy]benzoyl-2(S)-phenylsulfonylamino-β-alanine;

3-[(Piperidin-4-ylmethyl)aminocarbonyl]benzoyl-2(S)-3-pyridyl-sulfonylamino-β-alanyl-glycine;

{N-2-(4-Piperidinylethyl)-N'-3-[ethyl 2(S)-n-butylsulfonylamino-propanoate]}-1,3-benzenedicarboxamide;

4-[2-(4-Piperidinyl)ethyloxy]-N-[3 -(2(S)-n-butylsulfonylamino)-propionate]benzamide;

4-[2-(4-Piperidinyl)ethyloxy]-N-[3-(2(S)-n-phenylsulfonylamino)-propionate]benzamide;

2(S)-n-Butylsulfonylamino-5-[4-2-(piperidin-4-yl) ethyloxyphenyl]-5-oxopentanoic acid;

N-2-(4-Piperidinylethyl)-N'-3-[2(S)-(3-pyridylsulfonylamino)-propanoic acid]-1,4-benzenedicarboxamide;

N-[3 -(4-Piperidinylpropyl)]-N'-3-[2(S)-(3-pyridylsulfonylamino)-propanoic acid]-1,4-benzenedicarboxamide;

3-[(4-Piperidinyl)methyloxy]-N-[3-(2-indol-3-yl)ethyl-propionic acid]phenyl acetamide, or a pharmaceutically acceptable salt thereof.

4. A method of blocking fibrinogen from acting at its platelet receptor site in a mammal, comprising administering a pharmacologically effective amount of a compound as claimed in claim 1.

5. A method of preventing thrombus and embolus formation in a mammal, in need thereof, comprising administering a pharmacologically effective amount of a compound as claimed in claim 1.

6. A method of treating thrombus and embolus formation in a mammal, in need thereof, comprising administering a pharmacologically effective amount of a compound as claimed in claim 1.

7. A method of inhibiting aggregation of blood platelets in a mammal, comprising administering a pharmacologically effective amount of a compound as claimed in claim 1.

8. A method of blocking fibrinogen from acting at its platelet receptor site in a mammal, comprising administering a pharmacologically effective amount of a compound of claim 3.

9. A method of preventing thrombus and embolus formation in a mammal, in need thereof, comprising administering a pharmacologically effective amount of compound of claim 3.

10. A method of treating thrombus and embolus formation in a mammal, in need thereof, comprising administering a pharmacologically effective amount of a compound of claim 3.

11. A method of inhibiting aggregation of blood platelets in a mammal, comprising administering a pharmacologically effective amount of a compound of claim 3.

12. A pharmaceutical composition, comprising a compound as claimed in claim 1, and a pharmaceutically acceptable carrier.

13. A method for inhibiting the aggregation of blood platelets in a mammal, comprising administering the composition of claim 12.

* * * * *